(12) United States Patent
Kitamura et al.

(10) Patent No.: US 12,171,836 B2
(45) Date of Patent: Dec. 24, 2024

(54) LONG-ACTING ADRENOMEDULLIN DERIVATIVE

(71) Applicant: University of Miyazaki, Miyazaki (JP)

(72) Inventors: Kazuo Kitamura, Miyazaki (JP); Motoo Yamasaki, Miyazaki (JP)

(73) Assignee: UNIVERSITY OF MIYAZAKI, Miyazaki (JP)

( * ) Notice: Subject to any disclaimer, the term of this patent is extended or adjusted under 35 U.S.C. 154(b) by 0 days.

(21) Appl. No.: 17/937,788

(22) Filed: Oct. 4, 2022

(65) Prior Publication Data

US 2023/0142095 A1 May 11, 2023

Related U.S. Application Data

(60) Division of application No. 17/036,491, filed on Sep. 29, 2020, now Pat. No. 11,478,551, which is a continuation of application No. 15/760,310, filed as application No. PCT/JP2016/077543 on Sep. 16, 2016, now Pat. No. 10,842,879.

(30) Foreign Application Priority Data

Sep. 18, 2015 (JP) .................. 2015-184685

(51) Int. Cl.
| | |
|---|---|
| C07K 14/575 | (2006.01) |
| A61K 38/22 | (2006.01) |
| A61K 47/60 | (2017.01) |
| A61P 9/08 | (2006.01) |
| A61P 9/12 | (2006.01) |
| A61P 29/00 | (2006.01) |
| A61K 38/00 | (2006.01) |

(52) U.S. Cl.
CPC ............. *A61K 47/60* (2017.08); *A61K 38/22* (2013.01); *A61P 9/08* (2018.01); *A61P 9/12* (2018.01); *A61P 29/00* (2018.01); *C07K 14/575* (2013.01); *A61K 38/00* (2013.01)

(58) Field of Classification Search
CPC ........ A61K 47/60; A61K 38/22; A61K 38/00; C07K 14/575; A61P 29/00; A61P 9/12; A61P 9/08; A61P 9/00; A61P 37/00
See application file for complete search history.

(56) References Cited

U.S. PATENT DOCUMENTS

| | | | |
|---|---|---|---|
| 5,639,855 A | 6/1997 | Kitamura et al. | |
| 5,824,784 A | 10/1998 | Kinstler et al. | |
| 2002/0115833 A1 | 8/2002 | Burg et al. | |
| 2009/0252703 A1 | 10/2009 | Gregg, Jr. et al. | |
| 2010/0286035 A1 | 11/2010 | Ohtaki et al. | |
| 2012/0178676 A1 | 7/2012 | Barrack et al. | |
| 2012/0178678 A1 | 7/2012 | Barrack et al. | |
| 2013/0296260 A1 | 11/2013 | Kitamura et al. | |
| 2014/0155329 A1 | 6/2014 | Hsu et al. | |
| 2014/0287984 A1 | 9/2014 | Flamme et al. | |
| 2018/0170991 A1 | 6/2018 | Kitamura et al. | |

FOREIGN PATENT DOCUMENTS

| | | |
|---|---|---|
| CN | 103998063 A | 8/2014 |
| EP | 3127914 A1 | 2/2017 |
| JP | H09-506116 A | 6/1997 |
| JP | 2774769 B2 | 4/1998 |
| JP | 2004-525097 | 8/2004 |
| JP | 2005-525302 A | 8/2005 |
| JP | 4830093 B | 9/2011 |
| JP | 2013-533217 A | 8/2013 |
| JP | 2014-532682 A1 | 12/2014 |
| KR | 10-2013-0115086 A | 10/2013 |
| WO | 96/11953 A1 | 4/1996 |
| WO | 02/49673 A2 | 6/2002 |
| WO | 03/044056 A2 | 5/2003 |
| WO | 2005/044846 A1 | 5/2005 |
| WO | 2008/051383 A2 | 5/2008 |
| WO | 2009/040029 A2 | 4/2009 |
| WO | 2009/044918 A1 | 4/2009 |
| WO | 2011/146518 A2 | 11/2011 |
| WO | 2012/096411 A1 | 7/2012 |
| WO | 2012/138867 A1 | 10/2012 |

(Continued)

OTHER PUBLICATIONS

Kubo et al (Peptides, 2014, 57, 118-121) (Year: 2014).*
Roberts et al (Advanced Drug Discovery Reviews, 2002, 54, 459-476) (Year: 2002).*
Kitamura et al (Microscopy Research and Technique, 2002, 57, 3-13) (Year: 2002).*
Bailon et al (PSTT, vol. 1, No. 8, Nov. 1998) (Year: 1998).*
Kubo et al., "Biological Properties of Adrenomedullin Conjugated with Polyethylene Glycol," Peptides, 57: 118-121 (2014).
Kitamura et al., "Adrenomedullin: A Novel Hypotensive Peptide Isolated from Human Pheochrornocytorna," Biochemical and Biophysical Research Communications,192 (2): 553-560 (1993).
Belloni et al., "Structure-Activity Relationships of Adrenomedullin in the Adrenal Gland," Endocrine Research, 24 (3&4): 729-730 (1998).

(Continued)

*Primary Examiner* — Sudhakar Katakam
(74) *Attorney, Agent, or Firm* — Morgan, Lewis & Bockius LLP

(57) ABSTRACT

The invention provides a novel adrenomedullin derivative sustainable for a long period which is capable of substantially suppressing unwanted side effects while maintaining pharmacological effects of adrenomedullin. In an exemplary embodiment, the invention relates to a compound represented by formula (I): A-CH$_2$—B (I) [wherein A is a modifying group comprising one or more polyethylene glycol groups, and B is a peptide moiety derived from adrenomedullin or a modified form thereof with adrenomedullin activity, wherein the peptide moiety B is linked to the other moieties through a covalent bond of the nitrogen atom of the N-terminal α-amino group of the peptide moiety B to the carbon atom of the methylene group] or a salt thereof, or a hydrate thereof.

16 Claims, 21 Drawing Sheets

Specification includes a Sequence Listing.

(56) References Cited

FOREIGN PATENT DOCUMENTS

| WO | 2013/064508 A1 | 5/2013 |
|---|---|---|
| WO | 2015/141819 A1 | 9/2015 |

OTHER PUBLICATIONS

Champion et al., "Catecholamine Release Mediates Presser Effects of Adrenomedullin-(15-22) in the Rat," Hypertension, 28 (6): 1041-1046 (1996).

Champion, Hunter C., "Structure-Activity Relationships of Adrenomedullin in the Circulation and Adrenal Gland," Regulatory Peptides, 85: 1-8 (1999).

Eguchi et al., "Structure-Activity Relationship of Adrenomedullin, a Novel Vasodilatory Peptide, in Cultured Rat Vascular Smooth Muscle Cells," Endocrinology, 135 (6): 2454-2458 (1994).

Garcia et al., "Synthesis, Biological Evaluation, and Three-Dimensional Quantitative Structure-Activity Relationship Study of Small-Molecule Positive Modulators of Adrenornedullin," Journal of Medicinal Chemistry, 48(12): 4068-4075 (2005).

Mitsuda et al, "Large-scale Production of Functional Human Adrenomedullin: Expression, Cleavage, Amidation, and Purification," Protein Expression and Purification, 25: 448-455 (2002).

Roldos et al., "Small-Molecule Negative Modulators of Adrenomedullin: Design, Synthesis, and 3D-QSAR Study," ChemMedChem, 3: 1345-1355 (2008).

Watanabe et al., "Vasopressor Activities of N-Terminal Fragments of Adrenomedullin in Anesthetized Rat," 1996, Biochemical and Biophysical Research Communications, 219 (1): 59-63 (1996).

Kato et al., "Bench-to-Bedside Pharmacology of Adrenomedullin," European Journal of Pharmacology, 764: 140-148 (2015).

International Search Report issued in related International Patent Application No. PCT/JP2016/077543 dated Dec. 13, 2016.

Japanese Office Action issued in related Japanese Patent Application No. 2017-540025 dated Sep. 8, 2020.

Roberts et al., "Chemistry for Peptide and Protein PEGylation," Advanced Drug Delivery Reviews, 54: 459-476 (2002).

Canadian Office Action issued in related Canadian Patent Application No. 2997131 dated Mar. 14, 2019.

Hermanson, "Bioconjugate Techniques," Academic Press, Boston MA (2008).

Extended European Search Report issued in related European Patent Application No. 16846659.7 dated Apr. 17, 2019.

Roberts et al., "Chemistry for Peptide and Protein PEGylation," Advanced Drug Delivery Reviews, 64: 116-127 (2012).

Singapore Office Action issued in related Singapore Patent Application No. 11201802180T dated Jan. 18, 2019.

Australian Office Action issued in related Australian Application No. 2016324119 dated Nov. 9, 2018.

First Examination Report issued in related New Zealand Patent Application No. 740534 dated Jul. 26, 2018.

* cited by examiner

```
                            SEQUENCE LISTING

Sequence total quantity: 12
SEQ ID NO: 1              moltype = AA   length = 52
FEATURE                   Location/Qualifiers
source                    1..52
                          mol_type = protein
                          organism = Homo sapiens
SEQUENCE: 1
YRQSMNNFQG LRSFGCRFGT CTVQKLAHQI YQFTDKDKDN VAPRSKISPQ GY         52

SEQ ID NO: 2              moltype = DNA   length = 1449
FEATURE                   Location/Qualifiers
source                    1..1449
                          mol_type = genomic DNA
                          organism = Homo sapiens
SEQUENCE: 2
ctggatagaa cagctcaagc cttgccactt cgggcttctc actgcagctg ggcttggact  60
tcggagtttt gccattgcca gtgggacgtc tgagactttc tccttcaagt acttggcaga 120
tcactctctt agcagggtct gcgcttcgca gccgggatga agctggtttc cgtcgccctg 180
atgtacctgg gttcgctcgc cttcctaggc gctgacaccg ctcggttgga tgtcgcgtcg 240
gagtttcgaa agaagtggaa taagtgggct ctgagtcgtg ggaagaggga actgcggatg 300
tccagcagct acccaccgg gctcgctgac gtgaaggccg ggcctgccca gacccttatt 360
cggccccagg acatgaaggg tgcctctcga agccccgaag acagcagtcc ggatgccgcc 420
cgcatccgag tcaagcgcta ccgccagagc atgaacaact tccagggcct ccggagcttt 480
ggctgccgct tcgggacgtg cacggtgcag aagctggcac accagatcta ccagttcaca 540
gataaggaca aggacaacgt cgcccccagg agcaagatca gcccccaggg ctacggccgc 600
cggcgccggc gctccctgcc cgaggccggc ccgggtcgga ctctggtgtc ttctaagcca 660
caagcacacg gggctccagc cccccgagt ggaagtgctc cccactttct ttaggattta 720
ggcgcccatg gtacaaggaa tagtcgcgca agcatcccgc tggtgcctcc cgggacgaag 780
gacttccga gcggtgtggg gaccgggctc tgacagccct gcggagaccc tgagtccggg 840
aggcaccgtc cggcggcgag ctctggcttt gcaagggccc ctccttctgg gggcttcgct 900
tccttagcct tgctcaggtg caagtgcccc aggggcggg gtgcagaaga atccgagtgt 960
ttgccaggct taaggagagg agaaactgag aaatgaatgc tgagaccccc ggagcagggg 1020
tctgagccac agccgtgctc gcccacaaac tgatttctca cggcgtgtca ccccaccagg 1080
gcgcaagcct cactattact tgaactttcc aaaacctaaa gaggaaaagt gcaatgcgtg 1140
ttgtacatac agaggtaact atcaatattt aagttttgtg ctgtcaagat ttttttttga 1200
acttcaaata tagagatatt tttgtacgtt atatattgta ttaagggcat tttaaaagca 1260
attatattgt cctccctat tttaagacgt gaatgtctca gcgaggtgta aagttgttcg 1320
ccgcgtggaa tgtgagtgtg tttgtgtgca tgaaagagaa agactgatta cctcctgtgt 1380
ggaagaagga aacaccgagt ctctgtataa tctatttaca taaatgggt gatatgcgaa 1440
cagcaaacc                                                        1449

SEQ ID NO: 3              moltype = AA   length = 52
FEATURE                   Location/Qualifiers
source                    1..52
                          mol_type = protein
                          organism = Sus scrofa
SEQUENCE: 3
YRQSMNNFQG LRSFGCRFGT CTVQKLAHQI YQFTDKDKDG VAPRSKISPQ GY         52

SEQ ID NO: 4              moltype = DNA   length = 1493
FEATURE                   Location/Qualifiers
source                    1..1493
                          mol_type = genomic DNA
                          organism = Sus scrofa
SEQUENCE: 4
gcggaacagc tcgagccttg ccacctctag tttcttacca cagcttggac gtcgggttt    60
tgccactgcc agagggacgt ctcagacttc atcttcccaa atcttggcag atcaccccct 120
tagcagggtc tgcacatctc agccgggatg aagctggttc ccgtagccct catgtacctg 180
ggctcgctcg ccttcctggg cgctgacaca gctcggctcg acgtggcggc agagttccga 240
aagaaatgga ataagtgggc tctaagtcgt ggaaaaagag aacttcggct gtccagcagc 300
taccccaccg ggatcgccga cttgaaggcc gggcctgccc agactgtcat tcggcccag 360
gatgtgaagg gctcctctcg cagcccccag gccagcattc cggatgcagc ccgcatccga 420
gtcaagcgct accgccagag tatgaacaac ttccagggcc tgcggagctt cggctgtcgc 480
tttgggacgt gcaccgtgca gaagctggcg caccagatct accagttcac ggacaaagac 540
aaggacggcg tcgccccccg gagcaagatc agccccccagg gctacggccg ccggcgccga 600
```

```
cgctctctgc ccgaagccag cctgggccgg actctgaggt cccaggagcc acaggcgcac   660
ggggccccgg cctccccggc gcatcaagtg ctcgccactc tctttaggat ttaggcgcct   720
actgtggcag cagcgaacag tcgcgcatgc atcatgccgg cgcttcctgg ggcgggggc    780
ttcccggagc cgagcccctc agcggctggg gcccgggcag agacagcatt gagagaccga   840
gagtccggga ggcacagacc agcggcgagc cctgcatttt caggaacccg tcctgcttag   900
aggcagtgtt ctcttcggct taatccagcc cgggtccccg ggtgggggtg gagggtgcag   960
aggaatccaa aggagtgtca tctgccaggc tcacggagag gagaaactgc gaagtaaatg  1020
cttagacccc caggggcaag ggtctgagcc actgccgtgc cgcccacaaa ctgatttctg  1080
aagggaaata accccaacag ggcgcaagcc tcactattac ttgaactttc caaaacctag  1140
agaggaaaag tgcaatgtat gttgtatata aagaggtaac tatcaatatt taagtttgtt  1200
gctgtcaaga ttttttttg taacttcaaa tatagagata ttttttgtacg ttatatattg  1260
tattaagggc attttaaaac aattgtattg ttccctccc ctctatttta atatgtgaat   1320
gtctcagcga ggtgtaacat tgtttgctgc gcgaaatgtg agagtgtgtg tgtgtgtgtg  1380
cgtgaaagag agtctggatg cctccttggg aagaagaaaa caccatatct gtataatcta  1440
tttacataaa atgggtgata tgcgaagtag caaaccaata aactgtctca atg          1493

SEQ ID NO: 5                moltype = AA  length = 52
FEATURE                     Location/Qualifiers
source                      1..52
                            mol_type = protein
                            organism = Canis familiaris
SEQUENCE: 5
YRQSMNNFQG PRSFGCRFGT CTVQKLAHQI YQFTDKDKDG VAPRSKISPQ GY             52

SEQ ID NO: 6                moltype = DNA  length = 1432
FEATURE                     Location/Qualifiers
source                      1..1432
                            mol_type = genomic DNA
                            organism = Canis familiaris
SEQUENCE: 6
ggttttgcca gcaccagagc gacgtctcag accttctcct cccgatcttt ggcagatcac    60
cccctcagca gggtctgcgc atcgccgcca gcatgaagct ggttcccgtc gccctcttat   120
acctgggctc cctcgccttc ttgggcgcgg acaccgcacg gctagacgtg gcgtcagagt   180
tccgaaagaa gtgaataaaa tgggctgtaa gtcgtggaaa gagggaactt cgagtgtcca   240
gcagctatcc caccgggctc gctgaagtga aggccgggcc ggccccagact cttattcgga   300
cccaggacgt gaagggcgcc tctcgcaacc cccagaccag cggtccggac gccgcccgca   360
tccgagtcaa acgctaccgc cagagtatga acaatttcca gggcccgcgg agcttcggct   420
gccgcttcgg aacgtgcacg gtgcagaaac tggcgcacca gatctaccag ttcacagaca   480
aggacaagga cggcgtcgcc cccaggagca agattaccag tcagggctac ggccgccggc   540
gccggcgctc cctgcccgag cccggccttc gccggactct gttgttcccg gagccacggc   600
caggcggggc tccggccccc cgggcgcatc aggtgctcgc caacctcctt aagatgtagg   660
cgcctgtggc agcagcgaac tggcgcgcgt gtgcatcccg ctggcttccc cctgggcgga   720
gggcttcccc gagccgagcc cctctgccga tggaagtcgg gcagagaccg ggattccgga   780
aggcaccgtc ccgcggccag ccctggcttt gcgcgagccc cttctcctcg gaggcacgga   840
tccctctgtc ccaagccggc ccaggtgtcc cgtgggggc agaggaatgc aagggaggcc    900
tgccaggctc acggagagga ttaactgaga attaaatgag aattaaatgc ttgagaccct   960
ccccctcc cccccaggga caggggtctg agtcactgcc gtgcctgccc acaaactgat    1020
ttctcacggg gtgtcacccc accggggcgc aagcctcact attacttgaa ctttccaaaa  1080
cctagagagg aaaagtgcaa tgcgtgttgt atatacagag gtaactatca atatttaagt  1140
tcgttgctgt cagaagattt ttttgtaac ttcaaatata gagatatttt tgtacgttat   1200
atattgtatt aagggcattt aaaaaccatt gcattgctcc cctccccact tatttttata  1260
cgtgaatgtc tcagcgaggt gtaacgttgt ttttgctgca gagtgtgtga gtgtgcgtga  1320
gagacttatt acctctgtg gaagaaggaa caccgtgtct ctgcattatc tatttacata   1380
aaatgggtga tatgcgaaaa tagcaaatca ataataaacg gtctcgatgc tg           1432

SEQ ID NO: 7                moltype = AA  length = 52
FEATURE                     Location/Qualifiers
source                      1..52
                            mol_type = protein
                            organism = Bos taurus
SEQUENCE: 7
YRQSLNNFQG LRSFGCRFGT CTVQKLAHQI YHFTDKDKDG SAPRSKISPQ GY             52

SEQ ID NO: 8                moltype = DNA  length = 1439
FEATURE                     Location/Qualifiers
source                      1..1439
                            mol_type = genomic DNA
                            organism = Bos taurus
SEQUENCE: 8
cgggaaacag ctcgaacctt ctcacttttg gcttctcact gcagcttcga cgtcggggtt    60
ttgccactgc cagaacgccg tctcagactt aatactccaa agaattttgg cagatcaccc   120
cctcagcagg gtctgcgcat cgccgccggg atgaagctgg ttcccgtcgc cctcctgtac   180
ctgggggtcgc tcgccttcct aggcgtggac acggcacggc tcgacgtggc ggcagagttc   240
cgaaagaaat ggaataagtg ggctctaagt cgtggaaaaa gaaacttcg cgagtccagt    300
agctacccca ccgggctcgc cgacgtgaag gccgggcctg ccagactct tattcggccc    360
caggatgtaa agggcgcctc tcgaagccct caggccagca gtcctgacgc agcccgcatc    420
cgagtcaagc gctaccgcca gagtttgaac aacttcaggg gctgcgagg cttcggttgt    480
cgcttcggga catgcacggt gcagaagttg gcgcatcaga tctaccattt cacggacaag    540
gacaaggacg gatccgcccc caggagcaag atcagccccc agggctacgg ccgtcggcgc    600
```

```
cgacgttcac tgcctgaggc cggcttgggt cggactctat tacagcctcc agagccaaag   660
ctgcgagggg ccccggactc ccgggtgcat caagtacttg ccaccctcag gatttaggcg   720
cctgggcagc agcgaacagt cgcgcacgca tctcgccggc acctcttcgg gcgggagggc   780
ttccgcgagc cgagcccctc actcagccta tgggcccggg ctgagaacag ccctgagaga   840
ccgagagtcc aggaggcacc gtccggcagc cagcgagcac tggctttgca ggaacccgtc   900
ctcctcggag gggaggcagt gttctcttca ctctaattgg ggccaggtgc agtttctcct   960
ctccgtgagc ctggcagacg ctcacggaga ggagaaactg cgaaataaat gatgagaccc  1020
tcaggggcaa gggtctgagc cactgccgtg cccgcccaca aactgattcc tgatgggggt  1080
gtcaccccac cggggtgcaa gcctcactat tacttgaact ttccgaaacc tagagaggaa  1140
aagtgcaatg agtgttgtat atacagagat aattatcaat atttaaattt gttgttgtca  1200
agattttttt tgtaacttca aatatagaga tattttgta cgttatatat tgtattaagg  1260
gcattttaaa gcaattgtat tgttccoctc ccctctattt taataagtga atgtctcagc  1320
gagatgcaac gttgtttgct gcgtggaatg tgagagtgtg tgcgtgaaag agatgagttg  1380
cctcttgtgg aagaagaaaa caccgtgtct gtataatcta tttacataaa gtgggccgg   1439

SEQ ID NO: 9            moltype = AA  length = 50
FEATURE                 Location/Qualifiers
source                  1..50
                        mol_type = protein
                        organism = Rattus norvegicus
SEQUENCE: 9
YRQSMNQGSR STGCRFGTCT MQKLAHQIYQ FTDKDKDGMA PRNKISPQGY              50

SEQ ID NO: 10           moltype = DNA  length = 1376
FEATURE                 Location/Qualifiers
source                  1..1376
                        mol_type = genomic DNA
                        organism = Rattus norvegicus
SEQUENCE: 10
tccagccttt accgctcctg gtttctcggc ttctcatcgc agtcagtctt ggactttgcg    60
ggttttgccg ctgtcagaag gacgtctcgg actttctgct tcaagtgctt gacaactcac   120
cctttcagca gggtatcgga gcatcgctac agaatgaagc tggtttccat cgccctgatg   180
ttattgggtt cgctcgccgt tctcggcgcg gacaccgcac ggctcgacac ttcctcgcag   240
ttccgaaaga agtggaataa gtgggcgcta agtcgtggga gagggaact acaagcgtca   300
agcagctacc ctacggggct cgttgatgag aagacagtcc cgacccagac tcttgggctc   360
caggacaagc agagcacgtc tagcacccca caagccagca ctcagagcac agcccacatt   420
cgagtcaaac gctaccgcca gagcatgaac caggggtccc gcagcactgg atgccgcttt   480
gggacctgca caatgcagaa actggctcac cagatctacc agtttacaga caaagacaag   540
gacggcatgg ccccccagaa caagatcagc ctcaaggct atggccgcg gcgccggcgt   600
tccctgccag aggtcctccg agcccggact gtggagtcct cccaggagca gacacactca   660
gctccagcct ccccggcgca ccaagacatc tccagagtct ctaggttata ggtgcgggtg   720
gcagcattga acagtcgggc gagtatccca ttggcgcctg cggaatcaga gagcttcgca   780
ccctgagccg actgagacaa tcttgcagag atctgcctgg ctgccccctag ggaggcagga   840
ggaacccaag atcaagccag gctcacgtca gaaaccgaga attacaggct gatactctct   900
ccgggcaggg gtctgagcca ctgccttgcc cgctcataaa ctggttttct cacggggcat   960
acggctcatt acttacttga actttccaaa acctagcgag gaaaagtgca atgcttgtta  1020
tacagccaaa ggtaactatc atatttaagt ttgttgtgt caagaggttt ttttttttgt  1080
aacttcaaat atatagaaat attttttgtac gttatatatt gtattaaggg catttttaag  1140
cgattatatt gtcaccttcc cctattttaa gaagtgaatg tctcagcaag gtaaggtt   1200
gtttggttcc gtgtgtgtgt gtgtgtgtgt gtgtgtgtgt gtgtgtgtgt gtgtgtaagg  1260
tggagagcgc ctgattaccg cctgtggatg aagaaaaaac attgtgtctt ctataatcta  1320
tttacataaa atatgtgatc tgggaaaaag caaaccaata aactgtctca atgctg      1376

SEQ ID NO: 11           moltype = AA  length = 50
FEATURE                 Location/Qualifiers
source                  1..50
                        mol_type = protein
                        organism = Mus musculus
SEQUENCE: 11
YRQSMNQGSR SNGCRFGTCT FQKLAHQIYQ LTDKDKDGMA PRNKISPQGY              50

SEQ ID NO: 12           moltype = DNA  length = 1381
FEATURE                 Location/Qualifiers
source                  1..1381
                        mol_type = genomic DNA
                        organism = Mus musculus
SEQUENCE: 12
cttggtgaca ctagacagag caactccagc gttaccgctc ccgctcctgg tttctcggct    60
tctcatcgca gtcaatcttg gactttgggg ttttgctact gtcagaagga cttcttttctg   120
cttcaagtgc ttgacaacgc accccttat cagggtatca gagcatcgcc acagaatgaa   180
gctggtttcc atcaccctga tgttattggg ttcactcgct ttcctaggcg cggacactgc   240
agggccagat actccttcgc agttccgaaa gaagtggaat aagtgggcgc taagtcgtgg   300
gaagagggaa ctacaagcat ccagcagcta ccctacggga ctcgctgatg agacgacagt   360
tcctacccag actcttgatc cattcctgga cgagcagaac aactggcc tactacaagc   420
cagcaatcag agcgaagccc acattcgtgt caaacgctac cgccagagca tgaaccaggg   480
ttcccgcagc aatggatgcc gcttcgggac ctgcacattt cagaaattgg cccaccagat   540
ctaccagcta acagacaaag acaaggacgg catggctccc agaacaaga tcagccctca   600
aggctatggc cgccggcgcc ggcgttccct gctgaggtc ctccggtccc ggactgtgga   660
gtcctcccag gagcagacac acacagcccc aggccctgg gcgcacatct ccagactctt   720
```

```
taggatatag gtgcgggtga cagcattgaa cagtcgggcg agtatcccgt tggcgcctgc    780
ggaatcagag aacttcgcac cggggcggac tgagacaatc ctgcagagat ctgcctggct    840
gccctaggg gaggcagagg aacccaagac caagccaggc tcatgccaga aaccgagact    900
tacaggctga tactctccgg gcagggtct gagccactgc cttgcccgct cataaactgg    960
tttctcacgg ggcataagcc tcattactac ttgaactttc caaaacctag cgaggaacgt   1020
gcaatgcttg ttgtccagcc aaaggtaact atagtattta agtttgttgc tgtcaaggtt   1080
ttttttttg taacttcaaa tatatagaga tatttttgta cgttatatat tgtattaagg   1140
gcattttaaa gtgattatat tgtcaccttc ccctatttta agacgtgaat gtctcagcaa   1200
ggtgtaaggt tgtttggttc cgtgtgtgtg tgtgtgtgtg tgtgtgtgtg tgtgtgtgtg   1260
taaggtggag agcgcctgat tatcgcctgt ggatgaagaa aaaacattgt gtttcctata   1320
atctatttac ataaaatatg tgatctggga aaaagcaaac caataaactg tctcaatgct   1380
g                                                                   1381
```

LONG-ACTING ADRENOMEDULLIN DERIVATIVE

REFERENCE TO AN ELECTRONIC SEQUENCE LISTING

The contents of the electronic sequence listing (sequence-listing.xml; Size: 20,192 bytes; and Date of Creation: Oct. 3, 2022) is herein incorporated by reference in its entirety.

TECHNICAL FIELD

The invention relates to long-acting adrenomedullin derivatives.

BACKGROUND ART

Adrenomedullin (hereinafter, also described as "AM") is a bioactive peptide which was isolated and identified from pheochromocytoma in 1993 (Non Patent Literature 1). At the beginning of the discovery, AM was found to exert a strong vasodilatory hypotensive effect. For example, Patent Literature 1 describes a peptide having a blood pressure-lowering effect that comprises the amino acid sequence of human AM.

Subsequent studies revealed that AM exerts diverse pharmacological effects such as a cardiovascular protective effect, an anti-inflammatory effect, an angiogenic effect, and a tissue repair promoting effect. In an effort to apply the pharmacological effects of AM to treatment of disease, administration of AM to patients with different diseases has been attempted. AM is expected to be useful as a therapeutic agent for inflammatory bowel diseases, pulmonary hypertension, peripheral vascular diseases, or acute myocardial infarction, among others.

For example, Patent Literature 2 describes an agent for preventing or treating nonbacterial inflammatory bowel diseases, wherein the agent comprises, as an active ingredient, adrenomedullin or a derivative thereof that has an activity to suppress nonbacterial inflammation, or a salt thereof that has an activity to suppress nonbacterial inflammation.

Patent Literature 3 describes a method for preventing or treating an inflammatory bowel disease for which the use of a steroid preparation, an immunosuppressant, or a biological product is difficult or insufficiently effective in a patient in need of prevention or treatment of the inflammatory bowel disease, the method comprising administering an effective amount of adrenomedullin, a modified form thereof having an activity of suppressing inflammation, or a salt of the adrenomedullin or the modified form having an activity of suppressing inflammation, to the patient.

Structure-activity relationship studies of AM have advanced identification of essential sequences that can contribute bioactivity of AM (Non Patent Literatures 2 to 9).

Peptides are generally known to have a short half-life due to a metabolism in a living body (such as in blood). Therefore, in the case of using peptides as active ingredients in medicaments, forms of peptide derivatives in which other groups are linked to the peptides can prolong half-life in a living body and improve pharmacokinetics, in some cases.

For example, Patent Literature 4 describes a biologically active intermedin peptide or adrenomedullin peptide characterized by having a serum half-life exceeding 1.5 hours. The literature states that an alkyl group and a peptide moiety are linked via an amide bond.

Patent Literature 5 describes an AM derivative linked to a polyethylene glycol (hereinafter, also described as "PEG") group via the phenolic hydroxy group of $Tyr^1$ of AM.

Patent Literature 6 describes a method comprising reacting PEG-aldehyde with a free amino group of a peptide to produce a peptide derivative having the PEG group linked to the free amino group of the peptide. The literature describes AM as the peptide.

Non Patent Literature 10 describes an AM derivative in which a PEG group is linked to the N-terminal α-amino group of AM via an amide bond. The literature states that blood half-life of the AM derivative having the linked PEG group was prolonged.

CITATION LIST

Patent Literature

Patent Literature 1: JP Patent No. 2774769
Patent Literature 2: JP Patent No. 4830093
Patent Literature 3: International Publication No. WO 2012/096411
Patent Literature 4: International Publication No. WO 2012/138867
Patent Literature 5: International Publication No. WO 2013/064508
Patent Literature 6: U.S. Patent Publication. No. US 2009/0252703

Non Patent Literature

Non Patent Literature 1: Kitamura K, Kangawa K, Kawamoto M, Ichiki Y, Nakamura S, Matsuo H, Eto T. Adrenomedullin: a novel hypotensive peptide isolated from human pheochromocytoma. Biochem Biophys Res Commun, 30 Apr. 1993, Volume 192, Issue 2, pp. 553-560.
Non Patent Literature 2: Belloni, A. S. et al., Structure-activity relationships of adrenomedullin in the adrenal gland. Endocr Res, 1998, Volume 24, Issue 3-4, p. 729-30.
Non Patent Literature 3: Champion, H. C. et al., Catecholamine release mediates pressor effects of adrenomedullin-(15-22) in the rat. Hypertension, 1996, Volume 28, Issue 6, p. 1041-6.
Non Patent Literature 4: Champion, H. C., G. G. Nussdorfer, and P. J. Kadowitz, Structure-activity relationships of adrenomedullin in the circulation and adrenal gland. Regul Pept, 1999, Volume 85, Issue 1, p. 1-8.
Non Patent Literature 5: Eguchi, S. et al., Structure-activity relationship of adrenomedullin, a novel vasodilatory peptide, in cultured rat vascular smooth muscle cells. Endocrinology, 1994, Volume 135, Issue 6, p. 2454-8.
Non Patent Literature 6: Garcia, M. A. et al., Synthesis, biological evaluation, and three-dimensional quantitative structure-activity relationship study of small-molecule positive modulators of adrenomedullin. J Med Chem, 2005, Volume 48, Issue 12, p. 4068-75.
Non Patent Literature 7: Mitsuda, Y. et al., Large-scale production of functional human adrenomedullin: expression, cleavage, amidation, and purification. Protein Expr Purif, 2002, Volume 25, Issue 3, p. 448-55.
Non Patent Literature 8: Roldos, V. et al., Small-molecule negative modulators of adrenomedullin: design, synthesis, and 3D-QSAR study. ChemMedChem, 2008, Volume 3, Issue 9, p. 1345-55.
Non Patent Literature 9: Watanabe, T. X. et al., Vasopressor activities of N-terminal fragments of adrenomedullin in anesthetized rat. Biochem Biophys Res Commun, 1996, Volume 219, Issue 1, p. 59-63.

Non Patent Literature 10: Kubo, K et al., Biological properties of adrenomedullin conjugated with polyethylene glycol. Peptides, 2014, Volume 57, p. 118-21.

Non Patent Literature 11: Kato, J., Kitamura, K. Bench-to-bedside pharmacology of adrenomedullin. European Journal of Pharmacology, 2015, Volume 764, p. 140-148.

SUMMARY OF INVENTION

Technical Problem

As described above, AM derivatives in which other groups such as a PEG group are linked to AM are known in order to improve the pharmacokinetics of AM from the viewpoint of improvement in sustainability in a living body. However, known AM derivatives are susceptible to improvement. For example, in the case of linking a relatively large group such as a PEG group to a relatively small peptide such as AM, various properties of the resulting AM derivative may vary largely depending on the molecular weight of the PEG group. As described in Patent Literatures 4 and 5 and Non Patent Literature 10, when a peptide moiety and other groups are linked through a bond which may be cleaved by a biological reaction, such as an amide bond or an ester bond, the bond may be cleaved in a relatively short time after administration. As in the AM derivative described in Patent Literature 5, in the case of linking other groups to the side chain of an amino acid residue of AM, the conformation of the AM moiety may be changed to reduce the affinity for an AM receptor recognizing AM. In such a case, pharmacological effects as AM of the resulting AM derivative may be reduced.

AM has a strong vasodilatory effect, in addition to pharmacological effects such as a cardiovascular protective effect, an anti-inflammatory effect, an angiogenic effect, and a tissue repair promoting effect. This strong vasodilatory effect may cause unwanted side effects such as excessive decreased blood pressure when AM or an AM derivative is administered to subjects. The occurrence of such side effects may become a problem when AM or an AM derivative is used, particularly, in the expectation that pharmacological effects other than a vasodilatory effect are exerted.

The invention, therefore, is intended to provide novel adrenomedullin derivatives sustainable for a long period which are capable of substantially suppressing unwanted side effects while maintaining pharmacological effects of adrenomedullin.

Solution to Problem

The present inventors conducted various investigations of means to solve the problems described above. The present inventors have found that linking of the N-terminal α-amino group of adrenomedullin to a PEG group with a specific molecular weight via a methylene group or a urethane group can prolong blood half-life of the resulting adrenomedullin derivative as compared to adrenomedullin while retaining bioactivity at the same level as in adrenomedullin. Furthermore, the present inventors have found that novel adrenomedullin derivatives having the properties described above are capable of substantially suppressing unwanted side effects such as excessive decreased blood pressure. The present inventors have achieved the invention based on the finding described above.

That is to say, a summary of the invention is as the following:

(1) A compound represented by formula (I):

wherein
A is a modifying group comprising one or more polyethylene glycol groups, and
B is a peptide moiety derived from adrenomedullin or a modified form thereof with adrenomedullin activity,
wherein the peptide moiety B is linked to the other moieties through a covalent bond of the nitrogen atom of the N-terminal α-amino group of the peptide moiety B to the carbon atom of the methylene group,
or a salt thereof, or a hydrate thereof.

(2) The compound according to the embodiment (1), wherein A is a modifying group represented by the following formula (II):

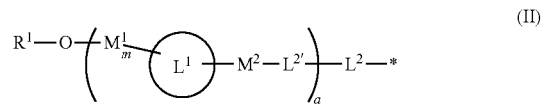

wherein
a is an integer of 1 or larger,
m is an integer of 1 or larger,
$L^1$ is a m+1-valent linear or branched linking group, wherein when a plurality of $L^1$ are present, the plurality of $L^1$ are the same as or different from each other,
$L^2$ and $L^{2'}$ are each independently a bond or a divalent linking group, wherein when a plurality of $L^{2'}$ are present, the plurality of $L^{2'}$ are the same as or different from each other,
$M^1$ is a polyethylene glycol group represented by formula (III):

wherein
n is an integer of 1 or larger,
* is a binding position to $L^1$, and
# is a binding position to O or $L^{2'}$,
wherein when a plurality of $M^1$ are present, the plurality of $M^1$ are the same as or different from each other,
$M^2$ is a bond or a polyethylene glycol group represented by formula (III), wherein when a plurality of $M^2$ are present, the plurality of $M^2$ are the same as or different from each other,
$R^1$ is hydrogen, substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_4$-$C_{20}$ cycloalkenyl, substituted or unsubstituted $C_4$-$C_{20}$ cycloalkynyl, substituted or unsubstituted 3- to 6-membered heterocycloalkyl, substituted or unsubstituted $C_7$-$C_{20}$ cycloalkylalkyl, substituted or unsubstituted 3- to 6-membered heterocycloalkyl-$C_1$-$C_{20}$ alkyl, substituted or unsubstituted $C_4$-$C_{20}$ aryl, substituted or unsubstituted $C_5$-$C_{20}$ arylalkyl, substituted or unsubstituted 5- to 15-membered heteroaryl, substituted or unsubstituted 5- to 15-membered heteroaryl-$C_1$-$C_{20}$ alkyl, or substituted or unsubstituted acyl, and
is a binding position to the other moieties.

(3) The compound according to the embodiment (1) or (2), wherein A is a modifying group represented by the following formula (V), (VI), (VII) or (VIII):

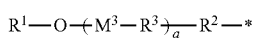

(V)

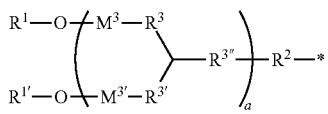

(VI)

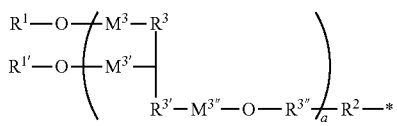

(VII)

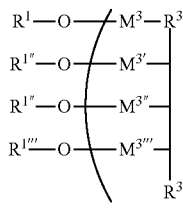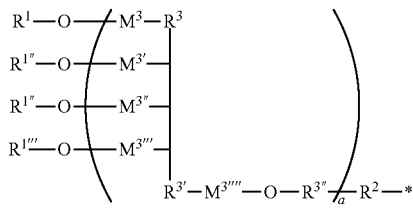

(VIII)

wherein
a is an integer of 1 or larger,
$M^3$, $M^{3'}$, $M^{3''}$, $M^{3'''}$ and $M^{3''''}$ are each independently a bond or a polyethylene glycol group represented by formula (III):

  (III)

wherein
n is an integer of 1 or larger,
* is a binding position to $R^3$, $R^{3'}$ or CH, and
# is a binding position to O,
wherein when a plurality of $M^3$, $M^{3'}$, $M^{3''}$, $M^{3'''}$ or $M^{3''''}$ are present, the plurality of $M^3$, $M^{3'}$, $M^{3''}$, $M^{3'''}$ or $M^{3''''}$ are the same as or different from each other, and at least one of $M^3$, $M^{3'}$, $M^{3''}$, $M^{3'''}$ and $M^{3''''}$ is a polyethylene glycol group represented by formula (III),
$R^1$, $R^{1'}$, $R^{1''}$ and $R^{1'''}$ are each independently hydrogen, substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_4$-$C_{20}$ cycloalkenyl, substituted or unsubstituted $C_4$-$C_{20}$ cycloalkynyl, substituted or unsubstituted 3- to 6-membered heterocycloalkyl, substituted or unsubstituted $C_7$-$C_{20}$ cycloalkylalkyl, substituted or unsubstituted 3- to 6-membered heterocycloalkyl-$C_1$-$C_{20}$ alkyl, substituted or unsubstituted $C_4$-$C_{20}$ aryl, substituted or unsubstituted $C_5$-$C_{20}$ arylalkyl, substituted or unsubstituted 5- to 15-membered heteroaryl, substituted or unsubstituted 5- to 15-membered heteroaryl-$C_1$-$C_{20}$ alkyl, or substituted or unsubstituted acyl,
$R^2$ is a bond, substituted or unsubstituted $C_1$-$C_{20}$ alkylene, substituted or unsubstituted $C_2$-$C_{20}$ alkenylene, substituted or unsubstituted $C_2$-$C_{20}$ alkynylene, substituted or unsubstituted $C_3$-$C_{20}$ cycloalkylene, substituted or unsubstituted $C_4$-$C_{20}$ cycloalkenylene, substituted or unsubstituted $C_4$-$C_{20}$ cycloalkynylene, substituted or unsubstituted 3- to 6-membered heterocycloalkylene, substituted or unsubstituted $C_7$-$C_{20}$ cycloalkylalkylene, substituted or unsubstituted 3- to 6-membered heterocycloalkyl-$C_1$-$C_{20}$ alkylene, substituted or unsubstituted $C_4$-$C_{20}$ arylene, substituted or unsubstituted $C_5$-$C_{20}$ arylalkylene, substituted or unsubstituted 5- to 15-membered heteroarylene, or substituted or unsubstituted 5- to 15-membered heteroaryl-$C_1$-$C_{20}$ alkylene (the groups optionally comprise one or more heteroatoms, an amide group (—CO—NH—), an ester group (—CO—O—), or a urethane group (—O—CO—NH—)), an amide group (—CO—NH—), an ester group (—CO—O—), or a urethane group (—O—CO—NH—), $R^3$, $R^{3'}$ and $R^{3''}$ are each independently a bond, substituted or unsubstituted $C_1$-$C_{20}$ alkylene, substituted or unsubstituted $C_2$-$C_{20}$ alkenylene, substituted or unsubstituted $C_2$-$C_{20}$ alkynylene, substituted or unsubstituted $C_3$-$C_{20}$ cycloalkylene, substituted or unsubstituted $C_4$-$C_{20}$ cycloalkenylene, substituted or unsubstituted $C_4$-$C_{20}$ cycloalkynylene, substituted or unsubstituted 3- to 6-membered heterocycloalkylene, substituted or unsubstituted $C_7$-$C_{20}$ cycloalkylalkylene, substituted or unsubstituted 3- to 6-membered heterocycloalkyl-$C_1$-$C_{20}$ alkylene, substituted or unsubstituted $C_4$-$C_{20}$ arylene, substituted or unsubstituted $C_5$-$C_{20}$ arylalkylene, substituted or unsubstituted 5- to 15-membered heteroarylene, or substituted or unsubstituted 5- to 15-membered heteroaryl-$C_1$-$C_{20}$ alkylene (the groups optionally comprise one or more heteroatoms, an amide group (—CO—NH—), an ester group (—CO—O—), or a urethane group (—O—CO—NH—)), an amide group (—CO—NH—), an ester group (—CO—O—), or a urethane group (—O—CO—NH—), wherein when a plurality of $R^3$, $R^{3'}$ or $R^{3''}$ are present, the plurality of $R^3$, $R^{3'}$ or $R^{3''}$ are the same as or different from each other, and
is a binding position to the other moieties.

(4) The compound according to any of the embodiments (1) to (3), wherein the polyethylene glycol group represented by formula (III) has a weight-average molecular weight ranging from 1 to 100 kDa in total.

(5) The compound according to any of the embodiments (1) to (4), wherein the adrenomedullin or the modified form thereof with adrenomedullin activity is a peptide selected from the group consisting of:
(i) a peptide consisting of an amino acid sequence of adrenomedullin,
(ii) a peptide that consists of an amino acid sequence of adrenomedullin and has a disulfide bond formed by two cysteine residues in the amino acid sequence,
(iii) the peptide of (ii) wherein the disulfide bond of the peptide is substituted with an ethylene group and the peptide has adrenomedullin activity,
(iv) any peptide of (i) to (iii) wherein the peptide has the amino acid sequence comprising deletion, substitution, or addition of one to fifteen amino acid residues and has adrenomedullin activity,
(v) any peptide of (i) to (iv) wherein the peptide is amidated at the C-terminus thereof, and
(vi) any peptide of (i) to (iv) wherein the peptide has a glycine residue added to the C-terminus thereof.

(6) The compound according to the embodiment (5), wherein the adrenomedullin or the modified form thereof is a peptide selected from the group consisting of:
(i) a peptide consisting of an amino acid sequence of adrenomedullin,
(ii) a peptide that consists of an amino acid sequence of adrenomedullin and has a disulfide bond formed by two cysteine residues in the amino acid sequence,
(v) the peptide of (i) or (ii) wherein the peptide is amidated at the C-terminus thereof, and (vi) the peptide of (i) or (ii) wherein the peptide has a glycine residue added to the C-terminus thereof.

(7) The compound according to the embodiment (5), wherein the adrenomedullin or the modified form thereof is a peptide selected from the group consisting of:
- (iv') any peptide of (i) to (iii) wherein the peptide has deletion of amino acid residues at positions 1 to 15, positions 1 to 10, or positions 1 to 5 from the N-terminus thereof and has adrenomedullin activity,
- (v) the peptide of (iv') wherein the peptide is amidated at the C-terminus thereof, and
- (vi) the peptide of (iv') wherein the peptide has a glycine residue added to the C-terminus thereof.

(8) The compound according to any of the embodiments (1) to (5), wherein the adrenomedullin or the modified form thereof is a peptide selected from the group consisting of:
- (a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
- (b) a peptide consisting of the amino acid sequence of SEQ ID NO: 3, or a peptide consisting of the amino acid sequence of SEQ ID NO: 3 and having a disulfide bond formed by the cysteine residues at positions 16 and 21;
- (c) a peptide consisting of the amino acid sequence of SEQ ID NO: 5, or a peptide consisting of the amino acid sequence of SEQ ID NO: 5 and having a disulfide bond formed by the cysteine residues at positions 16 and 21;
- (d) a peptide consisting of the amino acid sequence of SEQ ID NO: 7, or a peptide consisting of the amino acid sequence of SEQ ID NO: 7 and having a disulfide bond formed by the cysteine residues at positions 16 and 21;
- (e) a peptide consisting of the amino acid sequence of SEQ ID NO: 9, or a peptide consisting of the amino acid sequence of SEQ ID NO: 9 and having a disulfide bond formed by the cysteine residues at positions 14 and 19;
- (f) a peptide consisting of the amino acid sequence of SEQ ID NO: 11, or a peptide consisting of the amino acid sequence of SEQ ID NO: 11 and having a disulfide bond formed by the cysteine residues at positions 14 and 19;
- (g) any peptide of (a) to (f) wherein the disulfide bond of the peptide is substituted with an ethylene group and the peptide has adrenomedullin activity;
- (h) any peptide of (a) to (g) wherein the peptide has the amino acid sequence comprising deletion, substitution, or addition of one to fifteen amino acids and has adrenomedullin activity;
- (i) any peptide of (a) to (h) wherein the peptide is amidated at the C-terminus thereof; and
- (j) any peptide of (a) to (h) wherein the peptide has a glycine residue added to the C-terminus thereof.

(9) The compound according to the embodiment (8), wherein the adrenomedullin or the modified form thereof is a peptide selected from the group consisting of:
- (a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
- (b) a peptide consisting of the amino acid sequence of SEQ ID NO: 3, or a peptide consisting of the amino acid sequence of SEQ ID NO: 3 and having a disulfide bond formed by the cysteine residues at positions 16 and 21;
- (c) a peptide consisting of the amino acid sequence of SEQ ID NO: 5, or a peptide consisting of the amino acid sequence of SEQ ID NO: 5 and having a disulfide bond formed by the cysteine residues at positions 16 and 21;
- (d) a peptide consisting of the amino acid sequence of SEQ ID NO: 7, or a peptide consisting of the amino acid sequence of SEQ ID NO: 7 and having a disulfide bond formed by the cysteine residues at positions 16 and 21;
- (e) a peptide consisting of the amino acid sequence of SEQ ID NO: 9, or a peptide consisting of the amino acid sequence of SEQ ID NO: 9 and having a disulfide bond formed by the cysteine residues at positions 14 and 19;
- (f) a peptide consisting of the amino acid sequence of SEQ ID NO: 11, or a peptide consisting of the amino acid sequence of SEQ ID NO: 11 and having a disulfide bond formed by the cysteine residues at positions 14 and 19;
- (i) any peptide of (a) to (f) wherein the peptide is amidated at the C-terminus thereof; and
- (j) any peptide of (a) to (f) wherein the peptide has a glycine residue added to the C-terminus thereof.

(10) The compound according to the embodiment (8), wherein the adrenomedullin or the modified form thereof is a peptide selected from the group consisting of:
- (h') any peptide of (a) to (d) wherein the peptide has deletion of amino acid residues at positions 1 to 15, positions 1 to 10, or positions 1 to 5 from the N-terminus thereof and has adrenomedullin activity, or the peptide of (e) or (f) wherein the peptide has deletion of amino acid residues at positions 1 to 13, positions 1 to 8, or positions 1 to 5 from the N-terminus thereof and has adrenomedullin activity;
- (i) the peptide of (h') wherein the peptide is amidated at the C-terminus thereof; and
- (j) the peptide of (h') wherein the peptide has a glycine residue added to the C-terminus thereof.

(11) A method for producing the compound according to any of the embodiments (1) to (10) or a salt thereof, or a hydrate thereof, comprising a linking step of reacting a precursor of peptide moiety B derived from adrenomedullin or a modified form thereof with a precursor aldehyde of modifying group A comprising one or more polyethylene glycol groups in the presence of a reducing agent to form the compound represented by formula (I), wherein the precursor aldehyde is represented by formula (I-1):

    (I-1).

(12) A compound represented by formula (X):

    (X)

wherein
- A' is a modifying group comprising one or more polyethylene glycol groups, and
- B is a peptide moiety derived from adrenomedullin or a modified form thereof with adrenomedullin activity,
- wherein the peptide moiety B is linked to the other moieties through a covalent bond of the nitrogen atom of the N-terminal α-amino group of the peptide moiety B to the carbon atom of the carbonyl group, A' is a modifying group represented by the following formula (XI), (XI') or (XII):

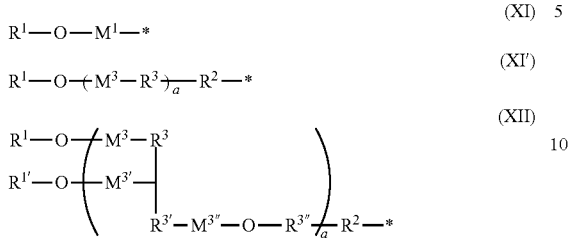

wherein
a is an integer of 1 or larger,
$M^1$ is a polyethylene glycol group represented by formula (III):

wherein
n is an integer of 1 or larger,
\* is a binding position to \*, and
\# is a binding position to O,
$M^3$, $M^{3'}$ and $M^{3''}$ are each independently a bond or a polyethylene glycol group represented by formula (III):

wherein
n is an integer of 1 or larger,
\* is a binding position to $R^3$, $R^{3'}$ or CH, and
\# is a binding position to O,
wherein when a plurality of $M^3$, $M^{3'}$ or $M^{3''}$ are present, the plurality of $M^3$, $M^{3'}$ or $M^{3''}$ are the same as or different from each other, and at least one of $M^3$, $M^{3'}$ and $M^{3''}$ is a polyethylene glycol group represented by formula (III),
$R^1$ and $R^{1'}$ are each independently hydrogen, substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_4$-$C_{20}$ cycloalkenyl, substituted or unsubstituted $C_4$-$C_{20}$ cycloalkynyl, substituted or unsubstituted 3- to 6-membered heterocycloalkyl, substituted or unsubstituted $C_7$-$C_{20}$ cycloalkylalkyl, substituted or unsubstituted 3- to 6-membered heterocycloalkyl-$C_1$-$C_{20}$ alkyl, substituted or unsubstituted $C_4$-$C_{20}$ aryl, substituted or unsubstituted $C_5$-$C_{20}$ arylalkyl, substituted or unsubstituted 5- to 15-membered heteroaryl, substituted or unsubstituted 5- to 15-membered heteroaryl-$C_1$-$C_{20}$ alkyl, or substituted or unsubstituted acyl,
$R^2$ is a bond, substituted or unsubstituted $C_1$-$C_{20}$ alkylene, substituted or unsubstituted $C_2$-$C_{20}$ alkenylene, substituted or unsubstituted $C_2$-$C_{20}$ alkynylene, substituted or unsubstituted $C_3$-$C_{20}$ cycloalkylene, substituted or unsubstituted $C_4$-$C_{20}$ cycloalkenylene, substituted or unsubstituted $C_4$-$C_{20}$ cycloalkynylene, substituted or unsubstituted 3- to 6-membered heterocycloalkylene, substituted or unsubstituted $C_7$-$C_{20}$ cycloalkylalkylene, substituted or unsubstituted 3- to 6-membered heterocycloalkyl-$C_1$-$C_{20}$ alkylene, substituted or unsubstituted $C_4$-$C_{20}$ arylene, substituted or unsubstituted $C_5$-$C_{20}$ arylalkylene, substituted or unsubstituted 5- to 15-membered heteroarylene, or substituted or unsubstituted 5- to 15-membered heteroaryl-$C_1$-$C_{20}$ alkylene (the groups optionally comprise one or more heteroatoms, an amide group (—CO—NH—), an ester group (—CO—O—), or a urethane group (—O—CO—NH—)), an amide group (—CO—NH—), an ester group (—CO—O—), or a urethane group (—O—CO—NH—),
$R^3$, $R^{3'}$ and $R^{3''}$ are each independently a bond, substituted or unsubstituted $C_1$-$C_{20}$ alkylene, substituted or unsubstituted $C_2$-$C_{20}$ alkenylene, substituted or unsubstituted $C_2$-$C_{20}$ alkynylene, substituted or unsubstituted $C_3$-$C_{20}$ cycloalkylene, substituted or unsubstituted $C_4$-$C_{20}$ cycloalkenylene, substituted or unsubstituted $C_4$-$C_{20}$ cycloalkynylene, substituted or unsubstituted 3- to 6-membered heterocycloalkylene, substituted or unsubstituted $C_7$-$C_{20}$ cycloalkylalkylene, substituted or unsubstituted 3- to 6-membered heterocycloalkyl-$C_1$-$C_{20}$ alkylene, substituted or unsubstituted $C_4$-$C_{20}$ arylene, substituted or unsubstituted $C_5$-$C_{20}$ arylalkylene, substituted or unsubstituted 5- to 15-membered heteroarylene, or substituted or unsubstituted 5- to 15-membered heteroaryl-$C_1$-$C_{20}$ alkylene (the groups optionally comprise one or more heteroatoms, an amide group (—CO—NH—), an ester group (—CO—O—), or a urethane group (—O—CO—NH—)), an amide group (—CO—NH—), an ester group (—CO—O—), or a urethane group (—O—CO—NH—), wherein when a plurality of $R^3$, $R^{3'}$ or $R^{3''}$ are present, the plurality of $R^3$, $R^{3'}$ or $R^{3''}$ are the same as or different from each other, and
\* is a binding position to the other moieties,
or a salt thereof, or a hydrate thereof.

(13) A medicament comprising the compound according to any of the embodiments (1) to (10) and (12) or a pharmaceutically acceptable salt thereof, or a pharmaceutically acceptable hydrate thereof as an active ingredient.

(14) The medicament according to the embodiment (13) for use in the prevention or treatment of a cardiovascular disease, an inflammatory disease, or a peripheral vascular disease.

(15) An agent for preventing or treating a cardiovascular disease, an inflammatory disease, or a peripheral vascular disease, wherein the agent comprises the compound according to any of the embodiments (1) to (10) and (12) or a pharmaceutically acceptable salt thereof, or a pharmaceutically acceptable hydrate thereof as an active ingredient.

(16) A pharmaceutical composition comprising the compound according to any of the embodiments (1) to (10) and (12) or a pharmaceutically acceptable salt thereof, or a pharmaceutically acceptable hydrate thereof and one or more pharmaceutically acceptable carriers.

(17) The pharmaceutical composition according to the embodiment (16) for use in the prevention or treatment of a cardiovascular disease, an inflammatory disease, or a peripheral vascular disease.

(18) A method for preventing or treating a condition, disease, and/or disorder, comprising administering to a subject in need of prevention or treatment of the condition, disease, and/or disorder an effective amount of the compound according to any of the embodiments (1) to (10) and (12) or a pharmaceutically acceptable salt thereof, or a pharmaceutically acceptable hydrate thereof.

(19) The method according to the embodiment (18) wherein the condition, disease, and/or disorder is a cardiovascular disease, an inflammatory disease, or a peripheral vascular disease.

(20) The compound according to any of the embodiments (1) to (10) and (12) or a pharmaceutically acceptable salt thereof, or a pharmaceutically acceptable hydrate thereof for use in the prevention or treatment of a condition, disease, and/or disorder.

(21) The compound according to the embodiment (20) wherein the condition, disease, and/or disorder is a cardiovascular disease, an inflammatory disease, or a peripheral vascular disease.

(22) Use of the compound according to any of the embodiments (1) to (10) and (12) or a pharmaceutically acceptable salt thereof, or a pharmaceutically acceptable hydrate thereof for manufacturing a medicament for the prevention or treatment of a condition, disease, and/or disorder.

(23) The use according to the embodiment (22) wherein the condition, disease, and/or disorder is a cardiovascular disease, an inflammatory disease, or a peripheral vascular disease.

Advantageous Effects of Invention

The invention can provide novel adrenomedullin derivatives sustainable for a long period which are capable of substantially suppressing unwanted side effects while maintaining pharmacological effects of adrenomedullin.

The present specification includes contents described in the specification and/or drawings of Japanese patent application No. 2015-184685 to which the present application claims priority.

DESCRIPTION OF EMBODIMENTS

<1. Adrenomedullin Derivative>

Figure 1:
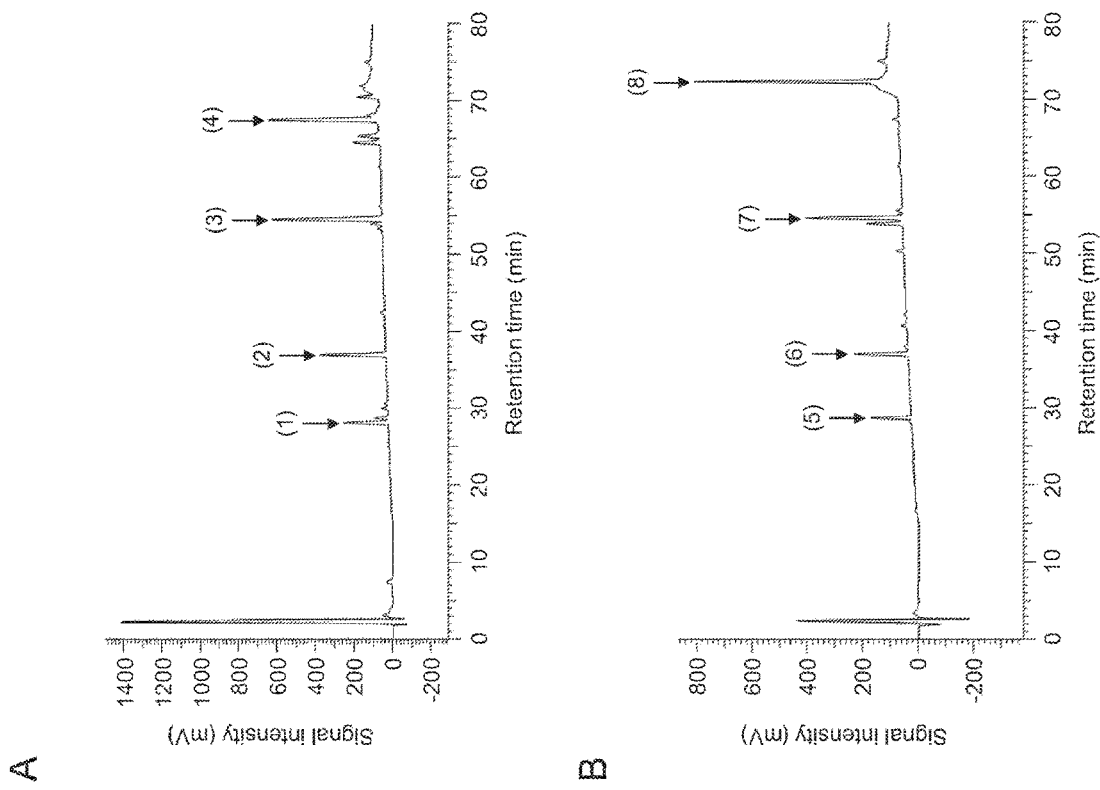
FIG. 1 shows reverse-phase HPLC (RP-HPLC) chromatograms of cleaved peptides. A: RP-HPLC chromatogram of a cleaved peptide derived from h.AM (1-52) peptide; and B: RP-HPLC chromatogram of a cleaved peptide derived from compound (2).

An aspect of the invention relates to a compound represented by formula (I):

$$A\text{-}CH_2\text{—}B \qquad (I)$$

or a salt thereof, or a hydrate thereof. In the present specification, the compound represented by formula (I) may be described as "adrenomedullin derivative".

In the invention, adrenomedullin (AM) may not only be a peptide derived from human and isolated and identified from human pheochromocytoma (SEQ ID NO: 1, Non Patent Literature 1), but also be a peptide derived from other non-human mammals (such as warm-blooded animals), which is an ortholog, including, for example, pig (SEQ ID NO: 3), dog (SEQ ID NO: 5), cattle (SEQ ID NO: 7), rat (SEQ ID NO: 9), or mouse (SEQ ID NO: 11). In a living body, each of these peptides has a disulfide bond formed by two cysteine residues in the amino acid sequence and is amidated at the C-terminus thereof. In the present specification, the peptide having a disulfide bond and C-terminal amide group may be described as "natural adrenomedullin" or simply "adrenomedullin". The invention can be applied to any of the peptides described above.

In the present specification, "C-terminal amidation" means an aspect of post-translational modification of a peptide in a living body, and specifically means a reaction in which the main chain carboxyl group of C-terminal amino acid residue of the peptide is converted into an amide group. In the present specification, "formation of a disulfide bond between cysteine residues" or "disulfide bond formation by cysteine residues" means an aspect of post-translational modification of the peptide in a living body, and specifically means a reaction in which two cysteine residues in the amino acid sequence of the peptide form a disulfide bond (—S—S—). Many bioactive peptides produced in a living body are initially biosynthesized as a precursor protein with larger molecular weight. The precursor protein is subject to post-translational modifications, such as C-terminal amidation and/or disulfide bond formation by cysteine residues, during the process of intracellular transport to give a mature bioactive peptide. The C-terminal amidation typically proceeds by a C-terminal amidating enzyme that acts on the precursor protein. For a bioactive peptide having a C-terminal amide group, the precursor protein has a Gly residue bound to the C-terminal carboxyl group to be amidated and the Gly residue is converted into the C-terminal amide group by the C-terminal amidating enzyme. The C-terminal propeptide in the precursor protein has a repeat sequence comprising a combination of basic amino acid residues, such as Lys-Arg or Arg-Arg (Mizuno, Journal of Japanese Biochemical Society, 61(12): 1435-1461 (1989)). Disulfide bond formation by cysteine residues can proceed under oxidative conditions. Disulfide bond formation by cysteine residues in a living body typically proceeds by a protein disulfide isomerase that acts on the precursor protein.

Adrenomedullin, a known bioactive substance, is a peptide. This may cause a medicament comprising adrenomedullin as an active ingredient to act effectively in living bodies in subjects (such as human patients) only for a very short time. Accordingly, attempts have been made to prolong half-life in a living body and improve pharmacokinetics by means of forms of adrenomedullin derivatives in which other groups such as polyethylene glycol (PEG) are linked to adrenomedullin (Patent Literatures 4 to 6 and Non Patent Literature 10). However, in the case of linking a relatively large group such as a PEG group to a relatively small peptide such as adrenomedullin, various properties of the resulting adrenomedullin derivative may vary largely depending on the molecular weight of the PEG group. When adrenomedullin and other groups are linked through a bond, such as an amide bond or an ester bond, which may be cleaved by a biological reaction, the bond may be cleaved in a relatively short time after administration. In the case of linking other groups to the side chain of an amino acid residue of adrenomedullin, the conformation of the adrenomedullin moiety may be changed to reduce the affinity for an AM receptor recognizing adrenomedullin. In such a case, pharmacological effects as adrenomedullin of the resulting adrenomedullin derivative may be reduced.

Adrenomedullin has a strong vasodilatory effect. This strong vasodilatory effect may cause unwanted side effects (such as excessive decreased blood pressure, tachycardia associated with increased reflex sympathetic nerve activity, and/or increased activity of renin) when a therapeutically effective amount of adrenomedullin or a derivative thereof is administered in a single dose. The occurrence of such side effects may become a problem when adrenomedullin or a derivative thereof is used, particularly, in the expectation that pharmacological effects other than a vasodilatory effect are exerted. To avoid generating the problems described above, a medicament comprising adrenomedullin or a derivative thereof as an active ingredient is required to be administered to subjects via continuous intravenous infusion. Such a mode of administration may force subjects to bear an undue burden.

The present inventors have found that linking of the N-terminal α-amino group of adrenomedullin to a PEG group with a specific molecular weight via a methylene group or a urethane group can prolong blood half-life of the resulting adrenomedullin derivative as compared to adrenomedullin while retaining bioactivity of adrenomedullin. The present inventors have further found that novel adrenomedullin derivatives having the properties described above are capable of substantially suppressing unwanted side effects such as excessive decreased blood pressure. Thus, the compound of the invention represented by formula (I) can be applied to a condition, disease, and/or disorder that can be prevented or treated with adrenomedullin to sustainably prevent or treat the condition, disease, and/or disorder while substantially suppressing unwanted side effects.

In the formula (I), B is required to be a peptide moiety derived from adrenomedullin or a modified form thereof with adrenomedullin activity. In the invention, "peptide moiety derived from adrenomedullin or a modified form thereof with adrenomedullin activity" means a monovalent free group with a structure derived from adrenomedullin or the modified form thereof with adrenomedullin activity by removal of one hydrogen atom (commonly, one hydrogen atom of an amino group, typically one hydrogen atom of the N-terminal α-amino group). In the invention, "a modified form of adrenomedullin" means a peptide chemically modified from natural adrenomedullin as described above. In the invention, "adrenomedullin activity" means bioactivity that adrenomedullin has. The adrenomedullin activity can include the following:

(1) Cardiovascular: a vasodilatory effect, an effect of lowering blood pressure, an effect of suppressing increase in blood pressure, an effect of increasing cardiac output or improving cardiac insufficiency, an effect of improving pulmonary hypertension, an angiogenic effect, a lymphangiogenic effect, an effect of improving vascular endothelial function, an antiarteriosclerotic effect, a myocardial protective effect (such as a myocardial protective effect in ischemic reperfusion disorder or inflammation), an effect of preventing postmyocardial remodeling, an effect of suppressing cardiac hypertrophy, and an effect of suppressing an angiotensin-converting enzyme.

(2) Kidney and water and electrolyte system: a diuretic effect, a natriuretic effect, an effect of suppressing antidiuretic hormone, an aldosterone-reducing effect, a renoprotective effect (such as a renoprotective effect in high blood pressure or ischemic reperfusion disorder), an effect of suppressing drinking behavior, and an effect of suppressing salt requirement.

(3) Brain and nervous system: an effect of neuroprotection and preventing encephalopathy, an anti-inflammatory effect, an effect of suppressing apoptosis (such as an effect of suppressing apoptosis in ischemic reperfusion disorder or inflammation), an effect of maintaining autoregulatory capacity, an effect of suppressing oxidative stress, an effect of improving dementia, and a sympathoinhibitory effect.

(4) Urogenital: an effect of improving erection, an effect of improving blood flow, and an implantation-promoting effect.

(5) Gastrointestinal system: an antiulcer effect, a tissue repair effect, an effect of neogenesis of mucous membrane, an effect of improving blood flow, an anti-inflammatory effect, and an effect of improving liver function.

(6) Orthopedics: an effect of stimulating osteoblast and an effect of improving arthritis.

(7) Endocrine metabolic system: an adipocyte-differentiating effect, an effect of regulating lipolysis, an effect of improving insulin sensitivity, an effect of controlling insulin secretion, an effect of suppressing antidiuretic hormone secretion, and an effect of suppressing aldosterone secretion.

(8) Other: an effect of improving circulation, an anti-inflammatory effect, an effect of modulating cytokine, an organ protective effect, an effect of suppressing oxidative stress, an effect of repairing tissue (such as an anti-decubitus effect), an effect of improving septic shock, an effect of suppressing multiple organ failure, an effect of suppressing auto-immune disease, an antimicrobial effect, a hair growth effect, and a pilatory effect.

The blood pressure-lowering effect is preferably a vasodilatory hypotensive effect. The anti-inflammatory effect in the gastrointestinal system is preferably an effect of preventing or treating inflammatory bowel diseases including a steroid-resistant or steroid-dependent inflammatory bowel disease (such as ulcerative colitis, Crohn's disease, or intestinal tract Behcet's disease). The adrenomedullin activity will be exerted via increased concentration of intracellular cAMP. Thus, the increased concentration of intracellular cAMP can be considered as an index of adrenomedullin activity. The peptide moiety B derived from adrenomedullin or a modified form thereof having the bioactivity as described above enables the compound of the invention represented by formula (I) to exert bioactivity substantially approximately equivalent to that of natural adrenomedullin (i.e., adrenomedullin activity).

The adrenomedullin or a modified form thereof with adrenomedullin activity is preferably a peptide selected from the group consisting of:
(i) a peptide consisting of an amino acid sequence of adrenomedullin,
(ii) a peptide that consists of an amino acid sequence of adrenomedullin and has a disulfide bond formed by two cysteine residues in the amino acid sequence,
(iii) the peptide of (ii) wherein the disulfide bond of the peptide is substituted with an ethylene group and the peptide has adrenomedullin activity,
(iv) any peptide of (i) to (iii) wherein the peptide has the amino acid sequence comprising deletion, substitution, or addition of one to fifteen amino acids and has adrenomedullin activity,
(v) any peptide of (i) to (iv) wherein the peptide is amidated at the C-terminus thereof, and
(vi) any peptide of (i) to (iv) wherein the peptide has a glycine residue added to the C-terminus thereof.

In one embodiment, the adrenomedullin or a modified form thereof with adrenomedullin activity is more preferably a peptide selected from the group consisting of:
(i) a peptide consisting of an amino acid sequence of adrenomedullin,
(ii) a peptide that consists of an amino acid sequence of adrenomedullin and has a disulfide bond formed by two cysteine residues in the amino acid sequence,
(v) the peptide of (i) or (ii) wherein the peptide is amidated at the C-terminus thereof, and
(vi) the peptide of (i) or (ii) wherein the peptide has a glycine residue added to the C-terminus thereof.

In another embodiment, the adrenomedullin or a modified form thereof with adrenomedullin activity is more preferably a peptide selected from the group consisting of:
(iv') any peptide of (i) to (iii) wherein the peptide has deletion of amino acid residues at positions 1 to 15, positions 1 to 10, or positions 1 to 5 from the N-terminus thereof and has adrenomedullin activity,
(v) the peptide of (iv') wherein the peptide is amidated at the C-terminus thereof, and
(vi) the peptide of (iv') wherein the peptide has a glycine residue added to the C-terminus thereof.

In the peptides of (i) to (vi) and (iv'), a peptide involved in (v), which consists of the amino acid sequence of adrenomedullin, is amidated at the C-terminus thereof, and has a disulfide bond formed by two cysteine residues in the amino acid sequence, represents a mature natural adrenomedullin. A peptide of (i) consisting of an amino acid sequence of adrenomedullin represents a form (i.e., an immature form) of natural adrenomedullin prior to post-translational modification including C-terminal amidation and disulfide bond formation by cysteine residues. Other peptides except peptides described above in the peptides of (i) to (vi) and (iv') represent modified forms of adrenomedullin.

The peptide of (ii) can be formed by oxidizing thiol groups of two cysteine residues in the peptide of (i) with air or with a suitable oxidizing agent to form a disulfide bond. The peptide of (ii) can be used to establish the conformation of the peptide moiety B similar to that of natural adrenomedullin. This similar conformation can lead adrenomedullin activity of a compound represented by formula (I) to an activity substantially approximately equivalent to that of natural adrenomedullin.

The peptide of (iii) can be formed by converting the disulfide bond in the peptide of (ii) into an ethylene group. The substitution of the disulfide bond to an ethylene group can be accomplished by any method well known in the art (O. Keller et al., Helv. Chim. Acta, 1974, Volume 57, p. 1253). The peptide of (iii) can be used to stabilize the conformation of peptide moiety B. The stabilized conformation allows a compound represented by formula (I) to sustainably exert adrenomedullin activity in a living body.

In the peptide of (iv), the number of amino acid residues deleted, substituted, or added preferably ranges from 1 to 15, more preferably from 1 to 10, further preferably from 1 to 8, especially preferably from 1 to 5, and most preferably from 1 to 3. A suitable peptide of (iv) is any peptide of (i) to (iii) wherein the peptide has deletion of amino acid residues at positions 1 to 15, positions 1 to 12, positions 1 to 10, positions 1 to 8, positions 1 to 5, or positions 1 to 3 from the N-terminus thereof and has adrenomedullin activity. A more suitable peptide of (iv) is any peptide of (i) to (iii) wherein the peptide has deletion of amino acid residues at positions 1 to 15, positions 1 to 10, or positions 1 to 5 from the N-terminus thereof and has adrenomedullin activity (peptide of (iv')). The suitable peptide may have further deletion, substitution, or addition of one or more (such as 1 to 5, 1 to 3, or 1 or 2) amino acid residues.

The peptide of (iv) or (iv') can be used to achieve adrenomedullin activity of a compound represented by formula (I) substantially approximately equivalent to that of natural adrenomedullin. Also, the peptide of (iv) or (iv') can be used to sustainably exert adrenomedullin activity of a compound represented by formula (I) in a living body.

The peptide of (vi) or (iv') can be converted to the peptide of (v) by a C-terminal amidating enzyme which can convert a glycine residue at the C-terminus of the peptide of (vi) or (iv') into an amide group. Therefore, the peptide of (vi) or (iv') can be administered to a subject to form the peptide amidated at the C-terminus thereof in the living body of the subject after a certain period of time. Thus, a compound represented by formula (I) can sustainably exert adrenomedullin activity in a living body.

The adrenomedullin or a modified form thereof is more preferably a peptide selected from the group consisting of:
  (a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
  (b) a peptide consisting of the amino acid sequence of the SEQ ID NO: 3, or a peptide consisting of the amino acid sequence of the SEQ ID NO: 3 and having a disulfide bond formed by the cysteine residues at positions 16 and 21;
  (c) a peptide consisting of the amino acid sequence of SEQ ID NO: 5, or a peptide consisting of the amino acid sequence of SEQ ID NO: 5 and having a disulfide bond formed by the cysteine residues at positions 16 and 21;
  (d) a peptide consisting of the amino acid sequence of SEQ ID NO: 7, or a peptide consisting of the amino acid sequence of SEQ ID NO: 7 and having a disulfide bond formed by the cysteine residues at positions 16 and 21;
  (e) a peptide consisting of the amino acid sequence of SEQ ID NO: 9, or a peptide consisting of the amino acid sequence of SEQ ID NO: 9 and having a disulfide bond formed by the cysteine residues at positions 14 and 19;
  (f) a peptide consisting of the amino acid sequence of SEQ ID NO: 11, or a peptide consisting of the amino acid sequence of SEQ ID NO: 11 and having a disulfide bond formed by the cysteine residues at positions 14 and 19;
  (g) any peptide of (a) to (f) wherein the disulfide bond of the peptide is substituted with an ethylene group and the peptide has adrenomedullin activity;
  (h) any peptide of (a) to (g) wherein the peptide has the amino acid sequence comprising deletion, substitution, or addition of one to fifteen amino acids and has adrenomedullin activity;
  (i) any peptide of (a) to (h) wherein the peptide is amidated at the C-terminus thereof; and
  (j) any peptide of (a) to (h) wherein the peptide has a glycine residue added to the C-terminus thereof.

In one embodiment, the adrenomedullin or a modified form thereof is further preferably a peptide selected from the group consisting of:
  (a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
  (b) a peptide consisting of the amino acid sequence of SEQ ID NO: 3, or a peptide consisting of the amino acid sequence of SEQ ID NO: 3 and having a disulfide bond formed by the cysteine residues at positions 16 and 21;
  (c) a peptide consisting of the amino acid sequence of SEQ ID NO: 5, or a peptide consisting of the amino acid sequence of SEQ ID NO: 5 and having a disulfide bond formed by the cysteine residues at positions 16 and 21;
  (d) a peptide consisting of the amino acid sequence of SEQ ID NO: 7, or a peptide consisting of the amino acid sequence of SEQ ID NO: 7 and having a disulfide bond formed by the cysteine residues at positions 16 and 21;
  (e) a peptide consisting of the amino acid sequence of SEQ ID NO: 9, or a peptide consisting of the amino acid sequence of SEQ ID NO: 9 and having a disulfide bond formed by the cysteine residues at positions 14 and 19;
  (f) a peptide consisting of the amino acid sequence of SEQ ID NO: 11, or a peptide consisting of the amino acid sequence of SEQ ID NO: 11 and having a disulfide bond formed by the cysteine residues at positions 14 and 19;
  (i) any peptide of (a) to (f) wherein the peptide is amidated at the C-terminus thereof; and
  (j) any peptide of (a) to (f) wherein the peptide has a glycine residue added to the C-terminus thereof.

In another embodiment, the adrenomedullin or a modified form thereof is further preferably a peptide selected from the group consisting of:
  (h') any peptide of (a) to (d) wherein the peptide has deletion of amino acid residues at positions 1 to 15, positions 1 to 10, or positions 1 to 5 from the N-terminus thereof and has adrenomedullin activity, or the peptide of (e) or (f) wherein the peptide has deletion of amino acid residues at positions 1 to 13, positions 1 to 8, or positions 1 to 5 from the N-terminus thereof and has adrenomedullin activity;
  (i) the peptide of (h') wherein the peptide is amidated at the C-terminus thereof; and
  (j) the peptide of (h') wherein the peptide has a glycine residue added to the C-terminus thereof.

In the peptide of (h), the number of amino acid residues deleted, substituted, or added preferably ranges from 1 to 12, more preferably from 1 to 10, further preferably from 1 to 8, especially preferably from 1 to 5, and most preferably from 1 to 3. A suitable peptide of (h) is any peptide of (a) to (g) wherein the peptide has deletion of amino acid residues at positions 1 to 15, positions 1 to 12, positions 1 to 10, positions 1 to 8, positions 1 to 5, or positions 1 to 3 from the N-terminus thereof and has adrenomedullin activity. A more suitable peptide of (h) is any peptide of (a) to (d) wherein the peptide has deletion of amino acid residues at positions 1 to 15, positions 1 to 10, or positions 1 to 5 from the N-terminus thereof and has adrenomedullin activity, or the peptide of (e) or (f) wherein the peptide has deletion of amino acid residues at positions 1 to 13, positions 1 to 8, or positions 1 to 5 from the N-terminus thereof and has adrenomedullin activity (peptide of (h')). The suitable peptide may have further deletion, substitution, or addition of one or more (such as 1 to 5, 1 to 3, or 1 or 2) amino acids. The peptide of (h) or (h') can be used to achieve adrenomedullin activity of a compound represented by formula (I) substantially approximately equivalent to that of natural adrenomedullin. Also, the peptide of (h) or (h') can be used to sustainably exert adrenomedullin activity of a compound represented by formula (I) in a living body.

In the formula (I), A is required to be a modifying group comprising one or more PEG groups. An aspect of the modifying group A comprising one or more PEG groups is not particularly limited. For example, one or more PEG groups may be positioned at the terminal site of the modifying group A or may be positioned in the inside of the modifying group A. Also, the modifying group A may be various groups known in the art as PEG group-containing linear or branched groups. Known groups that can be used as the modifying group A can include, but are not limited to, for example, groups disclosed in WO1995/11924, WO2006/084089, WO98/41562, WO2005/079838, WO2002/060978, WO2001/048052, WO1998/055500, WO1996/021469, WO2003/040211, and JP Patent Publication (Kokai) No. 04-108827 A (1992). By use of a group comprising one or more PEG groups as the modifying group A, a compound represented by formula (I) can sustainably exert adrenomedullin activity in a living body.

A is preferably a modifying group represented by the following formula (II):

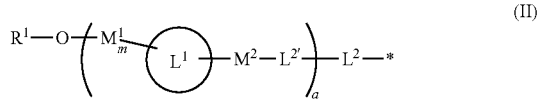

(II)

In the formula (II),
a is an integer of 1 or larger,
m is an integer of 1 or larger,
$L^1$ is a m+1-valent linear or branched linking group, wherein when a plurality of $L^1$ are present, the plurality of $L^1$ are the same as or different from each other,
$L^2$ and $L^{2'}$ are each independently a bond or a divalent linking group, wherein when a plurality of $L^{2'}$ are present, the plurality of $L^{2'}$ are the same as or different from each other,
$M^1$ is a PEG group, wherein when a plurality of $M^1$ are present, the plurality of $M^1$ are the same as or different from each other, $M^2$ is a bond or a PEG group, wherein when a plurality of $M^2$ are present, the plurality of $M^2$ are the same as or different from each other,
$R^1$ is hydrogen or a monovalent group, and
* is a binding position to the other moieties.

m is the number of branches of the linking group $L^1$. For example, when m is 1, $L^1$ is a divalent linking group and is a group non-branched toward the terminal directions, i.e., a linear group. When m is 2 or larger, $L^1$ is a trivalent or higher linking group and is a group having two or more branches toward the terminal directions. m is typically an integer of 1 or larger and 5 or smaller and preferably ranges from 1 to 5, more preferably from 1 to 4, and further preferably from 1 to 3. When the number m of branches of the linking group $L^1$ falls within the ranges described above, the modifying group A comprising PEG groups can have a linear or branched structure.

a is the number of repeats of a unit containing the PEG groups $M^1$ and $M^2$ and the linking groups $L^1$ and $L^{2'}$. For example, when a is 1, the unit has no repeat structure. When a is 2 or larger and m is 1, the unit has a linear repeat structure. When a is 2 or larger and m is 2 or larger, the unit has a dendritically branched repeat structure. a is typically an integer of 1 or larger and 5 or smaller and preferably ranges from 1 to 5 and more preferably from 1 to 2. The number a of repeats of the unit containing the PEG groups $M^1$ and $M^2$ and the linking groups $L^1$ and $L^{2'}$ falls within the ranges described above, the modifying group A comprising PEG groups can have a linear or branched structure.

The PEG group represented by $M^1$ or $M^2$ is typically a group represented by formula (III):

(III)

In the formula (III), ** is a binding position to $L^1$, and # is a binding position to O or $L^{2'}$. The weight-average molecular weight of the PEG group represented by formula (III) is typically 1 kDa or larger, preferably 5 kDa or larger, more preferably 10 kDa or larger, and further preferably 20 kDa or larger, and is typically 2000 kDa or smaller, preferably 1000 kDa or smaller, more preferably 100 kDa or smaller, further preferably 80 kDa or smaller, and especially preferably 60 kDa or smaller, in total in the modifying group A. The PEG group represented by formula (III) typically has a weight-average molecular weight ranging from 1 to 2000 kDa, for example, from 1 to 1000 kDa, and preferably has a weight-average molecular weight ranging from 1 to 100 kDa, more preferably from 5 to 80 kDa, further preferably from 10 to 60 kDa, and especially from 20 to 60 kDa, in total in the modifying group A. When the total weight-average molecular weight of the PEG group represented by formula (III) in the modifying group A falls within the ranges described above, a compound represented by formula (I) can have adrenomedullin activity substantially approximately equivalent to that of natural adrenomedullin. Furthermore, the compound represented by formula (I) can sustainably exert adrenomedullin activity in a living body while substantially suppressing unwanted side effects.

In the formula (III), n is the number of repeats of an ethylene oxide unit defined on the basis of the weight-average molecular weight. n defined on the basis of the preferred ranges of the weight-average molecular weight is typically an integer of approximately 20 or larger, preferably approximately 110 or larger, more preferably approximately 230 or larger, and further preferably approximately 460 or larger, and is typically an integer of approximately 45000 or smaller, preferably approximately 22000 or smaller, more preferably approximately 2200 or smaller, further preferably approximately 1820 or smaller, and especially preferably approximately 1360 or smaller. n defined on the basis of the preferred ranges of the weight-average molecular weight typically ranges from approximately 20 to 45000, for example, from approximately 20 to 22000, and preferably ranges from approximately 1 to 2200, more preferably from approximately 110 to 1820, further preferably from approximately 230 to 1360, and especially from approximately 460 to 1360. When the number n of repeats falls within the ranges described above, the total weight-average molecular weight of PEG groups contained in the modifying group represented by formula (II) falls within the ranges described above. Therefore, when the number n of repeats falls within the ranges described above, a compound represented by formula (I) can have adrenomedullin activity substantially approximately equivalent to that of natural adrenomedullin. Furthermore, the compound represented by formula (I) can sustainably exert adrenomedullin activity in a living body while substantially suppressing unwanted side effects.

$R^1$ is preferably hydrogen, substituted or unsubstituted $C_1$-$C_{20}$ alkyl, substituted or unsubstituted $C_2$-$C_{20}$ alkenyl, substituted or unsubstituted $C_2$-$C_{20}$ alkynyl, substituted or unsubstituted $C_3$-$C_{20}$ cycloalkyl, substituted or unsubstituted $C_4$-$C_{20}$ cycloalkenyl, substituted or unsubstituted $C_4$-$C_{20}$ cycloalkynyl, substituted or unsubstituted 3- to 6-membered heterocycloalkyl, substituted or unsubstituted $C_7$-$C_{20}$ cycloalkylalkyl, substituted or unsubstituted 3- to 6-membered heterocycloalkyl-$C_1$-$C_{20}$ alkyl, substituted or unsubstituted $C_4$-$C_{20}$ aryl, substituted or unsubstituted $C_5$-$C_{20}$ arylalkyl, substituted or unsubstituted 5- to 15-membered heteroaryl, substituted or unsubstituted 5- to 15-membered heteroaryl-$C_1$-$C_{20}$ alkyl, or substituted or unsubstituted acyl, more preferably hydrogen, substituted or unsubstituted $C_1$-$C_{20}$ alkyl, substituted or unsubstituted $C_2$-$C_{20}$ alkenyl, or substituted or unsubstituted $C_2$-$C_{20}$ alkynyl, further preferably hydrogen, methyl, ethyl, propyl, butyl, pentyl or hexyl, and especially preferably methyl. The substituents for the substituted groups are each independently preferably a monovalent group selected from the group consisting of halogen (fluorine, chlorine, bromine or iodine), cyano, nitro, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted amino, and substituted or unsubstituted $C_1$-$C_5$ alkoxy, and more preferably a monovalent group selected from the group consisting of halogen (fluorine, chlorine, bromine or iodine), cyano, nitro, unsubstituted $C_1$-$C_5$ alkyl, unsubstituted $C_2$-$C_5$ alkenyl, unsubstituted $C_2$-$C_5$ alkynyl, unsubstituted $C_3$-$C_6$ cycloalkyl, unsubstituted $C_3$-$C_6$ cycloalkenyl, unsubstituted $C_3$-$C_6$ cycloalkynyl, unsubstituted amino, and unsubstituted $C_1$-$C_5$ alkoxy. When $R^1$ is the groups, a compound represented by formula (I) can have adrenomedullin activity substantially approximately equivalent to that of natural adrenomedullin. Furthermore, the compound represented by formula (I) can sustainably exert adrenomedullin activity in a living body while substantially suppressing unwanted side effects.

$L^1$ is a m+1-valent linear or branched linking group. $L^1$ is preferably a substituted or unsubstituted m+1-valent linear or branched hydrocarbon group. The group optionally comprises one or more heteroatoms, an alicyclic group, an aromatic group, an amide group (—CO—NH—), an ester group (—CO—O—), or a urethane group (—O—CO—NH—). The substituents for the substituted groups are each independently preferably a monovalent group selected from the group consisting of halogen (fluorine, chlorine, bromine or iodine), cyano, nitro, and a substituted or unsubstituted linear or branched hydrocarbon group.

$L^2$ and $L^{2'}$ are each independently a bond or a divalent linking group. When each of $L^2$ and $L^{2'}$ is a divalent linking group, $L^2$ and $L^{2'}$ are each independently preferably a substituted or unsubstituted divalent hydrocarbon group, an amide group (—CO—NH—), an ester group (—CO—O—), or a urethane group (—O—CO—NH—), and more preferably substituted or unsubstituted $C_1$-$C_{20}$ alkylene, substituted or unsubstituted $C_2$-$C_{20}$ alkenylene, substituted or unsubstituted $C_2$-$C_{20}$ alkynylene, substituted or unsubstituted $C_3$-$C_{20}$ cycloalkylene, substituted or unsubstituted $C_4$-$C_{20}$ cycloalkenylene, substituted or unsubstituted $C_4$-$C_{20}$ cycloalkynylene, substituted or unsubstituted 3- to 6-membered heterocycloalkylene, substituted or unsubstituted $C_7$-$C_{20}$ cycloalkylalkylene, substituted or unsubstituted 3- to 6-membered heterocycloalkyl-$C_1$-$C_{20}$ alkylene, substituted or unsubstituted $C_4$-$C_{20}$ arylene, substituted or unsubstituted $C_5$-$C_{20}$ arylalkylene, substituted or unsubstituted 5- to 15-membered heteroarylene, substituted or unsubstituted 5- to 15-membered heteroaryl-$C_1$-$C_{20}$ alkylene, an amide group (—CO—NH—), an ester group (—CO—O—), or a urethane group (—O—CO—NH—). The groups optionally comprise one or more heteroatoms, an amide group (—CO—NH—), an ester group (—CO—O—), or a urethane group (—O—CO—NH—). The substituents for the substituted groups are each independently preferably a monovalent group selected from the group consisting of halogen (fluorine, chlorine, bromine or iodine), cyano, nitro, and a substituted or unsubstituted linear or branched hydrocarbon group, and more preferably a monovalent group selected from the group consisting of halogen (fluorine, chlorine, bromine or iodine), cyano, nitro, unsubstituted $C_1$-$C_5$ alkyl, unsubstituted $C_2$-$C_5$ alkenyl, unsubstituted $C_2$-$C_5$ alkynyl, unsubstituted $C_3$-$C_6$ cycloalkyl, unsubstituted $C_3$-$C_6$ cycloalkenyl, unsubstituted $C_3$-$C_6$ cycloalkynyl, unsubstituted amino, and unsubstituted $C_1$-$C_5$ alkoxy.

When $L^1$, $L^2$ and $L^{2'}$ are the groups, a compound represented by formula (I) can have adrenomedullin activity substantially approximately equivalent to that of natural adrenomedullin. Furthermore, the compound represented by formula (I) can sustainably exert adrenomedullin activity in a living body while substantially suppressing unwanted side effects.

Suitable modifying group A is a modifying group represented by the following formula (V), (VI), (VII) or (VIII):

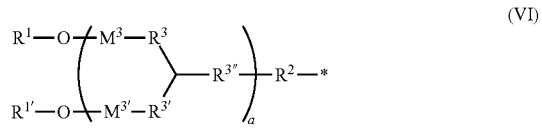

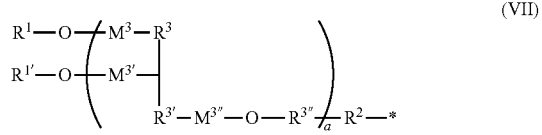

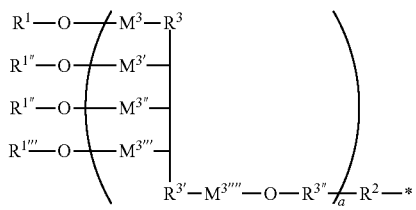

(VIII)

In the formulas (V), (VI), (VII) and (VIII), a is an integer of 1 or larger, $M^3$, $M^{3'}$, $M^{3''}$, $M^{3'''}$ and $M^{3''''}$ are each independently a bond or a PEG group, wherein when a plurality of $M^3$, $M^{3'}$, $M^{3''}$, $M^{3'''}$ or $M^{3''''}$ are present, the plurality of $M^3$, $M^{3'}$, $M^{3''}$, $M^{3'''}$ or $M^{3''''}$ are the same as or different from each other, and at least one of $M^3$, $M^{3'}$, $M^{3''}$, $M^{3'''}$ and $M^{3''''}$ is a PEG group, $R^1$, $R^{1'}$, $R^{1''}$ and $R^{1'''}$ are each independently hydrogen or a monovalent group, $R^2$ is a bond or a divalent group, $R^3$, $R^{3'}$ and $R^{3''}$ are each independently a bond or divalent group, wherein when a plurality of $R^3$, $R^{3'}$ or $R^{3''}$ are present, the plurality of $R^3$, $R^{3'}$ or $R^{3''}$ are the same as or different from each other, and

* is a binding position to the other moieties.

a is the number of repeats of a unit containing the PEG groups $M^3$, $M^{3'}$, $M^{3''}$, $M^{3'''}$ and $M^{3''''}$. For example, when a is 1, the unit has no repeat structure. When a in the formula (V) is 2 or larger, the unit has a linear repeat structure. When a in the formulas (VI), (VII) and (VIII) is 2 or larger, the unit has a dendritically branched repeat structure. a is typically an integer of 1 or larger and 5 or smaller and preferably ranges from an integer from 1 to 5 and more preferably from 1 to 2. When the number a of repeats of the unit containing the PEG groups $M^3$, $M^{3'}$, $M^{3''}$, $M^{3'''}$ and $M^{3''''}$ falls within the ranges described above, the modifying group A comprising PEG groups can have a linear or branched structure.

When each of $M^3$, $M^{3'}$, $M^{3''}$, $M^{3'''}$ and $M^{3''''}$ is a PEG group, the PEG group is typically a group represented by formula (III). The PEG group represented by formula (III) is as defined above. In this case, a compound represented by formula (I) can have adrenomedullin activity substantially approximately equivalent to that of natural adrenomedullin. Furthermore, the compound represented by formula (I) can sustainably exert adrenomedullin activity in a living body while substantially suppressing unwanted side effects.

$R^1$ is as defined above. $R^{1'}$, $R^{1''}$ and $R^{1'''}$ are as defined in the $R^1$. In this case, a compound represented by formula (I) can have adrenomedullin activity substantially approximately equivalent to that of natural adrenomedullin. Furthermore, the compound represented by formula (I) can sustainably exert adrenomedullin activity in a living body while substantially suppressing unwanted side effects.

$R^2$ is preferably a bond, a substituted or unsubstituted divalent hydrocarbon group, an amide group (—CO—NH—), an ester group (—CO—O—), or a urethane group (—O—CO—NH—), and more preferably a bond, substituted or unsubstituted $C_1$-$C_{20}$ alkylene, substituted or unsubstituted $C_2$-$C_{20}$ alkenylene, substituted or unsubstituted $C_2$-$C_{20}$ alkynylene, substituted or unsubstituted $C_3$-$C_{20}$ cycloalkylene, substituted or unsubstituted $C_4$-$C_{20}$ cycloalkenylene, substituted or unsubstituted $C_4$-$C_{20}$ cycloalkynylene, substituted or unsubstituted 3- to 6-membered heterocycloalkylene, substituted or unsubstituted $C_7$-$C_{20}$ cycloalkylalkylene, substituted or unsubstituted 3- to 6-membered heterocycloalkyl-$C_1$-$C_{20}$ alkylene, substituted or unsubstituted $C_4$-$C_{20}$ arylene, substituted or unsubstituted $C_5$-$C_{20}$ arylalkylene, substituted or unsubstituted 5- to 15-membered heteroarylene, substituted or unsubstituted 5- to 15-membered heteroaryl-$C_1$-$C_{20}$ alkylene, an amide group (—CO—NH—), an ester group (—CO—O—), or a urethane group (—O—CO—NH—). The divalent hydrocarbon group optionally comprises one or more heteroatoms, an amide group (—CO—NH—), an ester group (—CO—O—), or a urethane group (—O—CO—NH—). The substituents for the substituted groups are each independently preferably a monovalent group selected from the group consisting of halogen (fluorine, chlorine, bromine or iodine), cyano, nitro, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted amino, and substituted or unsubstituted $C_1$-$C_5$ alkoxy, and more preferably a monovalent group selected from the group consisting of halogen (fluorine, chlorine, bromine or iodine), cyano, nitro, unsubstituted $C_1$-$C_5$ alkyl, unsubstituted $C_2$-$C_5$ alkenyl, unsubstituted $C_2$-$C_5$ alkynyl, unsubstituted $C_3$-$C_6$ cycloalkyl, unsubstituted $C_3$-$C_6$ cycloalkenyl, unsubstituted $C_3$-$C_6$ cycloalkynyl, unsubstituted amino, and unsubstituted $C_1$-$C_5$ alkoxy. $R^2$ is preferably a bond or a substituted or unsubstituted $C_1$-$C_{10}$ alkylene group, more preferably a bond, methylene, ethylene, propylene or butylene, and further preferably a bond or ethylene.

$R^3$, $R^{3'}$ and $R^{3''}$ are each independently preferably a bond, a substituted or unsubstituted divalent hydrocarbon group, an amide group (—CO—NH—), an ester group (—CO—O—), or a urethane group (—O—CO—NH—), and more preferably a bond, substituted or unsubstituted $C_1$-$C_{20}$ alkylene, substituted or unsubstituted $C_2$-$C_{20}$ alkenylene, substituted or unsubstituted $C_2$-$C_{20}$ alkynylene, substituted or unsubstituted $C_3$-$C_{20}$ cycloalkylene, substituted or unsubstituted $C_4$-$C_{20}$ cycloalkenylene, substituted or unsubstituted $C_4$-$C_{20}$ cycloalkynylene, substituted or unsubstituted 3- to 6-membered heterocycloalkylene, substituted or unsubstituted $C_7$-$C_{20}$ cycloalkylalkylene, substituted or unsubstituted 3- to 6-membered heterocycloalkyl-$C_1$-$C_{20}$ alkylene, substituted or unsubstituted $C_4$-$C_{20}$ arylene, substituted or unsubstituted $C_5$-$C_{20}$ arylalkylene, substituted or unsubstituted 5- to 15-membered heteroarylene, substituted or unsubstituted 5- to 15-membered heteroaryl-$C_1$-$C_{20}$ alkylene, an amide group (—CO—NH—), an ester group (—CO—O—), or a urethane group (—O—CO—NH—). The divalent hydrocarbon group optionally comprises one or more heteroatoms, an amide group (—CO—NH—), an ester group (—CO—O—), or a urethane group (—O—CO—NH—). The substituents for the substituted groups are each independently preferably a monovalent group selected from the group consisting of halogen (fluorine, chlorine, bromine or iodine), cyano, nitro, substituted or unsubstituted $C_1$-$C_5$ alkyl, substituted or unsubstituted $C_2$-$C_5$ alkenyl, substituted or unsubstituted $C_2$-$C_5$ alkynyl, substituted or unsubstituted $C_3$-$C_6$ cycloalkyl, substituted or unsubstituted $C_3$-$C_6$ cycloalkenyl, substituted or unsubstituted $C_3$-$C_6$ cycloalkynyl, substituted or unsubstituted amino, and substituted or unsubstituted $C_1$-$C_5$ alkoxy, and more preferably a monovalent group selected from the group consisting of halogen (fluorine, chlorine, bromine or iodine), cyano, nitro, unsubstituted $C_1$-$C_5$ alkyl, unsubstituted $C_2$-$C_5$ alkenyl, unsubstituted $C_2$-$C_5$ alkynyl, unsubstituted $C_3$-$C_6$ cycloalkyl, unsubstituted $C_3$-$C_6$ cycloalkenyl, unsubstituted $C_3$-$C_6$ cycloalkynyl, unsubstituted amino, and unsubstituted $C_1$-$C_5$ alkoxy. $R^3$, $R^{3'}$ and $R^{3''}$ are each independently preferably a bond, substituted or unsubstituted $C_1$-$C_{10}$ alkylene group, a substituted or unsubstituted $C_1$-$C_{10}$ alkylene group containing an amide group, or an amide group (—CO—NH—), more preferably a bond, methylene, ethylene, —CO—NH—$(CH_2)_4$—, —$CH_2$—O—CO—NH—$(CH_2)_3$— or —CO—NH—.

When each of $R^2$, $R^3$, $R^{3'}$ and $R^{3''}$ is the groups, a compound represented by formula (I) can have adrenomedullin activity substantially approximately equivalent to that of natural adrenomedullin. Furthermore, the compound represented by formula (I) can sustainably exert adrenomedullin activity in a living body while substantially suppressing unwanted side effects.

Especially suitable modifying group A is a modifying group represented by the following formula (V-1-1), (VI-1-1), (VII-1-1), (VII-1-2), (VII-2-1), or (VIII-1-1):

In the formula (VII-1-1), the PEG groups preferably have a weight-average molecular weight of 5 kDa, 10 kDa, 20 kDa, 30 kDa, 40 kDa, 60 kDa or 80 kDa in total.

In the formula (VII-1-2), the PEG groups preferably have a weight-average molecular weight of 50 kDa in total. In this case, typically, the ethylene oxide unit of $(CH_2CH_2O)_n$ has a weight-average molecular weight of 40 kDa in total, and the ethylene oxide unit of $(CH_2CH_2O)_{n'}$ has a weight-average molecular weight of 10 kDa in total.

In the formula (VII-2-1), the PEG groups preferably have a weight-average molecular weight of 40 kDa in total. In this case, typically, the ethylene oxide unit of $(CH_2CH_2O)_n$ has a weight-average molecular weight of 30 kDa in total, and the ethylene oxide unit of $(CH_2CH_2O)_{n'}$ has a weight-average molecular weight of 10 kDa in total. Alternatively, the PEG groups preferably have a weight-average molecular weight of 60 kDa in total. In this case, typically, the ethylene

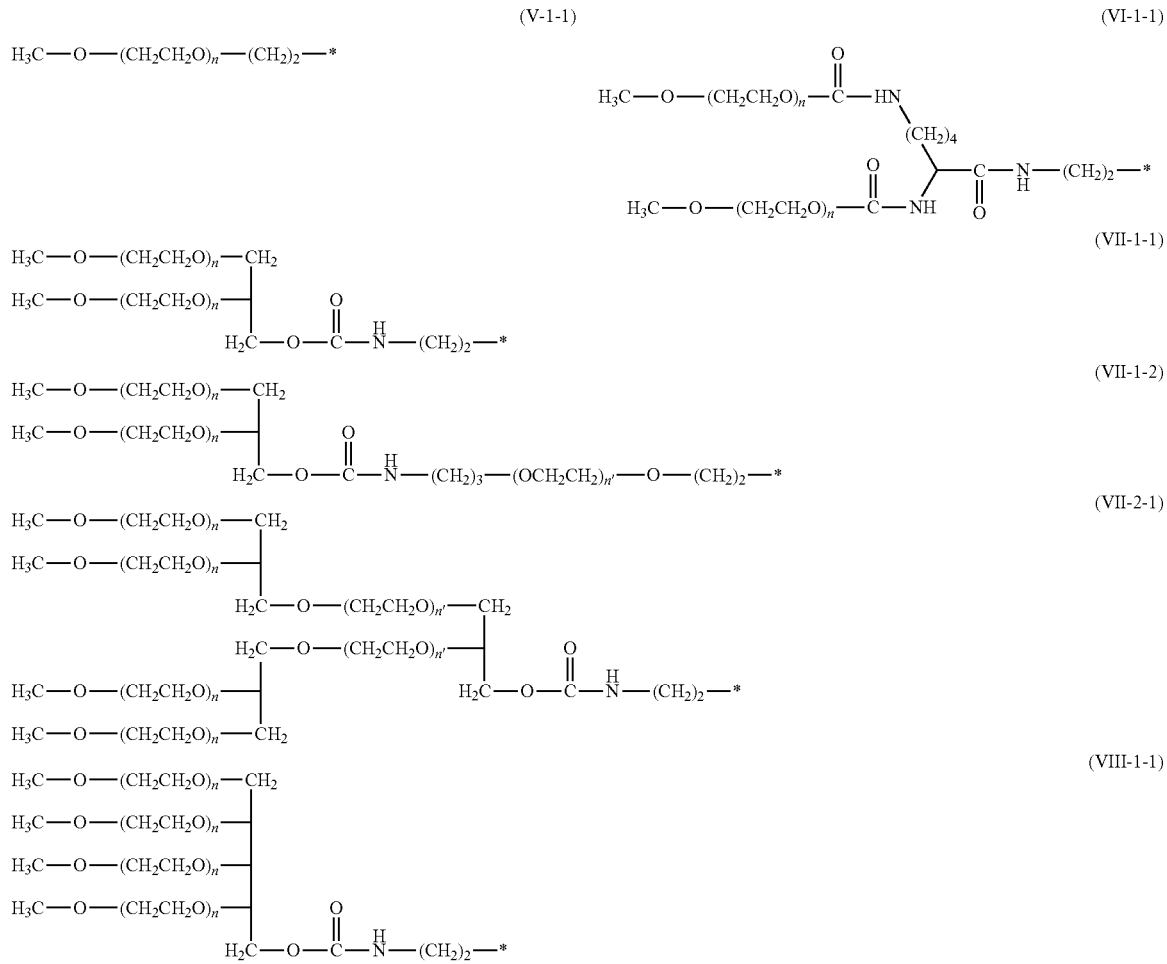

wherein
n is as defined above,
n' is as defined above about n, and
* is a binding position to the other moieties.

In the formula (V-1-1), the PEG group preferably has a weight-average molecular weight of 5 kDa, 10 kDa, 20 kDa, 30 kDa, 40 kDa, 60 kDa or 80 kDa in total.

In the formula (VI-1-1), the PEG groups preferably have a weight-average molecular weight of 40 kDa in total.

oxide unit of $(CH_2CH_2O)_n$ has a weight-average molecular weight of 50 kDa in total, and the ethylene oxide unit of $(CH_2CH_2O)_{n'}$ has a weight-average molecular weight of 10 kDa in total. Alternatively, the PEG groups preferably have a weight-average molecular weight of 80 kDa in total. In this case, typically, the ethylene oxide unit of $(CH_2CH_2O)_n$ has a weight-average molecular weight of 70 kDa in total, and the ethylene oxide unit of $(CH_2CH_2O)_{n'}$ has a weight-average molecular weight of 10 kDa in total.

In the formula (VIII-1-1), the PEG groups preferably have a weight-average molecular weight of 40 kDa in total.

By use of the groups as the modifying group A, a compound represented by formula (I) can substantially suppress unwanted side effects and sustainably exert adrenomedullin activity in a living body, while maintaining pharmacological effects of natural adrenomedullin.

In the formula (I), the peptide moiety B is required to be linked to the other moieties through a covalent bond of the nitrogen atom of the N-terminal α-amino group of the peptide moiety B to the carbon atom of the methylene group. In the invention, a compound in which the modifying group A comprising one or more PEG groups and the peptide moiety B are linked in the manner of linking described above may be described as "alkylamine linkage-type adrenomedullin derivative". The alkylamine linkage-type adrenomedullin derivative has higher adrenomedullin activity as compared to an adrenomedullin derivative in which adrenomedullin is linked to the other moieties through an amide bond of the nitrogen atom of the N-terminal α-amino group of the adrenomedullin (hereinafter, also described as "amide linkage-type adrenomedullin derivative"), as with the adrenomedullin derivative described in Non Patent Literature 10. Furthermore, the alkylamine linkage-type adrenomedullin derivative of the invention represented by the formula (I) further suppresses unwanted side effects (such as excessive decreased blood pressure, tachycardia associated with increased reflex sympathetic nerve activity, and/or increased activity of renin) as compared to the amide linkage-type adrenomedullin derivative. Therefore, the compound of the invention represented by formula (I) can sustainably exert adrenomedullin activity in a living body while further suppressing unwanted side effects, as compared to known adrenomedullin derivatives.

In an especially suitable compound represented by formula (I),

A is a modifying group comprising PEG groups, represented by formula (V-1-1), (VI-1-1), (VII-1-1), (VII-1-2), (VII-2-1), or (VIII-1-1), and B is a peptide moiety derived from adrenomedullin or a modified form thereof with adrenomedullin activity, the adrenomedullin or the modified form being a peptide selected from the group consisting of:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of SEQ ID NO: 3, or a peptide consisting of the amino acid sequence of SEQ ID NO: 3 and having a disulfide bond formed by the cysteine residues at positions 16 and 21;
(c) a peptide consisting of the amino acid sequence of SEQ ID NO: 5, or a peptide consisting of the amino acid sequence of SEQ ID NO: 5 and having a disulfide bond formed by the cysteine residues at positions 16 and 21;
(d) a peptide consisting of the amino acid sequence of SEQ ID NO: 7, or a peptide consisting of the amino acid sequence of SEQ ID NO: 7 and having a disulfide bond formed by the cysteine residues at positions 16 and 21;
(e) a peptide consisting of the amino acid sequence of SEQ ID NO: 9, or a peptide consisting of the amino acid sequence of SEQ ID NO: 9 and having a disulfide bond formed by the cysteine residues at positions 14 and 19;
(f) a peptide consisting of the amino acid sequence of SEQ ID NO: 11, or a peptide consisting of the amino acid sequence of SEQ ID NO: 11 and having a disulfide bond formed by the cysteine residues at positions 14 and 19;
(i) any peptide of (a) to (f) wherein the peptide is amidated at the C-terminus thereof; and
(j) any peptide of (a) to (f) wherein the peptide has a glycine residue added to the C-terminus thereof, or a peptide selected from the group consisting of:
(h') any peptide of (a) to (d) wherein the peptide has deletion of amino acid residues at positions 1 to 15, positions 1 to 10, or positions 1 to 5 from the N-terminus thereof and has adrenomedullin activity, or the peptide of (e) or (f) wherein the peptide has deletion of amino acid residues at positions 1 to 13, positions 1 to 8, or positions 1 to 5 from the N-terminus thereof and has adrenomedullin activity;
(i) the peptide of (h') wherein the peptide is amidated at the C-terminus thereof; and
(j) the peptide of (h') wherein the peptide has a glycine residue added to the C-terminus thereof.

A compound represented by formula (I) having the properties described above can substantially suppress unwanted side effects and sustainably exert adrenomedullin activity in a living body, while maintaining pharmacological effects of natural adrenomedullin.

Another aspect of the invention relates to a compound represented by formula (X):

$$A'\text{-CO}\text{—}B \quad (X)$$

or a salt thereof, or a hydrate thereof. In the present specification, the compound represented by formula (X) may be described as "urethane linkage-type adrenomedullin derivative".

In the formula (X), B is required to be a peptide moiety derived from adrenomedullin or a modified form thereof with adrenomedullin activity. The peptide moiety B is as defined above about the compound represented by formula (I).

A' is required to be a modifying group comprising one or more PEG groups. However, A' is required to be linked to the other moieties through a covalent bond of the oxygen atom of the modifying group comprising PEG groups to the carbon atom of the carbonyl group. The modifying group A' having such a structure allows a compound represented by formula (X) to have a structure having the modifying group A' and the peptide moiety B linked via a urethane bond.

A' is preferably a modifying group represented by the following formula (XI), (XI') or (XII):

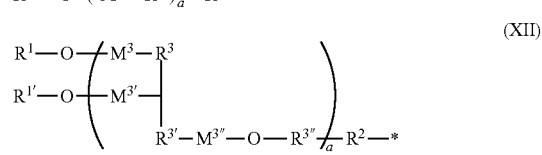

In the formulas (XI), (XI') and (XII), * is a binding position to the other moieties.

In the formulas (XI), (XI') and (XII), a, $R^1$, $R^{1'}$, $R^2$, $R^3$, $R^{3'}$, $R^{3''}$, $M^1$, $M^3$, $M^{3'}$ and $M^{3''}$ are as defined above about the compound represented by formula (I).

Especially suitable modifying group A' is a modifying group represented by the following formula (XI-1-1), (XII-1-1) or (XII-2-1):

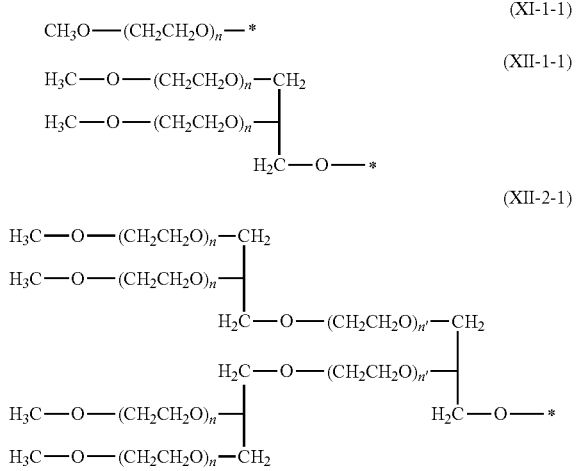

(XI-1-1)

(XII-1-1)

(XII-2-1)

wherein
n is as defined above,
n' is as defined above about n, and
* is a binding position to the other moieties.

In the formula (XI-1-1), the PEG group preferably has a weight-average molecular weight of 5 kDa, 10 kDa, 20 kDa, 30 kDa, 40 kDa, 60 kDa or 80 kDa in total.

In the formula (XII-1-1), the PEG groups preferably have a weight-average molecular weight of 5 kDa, 10 kDa, 20 kDa, 30 kDa, 40 kDa, 60 kDa or 80 kDa in total.

In the formula (XII-2-1), the PEG groups preferably have a weight-average molecular weight of 40 kDa in total. In this case, typically, the ethylene oxide unit of $(CH_2CH_2O)_n$ has a weight-average molecular weight of 30 kDa in total, and the ethylene oxide unit of $(CH_2CH_2O)_{n'}$ has a weight-average molecular weight of 10 kDa in total. Alternatively, the PEG groups preferably have a weight-average molecular weight of 60 kDa in total. In this case, typically, the ethylene oxide unit of $(CH_2CH_2O)_n$ has a weight-average molecular weight of 50 kDa in total, and the ethylene oxide unit of $(CH_2CH_2O)_{n'}$ has a weight-average molecular weight of 10 kDa in total. Alternatively, the PEG groups preferably have a weight-average molecular weight of 80 kDa in total. In this case, typically, the ethylene oxide unit of $(CH_2CH_2O)_n$ has a weight-average molecular weight of 70 kDa in total, and the ethylene oxide unit of $(CH_2CH_2O)_{n'}$ has a weight-average molecular weight of 10 kDa in total.

By use of the groups as the modifying group A', a compound represented by formula (X) can sustainably exert adrenomedullin activity in a living body while maintaining pharmacological effects of natural adrenomedullin.

In formula (X), the peptide moiety B is required to be linked to the other moieties through a covalent bond of the nitrogen atom of the N-terminal α-amino group of the peptide moiety B to the carbon atom of the carbonyl group. The urethane linkage-type adrenomedullin derivative has higher adrenomedullin activity as compared to the amide linkage-type adrenomedullin derivative described in Non Patent Literature 10. Therefore, the compound of the invention represented by formula (X) can sustainably exert higher adrenomedullin activity in a living body as compared to known adrenomedullin derivatives.

In an especially suitable compound represented by formula (X),

A' is a modifying group comprising PEG groups, represented by formula (XI-1-1), (XII-1-1) or (XII-2-1), and B is a peptide moiety derived from adrenomedullin or a modified form thereof with adrenomedullin activity, the adrenomedullin or the modified form being a peptide selected from the group consisting of:
(a) a peptide consisting of the amino acid sequence of SEQ ID NO: 1, or a peptide consisting of the amino acid sequence of SEQ ID NO: 1 and having a disulfide bond formed by the cysteine residues at positions 16 and 21;
(b) a peptide consisting of the amino acid sequence of SEQ ID NO: 3, or a peptide consisting of the amino acid sequence of SEQ ID NO: 3 and having a disulfide bond formed by the cysteine residues at positions 16 and 21;
(c) a peptide consisting of the amino acid sequence of SEQ ID NO: 5, or a peptide consisting of the amino acid sequence of SEQ ID NO: 5 and having a disulfide bond formed by the cysteine residues at positions 16 and 21;
(d) a peptide consisting of the amino acid sequence of SEQ ID NO: 7, or a peptide consisting of the amino acid sequence of SEQ ID NO: 7 and having a disulfide bond formed by the cysteine residues at positions 16 and 21;
(e) a peptide consisting of the amino acid sequence of SEQ ID NO: 9, or a peptide consisting of the amino acid sequence of SEQ ID NO: 9 and having a disulfide bond formed by the cysteine residues at positions 14 and 19;
(f) a peptide consisting of the amino acid sequence of SEQ ID NO: 11, or a peptide consisting of the amino acid sequence of SEQ ID NO: 11 and having a disulfide bond formed by the cysteine residues at positions 14 and 19;
(i) any peptide of (a) to (f) wherein the peptide is amidated at the C-terminus thereof; and
(j) any peptide of (a) to (f) wherein the peptide has a glycine residue added to the C-terminus thereof, or a peptide selected from the group consisting of:
(h') any peptide of (a) to (d) wherein the peptide has deletion of amino acid residues at positions 1 to 15, positions 1 to 10, or positions 1 to 5 from the N-terminus thereof and has adrenomedullin activity, or the peptide of (e) or (f) wherein the peptide has deletion of amino acid residues at positions 1 to 13, positions 1 to 8, or positions 1 to 5 from the N-terminus thereof and has adrenomedullin activity;
(i) the peptide of (h') wherein the peptide is amidated at the C-terminus thereof; and
(j) the peptide of (h') wherein the peptide has a glycine residue added to the C-terminus thereof.

A compound represented by formula (X) having the properties described above can sustainably exert higher adrenomedullin activity in a living body as compared to known adrenomedullin derivatives.

In the invention, compounds represented by formulas (I) and (X) include not only the compounds themselves but also salts thereof. When compounds represented by formulas (I) and (X) are in the form of salt, they are preferably pharmaceutically acceptable salts. Counterions in salts of the compounds of the invention preferably include, but are not limited to, for example, cations such as a sodium, potassium, calcium, magnesium, or substituted or unsubstituted ammonium ion, or anions such as a chloride, bromide, iodide, phosphate, nitrate, sulfate, carbonate, bicarbonate, perchlorate, formate, acetate, trifluoroacetate, propionate, lactate, maleate, hydroxymaleate, methylmaleate, fumarate, adipate, benzoate, 2-acetoxybenzoate, p-aminobenzoate, nicotinate, cinnamate, ascorbate, pamoate, succinate, salicylate, bismethylenesalicylate, oxalate, tartrate, malate, citrate, gluconate, aspartate, stearate, palmitate, itaconate, glycolate, glutamate, benzenesulfonate, cyclohexylsulfamate, methanesulfonate, ethanesulfonate, isethionate, benzenesulfonate, p-toluenesulfonate, or naphthalenesulfonate ion. When compounds represented by formulas (I) and (X) are in the form of salt with any of the counterions, adrenomedullin activity of the compounds can be substantially approximately equivalent to that of natural adrenomedullin.

Compounds represented by formulas (I) and (X) include not only the compounds themselves but also solvates of the compounds or salts thereof. When compounds represented by formulas (I) and (X) or salts thereof are in the form of solvate, they are preferably pharmaceutically acceptable solvates. Solvents that can form solvates with the compounds or salts thereof include, but are not limited to, for example, water or organic solvents such as methanol, ethanol, 2-propanol (isopropyl alcohol), dimethyl sulfoxide (DMSO), acetic acid, ethanolamine, acetonitrile, or ethyl acetate. When compounds represented by formulas (I) and (X) or salts thereof are in the form of solvate with any of the solvents described above, adrenomedullin activity of the compounds can be substantially approximately equivalent to that of natural adrenomedullin.

Compounds represented by formulas (I) and (X) include not only the compounds themselves described above or below but also protected forms thereof. In the present specification, a "protected form" means a form in which any suitable protecting group is introduced into one or more functional groups (such as a side-chain amino group of lysine residue) of the compound. In the present specification, a "protecting group" means a group that is introduced into a specific functional group to prevent any unwanted reaction from proceeding, will be removed quantitatively under a specific reaction condition, and is substantially stable, or inactive, under any reaction condition other than the specific reaction condition. Protecting groups that can form protected forms of the compounds include, but are not limited to, for example, t-butoxycarbonyl (Boc), 2-bromobenzyloxycarbonyl (BrZ), 9-fluorenylmethoxycarbonyl (Fmoc), p-toluenesulfonyl (Tos), benzyl (Bzl), 4-methylbenzyl (4-MeBzl), 2-chlorobenzyloxycarbonyl (ClZ), cyclohexyl (cHex), and phenacyl (Pac); other protecting groups of amino groups include benzyloxycarbonyl, p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenyl)isopropyloxycarbonyl, 2-(3,5-dimethoxyphenyl)isopropyloxycarbonyl, p-phenylazobenzyloxycarbonyl, triphenylphosphonoethyloxycarbonyl, 9-fluorenylmethyloxycarbonyl, t-amyloxyoxycarbonyl, diisopropylmethyloxycarbonyl, isopropyloxycarbonyl, ethyloxycarbonyl, allyloxycarbonyl, 2-methylsulfonylethyl oxycarbonyl, 2,2,2-trichloroethyloxycarbonyl, cyclopentyloxycarbonyl, cyclohexyloxycarbonyl, adamantyloxycarbonyl, isobornyloxycarbonyl, benzenesulfonyl, mesitylenesulfonyl, methoxytrimethylphenylsulfonyl, 2-nitrobenzensulfonyl, 2-nitrobenzenesulfenyl, 4-nitrobenzensulfonyl, and 4-nitrobenzene sulfenyl; other protecting groups of carboxyl groups include methyl esters, ethyl esters, t-butyl esters, p-methoxybenzyl esters, and p-nitrobenzyl esters; other side-chain protecting groups of Arg include 2,2,4,6,7-pentamethyl-2,3-dihydrobenzofuran-5-sulfonyl, 4-methoxy-2,3,6-trimethylbenzenesulphonyl, 2,2,5,7,8-pentamethylchroman-6-sulfonyl, and 2-methoxybenzenesulfonyl; other protecting groups of Tyr include 2,6-dichlorobenzyl, t-butyl, and cyclohexyl; other protecting groups of Cys include 4-methoxybenzyl, t-butyl, trityl, acetamidomethyl, and 3-nitro-2-pyridine sulfenyl; other protecting groups of His include benzyloxymethyl, p-methoxybenzyloxymethyl, t-butoxymethyl, trityl, and 2,4-dinitrophenyl; and other protecting groups of Ser and Thr include t-butyl. When a compound represented by formulas (I) and (X) is in a protected form with any of the protecting groups described above, adrenomedullin activity of the compound can be substantially approximately equivalent to that of natural adrenomedullin.

Compounds represented by formulas (I) and (X) include individual enantiomer and diastereomer of the compounds, and mixtures of stereoisomeric forms of the compounds such as racemates.

A compound represented by formula (I) and (X) having the properties described above can substantially suppress unwanted side effects and sustainably exert adrenomedullin activity in a living body, while maintaining pharmacological effects of natural adrenomedullin.

<2. Pharmaceutical Use of Adrenomedullin Derivatives>

A compound of the invention represented by formulas (I) and (X) can sustainably exert bioactivity substantially approximately equivalent to that of adrenomedullin, which is the parent molecule of the compound, (i.e., adrenomedullin activity) in a living body. Therefore, the invention relates to a medicament comprising a compound of the invention represented by formula (I) or (X) or a pharmaceutically acceptable salt thereof, or a pharmaceutically acceptable hydrate thereof as an active ingredient.

A compound of the invention represented by formulas (I) and (X) may be used alone or in combination with one or more pharmaceutically acceptable components when the compound is applied to pharmaceutical use. A medicament of the invention can be formulated into various dosage forms commonly used in the art depending on the desired mode of administration. Thus, the medicament of the invention can also be provided in the form of a pharmaceutical composition comprising a compound of the invention represented by formulas (I) and (X) and one or more pharmaceutically acceptable carriers. Pharmaceutical compositions of the invention may comprise, in addition to the components described above, one or more pharmaceutically acceptable carriers, excipients, binders, vehicles, dissolution aids, preservatives, stabilizers, bulking agents, lubricants, surfactants, oily liquids, buffering agents, soothing agents, antioxidants, sweetening agents, flavoring agents, and so forth.

Dosage forms of medicaments comprising a compound of the invention represented by formulas (I) and (X) as an active ingredient are not particularly limited and may be a formulation for parenteral or oral administration. Dosage forms of medicaments of the invention may also be a formulation in unit dosage form or in multiple dosage form. Formulations for use in parenteral administration include, for example, injections such as sterile solutions or suspensions in water or any other pharmaceutically acceptable liquid. Additive agents that can be admixed into the injections include, but are not limited to, for example, vehicles such as physiological saline and isotonic solutions comprising glucose or other pharmaceutic aids (such as D-sorbitol, D-mannitol, or sodium chloride); dissolution aids such as alcohols (such as ethanol or benzyl alcohol), esters (such as benzyl benzoate), and polyalcohols (such as propylene glycol or polyethylene glycol); nonionic surfactants such as polysorbate 80 or polyoxyethylene hydrogenated castor oil; oily liquids such as sesame oil or soybean oil; buffering agents such as phosphate buffer or sodium acetate buffer; soothing agents such as benzalkonium chloride or procaine hydrochloride; stabilizers such as human serum albumin or polyethylene glycol; preservatives; and antioxidants. The prepared injection will be generally filled in any suitable vial (such as an ampule) and preserved under an appropriate environment until use.

The formulations for use in oral administration include, for example, a tablet optionally coated with sugar coating or soluble film, a capsule, an elixir, a microcapsule, a tablet, a syrup, and a suspension. Additive agents that can be admixed into tablets or capsules and so forth include, but are not limited to, for example, binders such as gelatin, cornstarch, gum tragacanth, and gum arabic; excipients such as crystalline cellulose; bulking agents such as cornstarch, gelatin, and alginate; lubricants such as magnesium stearate; sweetening agents such as sucrose, lactose, or saccharin; and flavoring agents such as peppermint, *Gaultheria* adenothrix oil, or cherry. A formulation may further include liquid carriers such as oils/fats when the formulation is in the form of a capsule.

The compound of the invention represented by formulas (I) and (X) can sustainably exert adrenomedullin activity substantially approximately equivalent to that of adrenomedullin, which is the parent molecule of the compound, in a living body. Thus, a medicament comprising a compound of the invention represented by formulas (I) and (X) as an active ingredient can be formulated into a depot formulation. In this case, the medicament of the invention in the dosage form of depot formulation can, for example, be implanted subcutaneously or intramuscularly or administered by intramuscular injection. The depot formulation of the medicament of the invention allows the compound of the invention represented by formulas (I) and (X) to sustainably exert adrenomedullin activity for a long period of time.

The medicament comprising a compound of the invention represented by formulas (I) and (X) as an active ingredient can be combined with one or more other drugs useful as medicaments. In this case, the medicament of the invention may be provided in the form of a single medicament comprising the compound of the invention represented by formula (I) or (X) or a pharmaceutically acceptable salt thereof, or a pharmaceutically acceptable hydrate thereof and one or more other drugs, or may be provided in the form of a medicament combination or kit comprising a plurality of formulations into which the compound of the invention represented by formula (I) or (X) or a pharmaceutically acceptable salt thereof, or a pharmaceutically acceptable hydrate thereof and one or more other drugs are separately formulated. For the medicament combination or kit, each formulation can be administered simultaneously or separately (such as sequentially).

For applying compounds of the invention represented by formulas (I) and (X) to pharmaceutical use, the compounds represented by formulas (I) and (X) include not only the compounds themselves but also pharmaceutically acceptable salts thereof and pharmaceutically acceptable solvates thereof. The pharmaceutically acceptable salts of compounds of the invention represented by formulas (I) and (X) and pharmaceutically acceptable solvates thereof preferably include, but are not limited to, for example, salts or solvates exemplified above. When compounds represented by formulas (I) and (X) are in the form of any of the salts or solvates described above, the compounds can be applied to the desired pharmaceutical use.

A medicament comprising a compound of the invention represented by formulas (I) and (X) as an active ingredient can prevent or treat various conditions, diseases, and/or disorders that will be prevented or treated with adrenomedullin. The conditions, diseases, and/or disorders include, but are not limited to, for example, the following:

(1) Cardiovascular diseases: cardiac insufficiency, pulmonary hypertension, arteriosclerosis obliterans, Buerger's disease, myocardial infarction, lymphedema, Kawasaki's disease, myocarditis, high blood pressure, organ dysfunctions due to high blood pressure, and arteriosclerosis.

(2) Kidney and water and electrolyte system disorders: kidney failure and nephritis.

(3) Brain and nervous system diseases: cerebral infarction, dementia, and encephalitis.

(4) Urogenital diseases: erectile dysfunction (ED).

(5) Gastrointestinal diseases: inflammatory bowel disease, ulcerative disease, intestinal Behcet's disease, and hepatic failure.

(6) Orthopedic disease: arthritis.

(7) Endocrine metabolic disease: diabetes and organ dysfunctions due to diabetes, and primary aldosteronism.

(8) Others: septic shock, auto-immune disease, multiple organ failure, pressure sore, wound healing, and alopecia.

The cardiovascular disease is preferably any of myocardial infarction, pulmonary hypertension, and cardiac insufficiency. The gastrointestinal disease is preferably any of inflammatory diseases including a steroid-resistant or steroid-dependent inflammatory bowel disease (such as ulcerative colitis, Crohn's disease, or intestinal tract Behcet's disease).

A compound of the invention represented by formulas (I) and (X) has a structure in which adrenomedullin, which is a natural bioactive peptide, is linked to a modifying group. This structure allows the compound of the invention represented by formulas (I) and (X) to be safe and have low toxicity. Therefore, the medicament comprising the compound of the invention represented by formulas (I) and (X) as an active ingredient can be applied to various subjects in need of prevention or treatment of the condition, disease, and/or disorder. The subjects are preferably human or non-human mammalian (such as warm-blooded animal including pig, dog, cattle, rat, mouse, guinea pig, rabbit, chicken, sheep, cat, monkey, hamadryas baboon, or chimpanzee) subjects or patients. The medicament of the invention can be administered to the subjects to prevent or treat various conditions, diseases, and/or disorders that will be prevented or treated with adrenomedullin.

In the present specification, "prevention" means that onset (development or occurrence) of a condition, disease, and/or disorder will be substantially precluded. On the other hand, in the present specification, "treatment" means suppression (such as suppression of progression), remission, restoration, and/or cure of a condition, disease, and/or disorder that has appeared (developed or occurred).

The compound of the invention represented by formulas (I) and (X) can be used to prevent or treat the condition, disease, and/or disorder described above (such as a cardiovascular disease, peripheral vascular disease, or inflammatory disease) in subjects with the condition, disease, and/or disorder. Therefore, the medicament of the invention is preferably a medicament for use in the prevention or treatment of the condition, disease, and/or disorder described above and is more preferably a medicament for use in the prevention or treatment of a cardiovascular disease, an inflammatory disease, or a peripheral vascular disease. The invention also relates to an agent for preventing or treating a cardiovascular disease, an inflammatory disease, or a peripheral vascular disease comprising a compound of the invention represented by formula (I) or (X) or a pharmaceutically acceptable salt thereof, or a pharmaceutically acceptable hydrate thereof as an active ingredient. The compound of the invention represented by formulas (I) and (X) can be used to prevent or treat the condition, disease, and/or disorder described above to sustainably prevent or treat the condition, disease, and/or disorder.

Compounds of the invention represented by formulas (I) and (X) can be used to prevent or treat the condition, disease, and/or disorder described above (such as a cardiovascular disease, peripheral vascular disease, or inflammatory disease) in subjects with the condition, disease, and/or disorder. Therefore, one embodiment of the invention is a method for preventing or treating the disease or condition described above, comprising administering an effective amount of a compound of the invention represented by formulas (I) and (X) or a pharmaceutically acceptable salt thereof, or a pharmaceutically acceptable hydrate thereof to a subject in need of prevention or treatment of the condition, disease, and/or disorder described above. The condition, disease, and/or disorder is preferably any of cardiovascular diseases, peripheral vascular diseases, and inflammatory diseases. Compounds of the invention represented by formulas (I) and (X) can be administered to subjects in need of prevention or treatment of the condition, disease, and/or disorder to prevent or treat the condition, disease, and/or disorder.

Another embodiment of the invention is a compound of the invention represented by formula (I) or (X) or a pharmaceutically acceptable salt thereof, or a pharmaceutically acceptable hydrate thereof for use in the prevention or treatment of the condition, disease, and/or disorder described above. An alternative embodiment of the invention is use of a compound of the invention represented by formula (I) or (X) or a pharmaceutically acceptable salt thereof, or a pharmaceutically acceptable hydrate thereof for manufacturing a medicament for the prevention or treatment of the condition, disease, and/or disorder described above. The condition, disease, and/or disorder is preferably any of cardiovascular diseases, inflammatory diseases, and peripheral vascular diseases. The medicament of the invention can be used to prevent or treat the condition, disease, and/or disorder described above to sustainably prevent or treat the condition, disease, and/or disorder.

When a medicament comprising a compound of the invention represented by formulas (I) and (X) as an active ingredient is administered to a subject, particularly a human patient, the precise dose and number of doses will be determined considering many factors including age and sex of the subject, the precise condition (such as severity) of the condition, disease, and/or disorder to be prevented or treated, and the route of administration. The therapeutically effective dose and number of doses should be ultimately determined by the attending physician. Therefore, the compound represented by formulas (I) and (X), which is an active ingredient in the medicament of the invention, will be administered to the subject in the therapeutically effective dose and number of doses. For example, when the medicament of the invention is administered to a human patient, a dose of the compound represented by formulas (I) and (X), which is an active ingredient, will usually range from 0.01 to 100 mg per 60 kg of body weight per day and typically from 0.01 to 10 mg per 60 kg of body weight per day.

Route of administration and number of doses of a medicament comprising a compound of the invention represented by formulas (I) and (X) as an active ingredient are not particularly limited and the medicament may be administered orally or parenterally in a single dose or in multiple doses. The medicament of the invention is preferably administered parenterally such as intravenously, by intestinal infusion, subcutaneously, intramuscularly, or intraperitoneally, and more preferably intravenously or subcutaneously. The medicament of the invention is also preferably administered in a single dose. The medicament of the invention is particularly preferably used in intravenous or subcutaneous administration in a single dose. Adrenomedullin, which is the parent molecule of compounds of the invention represented by formulas (I) and (X), has a strong vasodilatory effect. This strong vasodilatory effect may cause unwanted side effects such as excessive decreased blood pressure, tachycardia associated with increased reflex sympathetic nerve activity, and/or increased activity of renin when a therapeutically effective amount of adrenomedullin is administered in a single dose. On the other hand, compounds of the invention represented by formulas (I) and (X) can significantly prolong blood half-life as compared to natural adrenomedullin while retaining adrenomedullin activity substantially approximately equivalent to that of natural adrenomedullin. Therefore, intravenous administration of the medicament comprising a compound of the invention represented by formulas (I) and (X) as an active ingredient to a subject in a single dose allows the medicament to sustainably prevent or treat a condition, disease, and/or disorder in the subject while suppressing unwanted side effects due to the vasodilation effect of adrenomedullin.

<3. Method for Producing Adrenomedullin Derivatives>

The invention also relates to a method for producing a compound of the invention represented by formulas (I) and (X).

[3-1. Step of Preparing Precursors]

The method of the invention may comprise preparing at least any of a precursor of peptide moiety B derived from adrenomedullin or a modified form thereof and a precursor of modifying group A or A' comprising one or more polyethylene glycol groups.

In the invention, "a precursor of peptide moiety B derived from adrenomedullin or a modified form thereof" means the adrenomedullin or the modified form thereof or means a derivative of the peptide moiety B that has been suitably modified or activated so that the peptide moiety B and the modifying group A or A' are linked together via condensation reactions in the linking step as described below. The precursor of peptide moiety B is preferably adrenomedullin or a modified form thereof itself, or a protected form thereof.

The precursor of modifying group A is typically a precursor aldehyde of modifying group A comprising one or more polyethylene glycol groups, the precursor aldehyde being represented by formula (I-1):

$$A\text{-CHO} \tag{I-1}$$

Preparation of precursors having properties described above in this step allows high-yield formation of a compound represented by formula (I) through reactions of linking each precursor in the linking step described below.

The precursor of modifying group A' is typically a precursor p-nitrophenyl carbonate ester of modifying group A' comprising one or more polyethylene glycol groups, the precursor p-nitrophenyl carbonate ester being represented by formula (X-1):

$$A'\text{-CO}\text{—O}\text{—}C_6H_4\text{-p-}NO_2 \tag{X-1}$$

Alternatively, the precursor of modifying group A' may be a precursor N-hydroxysuccinimidyl carbonate ester of modifying group A' comprising one or more polyethylene glycol groups, the precursor N-hydroxysuccinimidyl carbonate ester being represented by formula (X-2):

A'-CO—O—C$_4$H$_4$NO$_2$ (X-2)

Preparation of precursors having properties described above in this step allows high-yield formation of a compound represented by formula (X) through reactions of linking each precursor in the linking step described below.

In this step, the precursor of peptide moiety B derived from adrenomedullin or a modified form thereof can be prepared by any means commonly used in the art. The means may be, for example, a peptide synthesis method on solid phase system or in liquid phase system, or a method for purifying natural peptides from human or non-human mammalian tissues or cells that can produce adrenomedullin when the precursor of peptide moiety B is adrenomedullin or a modified form thereof itself. Alternatively, the means may be a method for overexpression of a recombinant protein using DNA encoding adrenomedullin in human or non-human mammal that can produce adrenomedullin (such as SEQ ID NO: 2, 4, 6, 8, 10, or 12) in a transformation system such as *Escherichia coli* or *Saccharomyces cerevisiae*. Alternatively, the already produced peptides may be also purchased. Any case will be included in the embodiment of this step.

A precursor that has a disulfide bond formed by two cysteine residues in the amino acid sequence in the precursor of peptide moiety B prepared by the means described above can be obtained by disulfide bond formation between thiol groups of two cysteine residues in the amino acid sequence. A precursor in which the disulfide bond formed between two cysteine residues in the amino acid sequence of the precursor of peptide moiety B prepared by the means described above has been substituted with an ethylene group can be obtained by substitution of the disulfide bond with an ethylene group. The formation reaction of a disulfide bond and the substitution reaction with an ethylene group can be performed based on any condition commonly used in the art. The formation reaction of a disulfide bond and the substitution reaction with an ethylene group may be performed in this step or in the linking step described below. Any case will be included in the embodiment of the step.

When at least any of the precursor of peptide moiety B, and the precursor of modifying group A or A' are in a protected form, the protection step in which one or more protecting groups are introduced into at least any of the precursor of peptide moiety B, and the precursor of modifying group A or A' and/or the deprotection step in which at least any of one or more protecting groups in protected forms of the precursor of peptide moiety B, and the precursor of modifying group A or A' are deprotected may be performed in this step as desired. The protection and deprotection steps can be performed with any protection and deprotection reaction commonly used in the art. The protection and deprotection steps may be performed in this step or in the linking step described below. Any case will be included in the embodiment of this step.

[3-2. Linking Step]

The method of the invention is required to comprise a linking step of linking the precursor of peptide moiety B derived from adrenomedullin or a modified form thereof, and the precursor of modifying group A or A' to give a compound represented by formula (I) or (X).

To form a compound represented by formula (I), this step is typically performed by reacting the precursor of peptide moiety B with the precursor aldehyde represented by formula (I-1) of modifying group A comprising one or more PEG groups in the presence of a reducing agent. Reducing agents that can be used in this step can include, but are not limited to, sodium cyanoborohydride (NaCNBH$_3$), sodium borohydride (NaBH$_4$), dimethylamine borate, trimethylamine borate, pyridine borate, pyridine borane, 2-picoline borane and 3-picoline borane. The reaction temperature in this step preferably ranges from −20 to 50° C. and more preferably from 0 to 15° C. The reaction time in this step preferably ranges from 5 minutes to 100 hours.

To form a compound represented by formula (X), this step is typically performed by reacting the precursor of peptide moiety B with the precursor p-nitrophenyl carbonate ester or N-hydroxysuccinimidyl carbonate ester represented by formula (X-1) or (X-2) of modifying group A' comprising one or more PEG groups in the presence of a base. Bases that can be used in this step can include, but are not limited to, triethylamine, pyridine and dimethylaminopyridine. The reaction temperature in this step preferably ranges from 0 to 50° C. The reaction time in this step preferably ranges from 5 minutes to 200 hours.

EXAMPLES

Hereinafter, the present invention will be described further specifically with reference to Examples. However, the technical scope of the present invention is not intended to be limited by these Examples.

Experiment I: Preparation of Full-Length Adrenomedullin Derivative

Experiment I-1: Synthesis of Full-Length Adrenomedullin Derivative

Experiment I-1-1: Synthesis of CH$_3$O-PEG (5k)-(CH$_2$)$_5$—CO—$^\alpha$NH-(h.AM (1-52)) (Compound (1))

In accordance with the method described in the known literature (Kubo, K et al., "Biological properties of adrenomedullin conjugated with polyethylene glycol.", Peptides, 2014, vol. 57, p. 118-21), a polyethylene glycol group with a weight-average molecular weight of 5 kDa (hereinafter, also described as "PEG (5k)") was linked via an amide bond to the N-terminal amino group of a Cys$^{16}$-Cys$^{21}$ disulfide bridge form of a peptide having the amino acid sequence of H-Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr- NH$_2$ (hereinafter, also described as "h.AM (1-52)"), which was a peptide corresponding to amino acid residues 1 to 52 of human adrenomedullin (SEQ ID NO: 1), using a N-hydroxysuccinimide active ester-type CH$_3$O-PEGylation reagent (PEG-1) (CH$_3$O—(CH$_2$CH$_2$O)$_n$—(CH$_2$)$_5$—CO—O—NHS) of 5 kDa to synthesize an amide linkage-type PEG (5k) adrenomedullin derivative (CH$_3$O-PEG (5k)-(CH$_2$)$_5$—CO—$^\alpha$NH-(h.AM (1-52))) (1).

Experiment I-1-2: Synthesis of CH$_3$O-PEG (20k)-(CH$_2$)$_5$—CO—$^\alpha$NH-(h.AM (1-52)) (Compound (2))

In the same way as in experiment I-1-1, a polyethylene glycol group with a weight-average molecular weight of 20 kDa (hereinafter, also described as "PEG (20k)") was linked via an amide bond to the N-terminal amino group of the h.AM (1-52) peptide using a N-hydroxysuccinimide active ester-type CH$_3$O-PEGylation reagent (PEG-1) (CH$_3$O—

($CH_2CH_2O)_n$—$(CH_2)_5$—CO—O—NHS) of 20 kDa to synthesize an amide linkage-type PEG (20k) adrenomedullin derivative ($CH_3O$-PEG (20k)-$(CH_2)_5$—CO—$^\alpha$NH-(h.AM (1-52))) (2).

Experiment I-1-3: Synthesis of $CH_3O$-PEG (10k)-$(CH_2)_2$—$CH_2$—$^\alpha$NH-(h.AM (1-52)) (Compound (3))

2 mg of the h.AM (1-52) peptide was dissolved in a 100 mM sodium acetate buffer (pH 5.5) to obtain 2 mL of a peptide solution. To this peptide solution, 16 mg of an aldehyde-type $CH_3$-PEGylation reagent (PEG-2) ($CH_3O$—($CH_2CH_2O)_n$—$(CH_2)_2$—CHO) with a weight-average molecular weight of 10 kDa was added under ice cooling. To this peptide solution, $NaCNBH_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (10k) adrenomedullin derivative ($CH_3O$-PEG (10k)-$(CH_2)_2$—$CH_2$—$^\alpha$NH-(h.AM (1-52))) (3) and unreacted h.AM (1-52) peptide were recovered in the eluted fraction. This eluted fraction was concentrated into 0.2 mL using an ultrafiltration membrane (Amicon Ultra 4, Merck Millipore). The obtained concentrate was purified and fractionated using a high-performance liquid chromatography (HPLC) system (L-2000; manufactured by Hitachi High-Tech Science Corp.) connected with Superdex 200 HR 10/30 (GE Healthcare Japan Corp.) column (eluent: 80 mM sodium acetate buffer, pH 6+20% $CH_3CN$ containing 80 mM $Na_2SO_4$, flow rate: 0.5 mL/min). The preparative HPLC yielded 1.0 mg (based on h.AM (1-52)) of the compound (3) of interest.

Experiment I-1-4: Synthesis of $CH_3O$-PEG (20k)-$(CH_2)_2$—$CH_2$—$^\alpha$NH-(h.AM (1-52)) (Compound (4))

1 mg of the h.AM (1-52) peptide was dissolved in a 100 mM sodium acetate buffer (pH 5.5) to obtain 1 mL of a peptide solution. To this peptide solution, 32 mg of an aldehyde-type $CH_3O$-PEGylation reagent (PEG-2) ($CH_3O$—($CH_2CH_2O)_n$—$(CH_2)_2$—CHO) with a weight-average molecular weight of 20 kDa was added under ice cooling. To this peptide solution, $NaCNBH_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (20k) adrenomedullin derivative ($CH_3O$-PEG (20k)-$(CH_2)_2$—$CH_2$—$^\alpha$NH-(h.AM (1-52))) (4) and unreacted h.AM (1-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Superdex 200 HR 10/30 (GE Healthcare Japan Corp.) column (eluent: 80 mM sodium acetate buffer, pH 6+20% $CH_3CN$ containing 80 mM $Na_2SO_4$, flow rate: 0.5 mL/min). The preparative HPLC yielded 0.3 mg (based on h.AM (1-52)) of the compound (4) of interest.

Experiment I-1-5: Synthesis of $CH_3O$-PEG (30k)-$(CH_2)_2$—$CH_2$—$^\alpha$NH-(h.AM (1-52)) (Compound (5))

2 mg of the h.AM (1-52) peptide was dissolved in a 100 mM sodium acetate buffer (pH 5.5) to obtain 2 mL of a peptide solution. To this peptide solution, 30 mg of an aldehyde-type $CH_3O$-PEGylation reagent (PEG-2) ($CH_3O$—($CH_2CH_2O)_n$—$(CH_2)_2$—CHO) with a weight-average molecular weight of 30 kDa was added under ice cooling. To this peptide solution, $NaCNBH_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (30k) adrenomedullin derivative ($CH_3O$-PEG (30k)-$(CH_2)_2$—$CH_2$—$^\alpha$NH-(h.AM (1-52))) (5) and unreacted h.AM (1-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Superdex 200 HR 10/30 (GE Healthcare Japan Corp.) column (eluent: 100 mM sodium acetate buffer, pH 6+200 mM $Na_2SO_4$, flow rate: 0.5 mL/min). The preparative HPLC yielded 0.8 mg (based on h.AM (1-52)) of the compound (5) of interest.

Experiment I-1-6: Synthesis of GL-2-Branched $CH_3O$-PEG (20k)-$CH_2$—$^\alpha$NH-(h.AM (1-52)) (Compound (6))

The same procedures as in experiment I-1-5 were carried out except that 45 mg of an aldehyde-type $CH_3O$-PEGylation reagent (PEG-3) with a weight-average molecular weight of 20 kDa represented by formula (VII-1-1'):

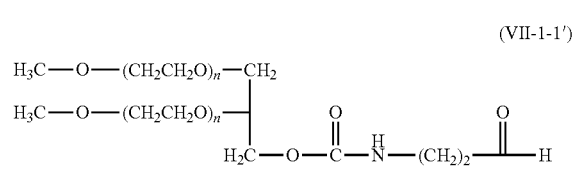

(VII-1-1')

was used instead of the $CH_3O$-PEGylation reagent (PEG-2), to obtain a glycerol skeleton-containing 2-branched alkylamine linkage-type PEG (20k) adrenomedullin derivative (GL-2-branched $CH_3O$-PEG (20k)-$CH_2$—$^\alpha$NH-(h.AM (1-52))) (6):

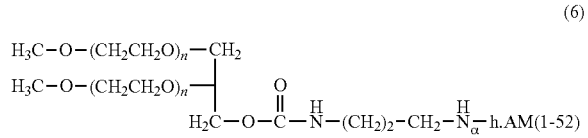
(6)

Preparative HPLC yielded 1.0 mg (based on h.AM (1-52)) of the compound (6) of interest.

Experiment I-1-7: Synthesis of GL-2-branched CH$_3$O-PEG (40k)-CH$_2$—$^\alpha$NH-(h.AM (1-52)) (Compound (7))

The same procedures as in experiment I-1-5 were carried out except that 80 mg of an aldehyde-type CH$_3$O-PEGylation reagent (PEG-3) with a weight-average molecular weight of 40 kDa represented by formula (VII-1-1'):

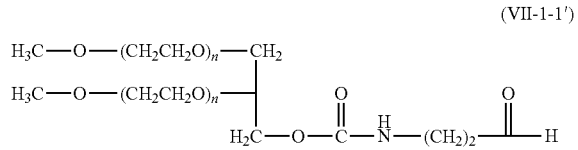
(VII-1-1')

was used instead of the CH$_3$O-PEGylation reagent (PEG-2), to obtain a glycerol skeleton-containing 2-branched alkylamine linkage-type PEG (40k) adrenomedullin derivative (GL-2-branched CH$_3$O-PEG (40k)-CH$_2$—$^\alpha$NH-(h.AM (1-52))) (7):

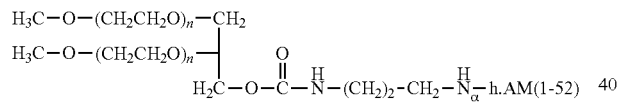
(7)

Preparative HPLC yielded 1.2 mg (based on h.AM (1-52)) of the compound (7) of interest.

Experiment I-1-8: Preparation of GL-2-branched CH$_3$O-PEG (60k)-CH$_2$—$^\alpha$NH-(h.AM (1-52)) (Compound (8))

The same procedures as in experiment I-1-4 were carried out except that 40 mg of an aldehyde-type CH$_3$O-PEGylation reagent (PEG-3) with a weight-average molecular weight of 60 kDa represented by formula (VII-1-1'):

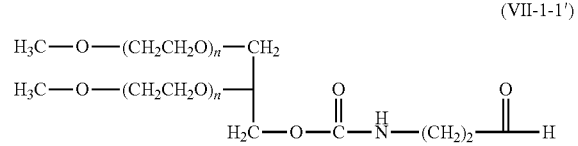
(VII-1-1')

was used instead of the CH$_3$O-PEGylation reagent (PEG-2), to obtain a glycerol skeleton-containing 2-branched alkylamine linkage-type PEG (60k) adrenomedullin derivative (GL-2-branched CH$_3$O-PEG (60k)-CH$_2$—$^\alpha$NH-(h.AM (1-52))) (8):

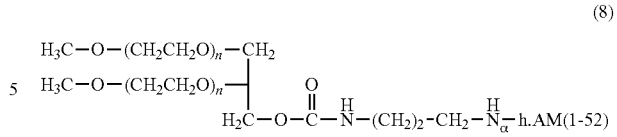
(8)

Preparative HPLC yielded 0.4 mg (based on h.AM (1-52)) of the compound (8) of interest.

Experiment I-1-9: Synthesis of GL-2-branched CH$_3$O-PEG (80k)-CH$_2$—$^\alpha$NH-(h.AM (1-52)) (Compound (9))

The same procedures as in experiment I-1-5 were carried out except that 121 mg of an aldehyde-type CH$_3$O-PEGylation reagent (PEG-3) with a weight-average molecular weight of 80 kDa represented by formula (VII-1-1'):

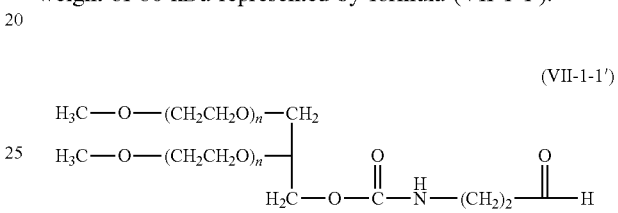
(VII-1-1')

was used instead of the CH$_3$O-PEGylation reagent (PEG-2), to obtain a glycerol skeleton-containing 2-branched alkylamine linkage-type PEG (80k) adrenomedullin derivative (GL-2-branched CH$_3$O-PEG (60k)-CH$_2$—$^\alpha$NH-(h.AM (1-52))) (9):

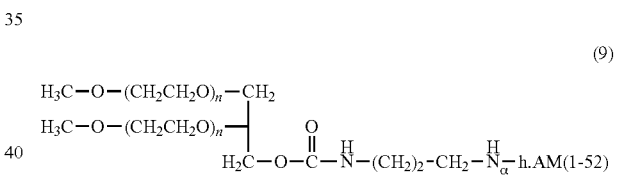
(9)

Preparative HPLC yielded 1.1 mg (based on h.AM (1-52)) of the compound (9) of interest.

Experiment I-1-10: Synthesis of Lys-2-branched CH$_3$O-PEG (40k)-CH$_2$—$^\alpha$NH-(h.AM (1-52)) (Compound (10))

The same procedures as in experiment I-1-4 were carried out except that 42.9 mg of an aldehyde-type CH$_3$O-PEGylation reagent (PEG-4) with a weight-average molecular weight of 40 kDa represented by formula (VI-1-1'):

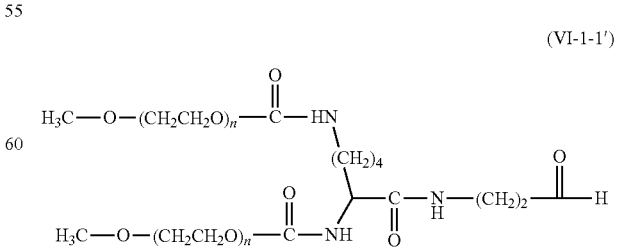
(VI-1-1')

was used instead of the CH$_3$O-PEGylation reagent (PEG-2), to obtain a lysine skeleton-containing 2-branched alkylamine linkage-type PEG (40k) adrenomedullin derivative (Lys-2-branched CH$_3$O-PEG (40k)-CH$_2$—$^\alpha$NH-(h.AM (1-52))) (10):

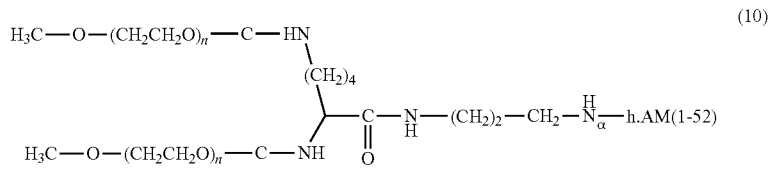

(10)

Preparative HPLC yielded 0.4 mg (based on h.AM (1-52)) of the compound (10) of interest.

Experiment I-1-11: Synthesis of GL-4-branched CH$_3$O-PEG (40k)-CH$_2$—$^\alpha$NH-(h.AM (1-52)) (Compound (11))

The same procedures as in experiment I-1-3 were carried out except that 93 mg of an aldehyde-type CH$_3$O-PEGylation reagent (PEG-5) with a weight-average molecular weight of 40 kDa represented by formula (VII-2-1'):

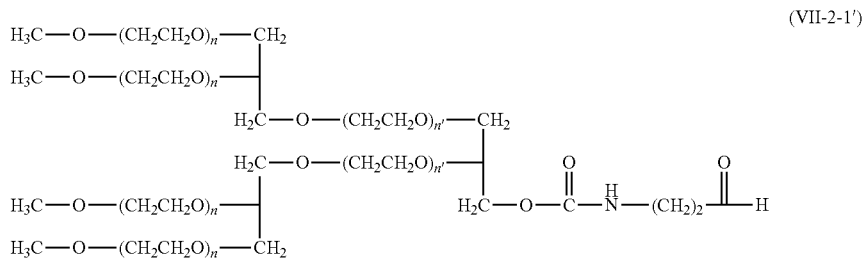

(VII-2-1')

was used instead of the CH$_3$O-PEGylation reagent (PEG-2), to obtain a glycerol skeleton-containing 4-branched alkylamine linkage-type PEG (40k) adrenomedullin derivative (GL-4-branched CH$_3$O-PEG (40k)-CH$_2$—$^\alpha$NH-(h.AM (1-52))) (11):

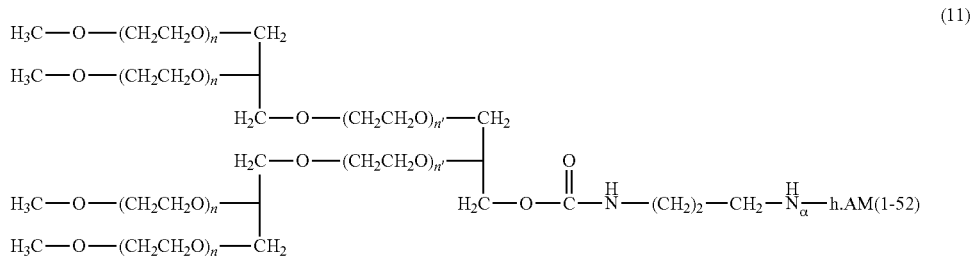

(11)

Preparative HPLC yielded 1.1 mg (based on h.AM (1-52)) of the compound (11) of interest.

Experiment I-1-12: Synthesis of Xyl-4-branched CH₃O-PEG (40k)-CH₂—ᵅNH-(h.AM (1-52)) (Compound (12))

The same procedures as in experiment I-1-3 were carried out except that 94 mg of an aldehyde-type CH₃O-PEGylation reagent (PEG-6) with a weight-average molecular weight of 40 kDa represented by formula (VIII-1-1'):

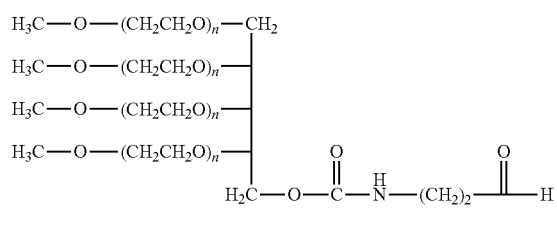

(VIII-1-1')

was used instead of the CH₃O-PEGylation reagent (PEG-2), to obtain a xylose skeleton-containing 4-branched alkylamine linkage-type PEG (40k) adrenomedullin derivative (Xyl-4-branched CH₃O-PEG (40k)-CH₂—ᵅNH-(h.AM (1-52))) (12):

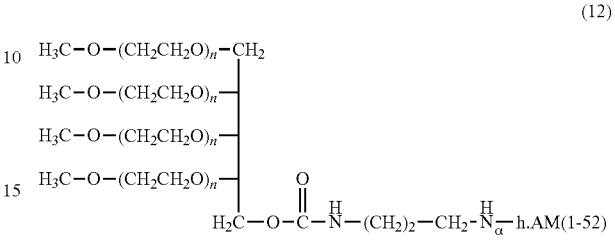

(12)

Preparative HPLC yielded 1.0 mg (based on h.AM (1-52)) of the compound (12) of interest.

Experiment I-1-13: Synthesis of GL-3-Branched CH₃O-PEG (50k)-CH₂—ᵅNH-(h.AM (1-52)) (Compound (13))

The same procedures as in experiment I-1-3 were carried out except that 94 mg of an aldehyde-type CH₃O-PEGylation reagent (PEG-7) with a weight-average molecular weight of 50 kDa represented by formula (VII-1-2'):

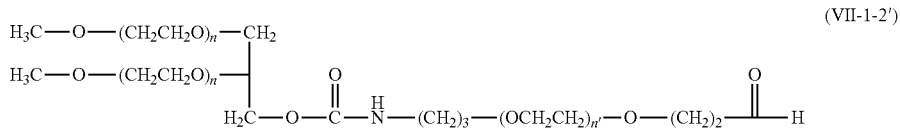

(VII-1-2')

was used instead of the CH₃O-PEGylation reagent (PEG-2), to obtain a glycerol skeleton-containing 3-branched alkylamine linkage-type PEG (50k) adrenomedullin derivative (GL-3-branched CH₃O-PEG (50k)-CH₂—ᵅNH-(h.AM (1-52))) (13):

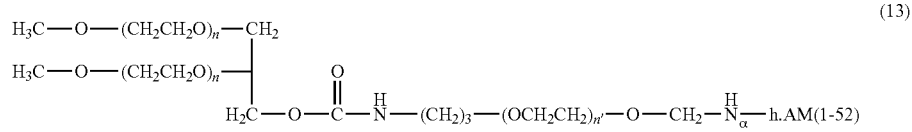

(13)

Preparative HPLC yielded 0.9 mg (based on h.AM (1-52)) of the compound (13) of interest.

Experiment I-1-14: Synthesis of CH₃O-PEG (20k)-CO—$^{\alpha}$NH-(h.AM (1-52)) (Compound (14))

A Cys$^{16}$-Cys$^{21}$ disulfide bridge form of a peptide having the amino-acid sequence of Fmoc-Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-NH₂ (hereinafter, also described as "Fmoc—$^{\alpha}$NH-(h.AM (1-52))") was synthesized on commission by the Fmoc peptide synthesis method. 18 mg of the Fmoc—$^{\alpha}$NH-(h.AM (1-52)) peptide was dissolved in 1.8 mL of dimethyl sulfoxide (DMSO). To this solution, 9 mg of t-butyl succinimidyl carbonate and 6 L of diisopropylethylamine were added. The reaction solution was stirred for 5 hours. To the obtained reaction solution, an aqueous acetic acid solution was added. Then, this solution was freeze-dried. The residue was dissolved in 2 mL of DMSO. To the obtained solution, 0.2 mL of diethylamine was added. The obtained solution was stirred for 70 minutes. The reaction solution was diluted by the addition of an aqueous acetic acid solution. The obtained solution was fractionated using reverse-phase HPLC to obtain a fraction containing the h.AM (1-52) peptide. This fraction was freeze-dried to obtain 10 mg of h.AM (1-52) peptide having 4 lysine residues protected with Boc groups as a white powder.

2 mg of the obtained peptide was dissolved in 2 mL of DMSO. To this peptide solution, 15 mg of a p-nitrophenyl ester-type CH₃O-PEGylation reagent (PEG-8) (CH₃O—(CH₂CH₂O)$_n$—CO—O—C₆H₄-p-NO₂) with a weight-average molecular weight of 20 kDa was added under ice cooling. To this peptide solution, 6.5 μL of a 0.1 M solution of triethylamine in DMSO was further added. The reaction solution was left for 1 hour under ice cooling. Then, the reaction solution was brought back to room temperature and left for 24 hours. The temperature of the reaction solution was further raised to 30° C., and the reaction was continued for 2 days. The reaction solution was freeze-dried. To the obtained residue, 1 mL of trifluoroacetic acid was added under ice cooling. The mixture was brought back to room temperature and left for 2 hours. Subsequently, the trifluoroacetic acid was distilled away under reduced pressure from the mixture using an evaporator. The obtained residue was dissolved by the addition of 4 mL of a 50 mM sodium acetate buffer (pH 4.0). This solution was applied at a flow rate of 1 mL/hr to SP-Sepharose HP (GE Healthcare Japan Corp.) column (1 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. A urethane linkage-type PEG (20k) adrenomedullin derivative (CH₃O-PEG (20k)-CO—$^{\alpha}$NH-(h.AM (1-52))) (14) and unreacted h.AM (1-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% CH₃CN containing 80 mM Na₂SO₄, flow rate: 0.5 mL/min). The preparative HPLC yielded 250 μg (based on h.AM (1-52)) of the compound (14) of interest.

Experiment I-1-15: Synthesis of CH₃O-PEG (5k)-(CH₂)₂—CH₂—$^{\alpha}$NH-(h.AM (1-52)) (Compound (35))

The same procedures as in experiment I-1-3 were carried out except that 5 mg of an aldehyde-type CH₃O-PEGylation reagent (PEG-2) (CH₃O—(CH₂CH₂O)$_n$—(CH₂)₂—CHO) with a weight-average molecular weight of 5 kDa was used instead of the aldehyde-type CH₃O-PEGylation reagent (PEG-2) with a weight-average molecular weight of 10 kDa, to obtain an alkylamine linkage-type PEG (5k) adrenomedullin derivative (CH₃O-PEG (5k)-(CH₂)₂—CH₂—$^{\alpha}$NH-(h.AM (1-52))) (35). Preparative HPLC yielded 0.8 mg (based on h.AM (1-52)) of the compound (35) of interest.

Experiment I-1-16: Synthesis of CH₃O-PEG (40k)-(CH₂)₂—CH₂—$^{\alpha}$NH-(h.AM (1-52)) (Compound (25))

The same procedures as in experiment I-1-3 were carried out except that 40 mg of an aldehyde-type CH₃O-PEGylation reagent (PEG-2) (CH₃O—(CH₂CH₂O)$_n$—(CH₂)₂—CHO) with a weight-average molecular weight of 40 kDa was used instead of the aldehyde-type CH₃O-PEGylation reagent (PEG-2) with a weight-average molecular weight of 10 kDa, to obtain an alkylamine linkage-type PEG (40k) adrenomedullin derivative (CH₃O-PEG (40k)-(CH₂)₂-CH₂—$^{\alpha}$NH-(h.AM (1-52))) (25). Preparative HPLC yielded 0.6 mg (based on h.AM (1-52)) of the compound (25) of interest.

Experiment I-1-17: Synthesis of GL-2-branched CH₃O-PEG (20k)-CO—$^{\alpha}$NH-(h.AM (1-52)) (Compound (26))

The same procedures as in experiment I-1-14 were carried out except that 25 mg of a p-nitrophenyl ester-type CH₃O-PEGylation reagent (PEG-9) with a weight-average molecular weight of 20 kDa represented by formula (XII-1-1'):

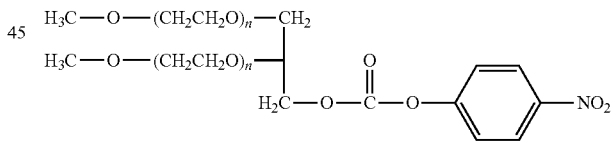

(XII-1-1')

was used instead of the p-nitrophenyl ester-type CH₃O-PEGylation reagent (PEG-8) (CH₃O—(CH₂CH₂O)$_n$—CO—O—C₆H₄-p-NO₂) with a weight-average molecular weight of 20 kDa, to obtain a glycerol skeleton-containing 2-branched urethane linkage-type PEG (20k) adrenomedullin derivative (GL-2-branched CH₃O-PEG (20k)-CO—$^{\alpha}$NH-(h.AM (1-52))) (26):

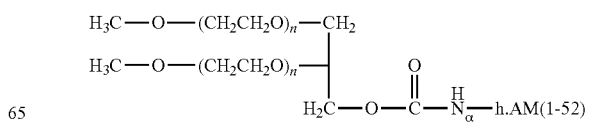

(26)

Preparative HPLC yielded 0.2 mg (based on h.AM (1-52)) of the compound (26) of interest.

Experiment I-1-18: Synthesis of GL-2-branched CH₃O-PEG (40k)-CO—ᵅNH-(h.AM (1-52)) (Compound (27))

The same procedures as in experiment I-1-14 were carried out except that 35 mg of a p-nitrophenyl ester-type CH₃O-PEGylation reagent (PEG-9) with a weight-average molecular weight of 40 kDa represented by formula (XII-1-1'):

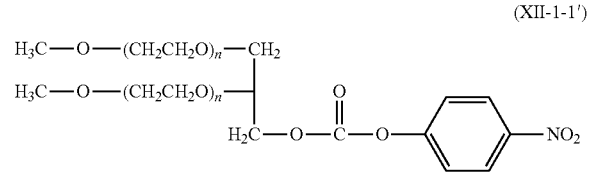
(XII-1-1')

was used instead of the p-nitrophenyl ester-type CH₃O-PEGylation reagent (PEG-8) (CH₃O—(CH₂CH₂O)$_n$—CO—O—C₆H₄-p-NO₂) with a weight-average molecular weight of 20 kDa, to obtain a glycerol skeleton-containing 2-branched urethane linkage-type PEG (40k) adrenomedullin derivative (GL-2-branched CH₃O-PEG (40k)-CO—ᵅNH-(h.AM (1-52)) (27):

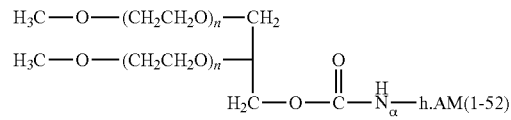
(27)

Preparative HPLC yielded 0.2 mg (based on h.AM (1-52)) of the compound (27) of interest.

Experiment I-1-19: Synthesis of GL-4-branched CH₃O-PEG (40k)-CO—ᵅNH-(h.AM (1-52)) (Compound (28))

The same procedures as in experiment I-1-14 were carried out except that 40 mg of a p-nitrophenyl ester-type CH₃O-PEGylation reagent (PEG-10) with a weight-average molecular weight of 40 kDa represented by formula (XII-2-1'):

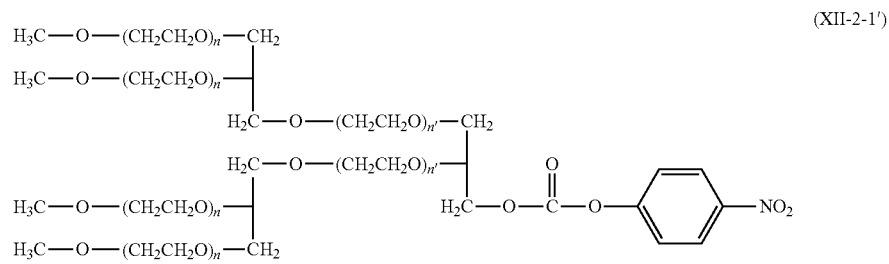
(XII-2-1')

was used instead of the p-nitrophenyl ester-type CH₃O-PEGylation reagent (PEG-8) (CH₃O—(CH₂CH₂O)$_n$—CO—O—C₆H₄-p-NO₂) with a weight-average molecular weight of 20 kDa, to obtain a glycerol skeleton-containing 4-branched urethane linkage-type PEG (40k) adrenomedullin derivative (GL-4-branched CH₃O-PEG (40k)-CO—ᵅNH-(h.AM (1-52)) (28):

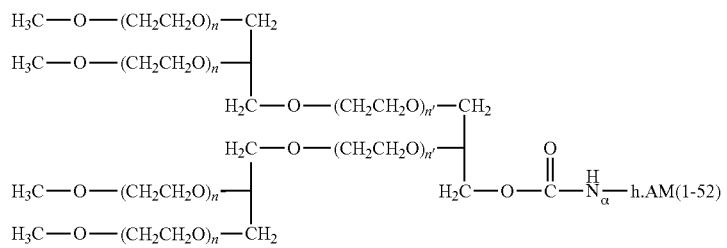
(28)

Preparative HPLC yielded 0.2 mg (based on h.AM (1-52)) of the compound (28) of interest.

Experiment I-2: Structural Analysis of Full-Length Adrenomedullin Derivative

Experiment I-2-1: Identification of Binding Position to PEG Group by Mass Spectrometry of Cleaved Peptide-(1)

10 µg of the compound (3) was mixed with 70% formic acid and 600 µg of cyanogen bromide (BrCN) to adjust the total amount to 500 µL. This mixture was reacted overnight at room temperature. 1 mL each of chloroform, methanol, and a 60% aqueous acetonitrile solution containing 0.1% trifluoroacetic acid were applied, in order, to Sep Pak (Waters Corp.) column, and the column was washed. Then, the Sep Pak column was equilibrated by the application of 1 mL of ultrapure water. To the cyanogen bromide-treated reaction solution (500 µL) reacted overnight, 4,500 µL of ultrapure water was added to obtain 5 mL of a diluted reaction solution. The diluted reaction solution was applied to the column for adsorption of a cleaved peptide. Then, 1 mL each of ultrapure water and a 10% aqueous acetonitrile solution containing 0.1% trifluoroacetic acid were applied, in order, to the column, and the column was washed to remove unadsorbed substances. Finally, 1 mL of a 60% aqueous acetonitrile solution containing 0.1% trifluoroacetic acid was applied to the column to elute the cleaved peptide from the column.

The acetonitrile was distilled off under reduced pressure from the eluted fraction of the cleaved peptide thus obtained from the Sep Pak column. The obtained residue was purified and fractionated by reverse-phase HPLC (RP-HPLC) using a reverse-phase column (ODS-120A TSKgel, Tosoh Corp.). The elution in RP-HPLC was carried out under a linear gradient program of changing from 100% solution A (10% aqueous acetonitrile solution containing 0.1% trifluoroacetic acid) to 100% solution B (60% aqueous acetonitrile solution containing 0.1% trifluoroacetic acid) over 60 minutes. The MS spectrum of the separated cleaved peptide was measured using a mass spectrometry apparatus (AXIMA-confidence, Shimadzu Corp.). As a result, the molecular weight of the cleaved peptide was confirmed to agree with the molecular weight of a peptide corresponding to amino acid residues 6 to 52 of human adrenomedullin ((M+Na)$^+$, calcd: m/z 5385.935; found: m/z 5385.9986). All lysine residues (residues 25, 36, 38 and 46 from the N terminus) present in human adrenomedullin are located within the range from amino acid residues 6 to 52. From these results, therefore, the PEG group in the alkylamine linkage-type PEG (10k) adrenomedullin derivative (3) was confirmed to be attached to the N-terminal α-amino group.

Experiment I-2-2: Identification of Binding Position to PEG Group by Mass Spectrometry of Cleaved Peptide-(2)

10 to 40 µg of the compound (2) was dissolved in 500 µL of a solution containing 2.5 mM ethylenediaminetetraacetic acid, 30% N,N-dimethylformamide and 250 mM Tris-HCl (pH 8.5), and the solution was stirred and mixed by a vortex mixer and ultrasonication. To the mixture, 2.5 mg of 1,4-dithiothreitol was added, and the resulting mixture was confirmed to have pH of 8.0 or higher. To the mixture, nitrogen gas was injected, followed by ultrasonication for 5 minutes. This mixture was reacted at 37° C. for 2 hours. To the reaction mixture thus reacted, 6.25 mg of monoiodoacetic acid was added in the dark, and the mixture was further reacted at 25° C. for 30 minutes. Then, the reaction was terminated by the addition of acetic acid (final concentration: 1 N) to the reaction mixture. 1 mL each of chloroform, methanol, and a 60% aqueous acetonitrile solution containing 0.1% trifluoroacetic acid were applied, in order, to Sep Pak (Waters Corp.) column, and the column was washed. Then, the Sep Pak column was equilibrated by the application of 1 mL of 1 N acetic acid. The reductively alkylated reaction solution was applied to the column for adsorption of a reacted peptide. Then, 1 mL each of 1 N acetic acid and a 10% aqueous acetonitrile solution containing 0.1% trifluoroacetic acid were applied, in order, to the column, and the column was washed to remove unadsorbed substances. Finally, 1 mL of a 60% aqueous acetonitrile solution containing 0.1% trifluoroacetic acid was applied to the column to elute the reductively alkylated peptide from the column.

Figure 4:
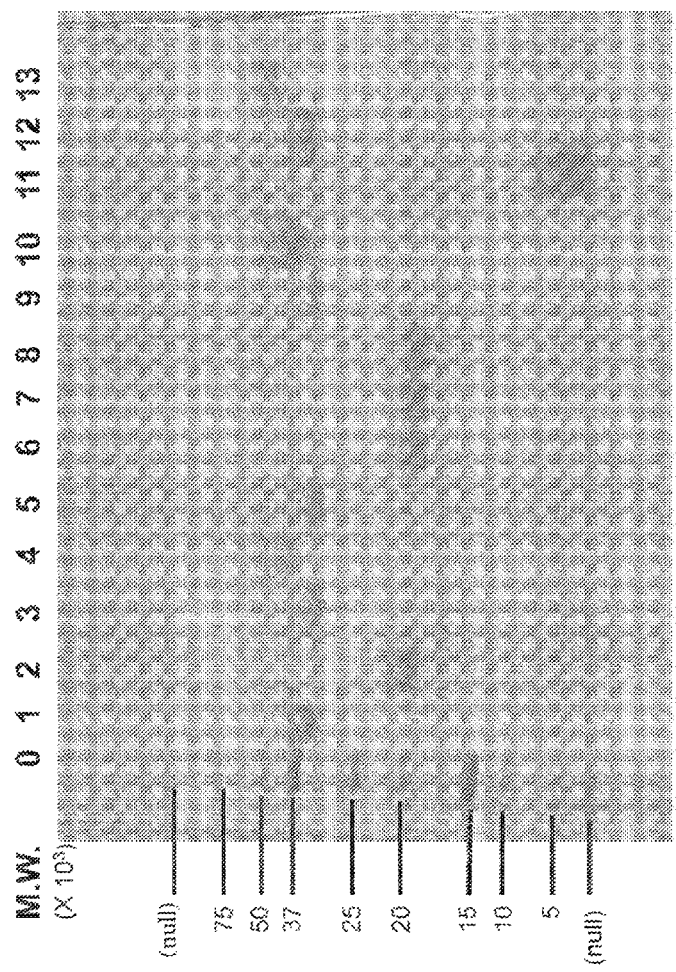
FIG. 4 shows results of separating compounds (25), (26), (27), (28), (29), (30), (31), (32), (33), (34), (35), (36) and (37) by SDS-PAGE using a polyacrylamide gel with a concentration gradient from 10% to 20%. In the diagram, lane 0 depicts a molecular weight standard, lane 1 depicts the compound (25), lane 2 depicts the compound (26), lane 3 depicts the compound (27), lane 4 depicts the compound (28), lane 5 depicts the compound (29), lane 6 depicts the compound (30), lane 7 depicts the compound (31), lane 8 depicts the compound (32), lane 9 depicts the compound (33), lane 10 depicts the compound (34), lane 11 depicts the compound (35), lane 12 depicts the compound (36), and lane 13 depicts the compound (37).

The acetonitrile was distilled off under reduced pressure from the eluted fraction of the reductively alkylated peptide thus obtained from the Sep Pak column. The obtained reductively alkylated peptide was mixed with lysyl endopeptidase at a peptide:lysyl endopeptidase mass ratio of 20:1. To the mixture, 1 M Tris-HCl (pH 8.5) was added to adjust the volume to 200 µL and the final concentration of Tris-HCl to 50 mM. This mixture was left overnight (16 hours or longer) at 37° C. The obtained cleaved peptide was purified and separated by RP-HPLC using a reverse-phase column (ODS-120A TSKgel, Tosoh Corp.). The elution in RP-HPLC was carried out under a program of applying 100% solution A (0.1% trifluoroacetic acid) for 5 minutes, then applying an eluent under linear gradient conditions involving changing from the 100% solution A to 50% solution B (60% aqueous acetonitrile solution containing 0.1% trifluoroacetic acid) over 60 minutes, and further applying 100% solution B for 15 minutes. Reactions and preparative RP-HPLC were carried out by the same procedures as above using a chemically synthesized h.AM (1-52) peptide preparation as a control instead of the compound (2). FIG. 1 shows the RP-HPLC chromatogram of the cleaved peptide. FIG. 1A shows the RP-HPLC chromatogram of the cleaved peptide derived from the h.AM (1-52) peptide, and FIG. 1B shows the RP-HPLC chromatogram of the cleaved peptide derived from the compound (2). As shown in FIG. 1A, 4 major peaks were detected at retention times of 28.08 minutes (hereinafter, also described as "peak (1)"), 36.97 minutes (hereinafter, also described as "peak (2)"), 54.53 minutes (hereinafter, also described as "peak (3)"), and 67.52 minutes (hereinafter, also described as "peak (4)") in the RP-HPLC chromatogram of the cleaved peptide derived from the h.AM (1-52) peptide. On the other hand, as shown in FIG. 1B, 4 major peaks were detected at retention times of 28.69 minutes (hereinafter, also described as "peak (5)"), 36.98 minutes (hereinafter, also described as "peak (6)"), 54.57 minutes (hereinafter, also described as "peak (7)"), and 72.30 minutes (hereinafter, also described as "peak (8)") in the RP-HPLC chromatogram of the cleaved peptide derived from the compound (2). From the comparison of the retention times, the peaks (1) and (5), the peaks (2) and (6), or the peaks (3) and (7) correspond to the same peptide fragment. The peaks (4) and (8) differ in retention time. The compound of the peak (8) is presumed to be a compound having a PEG group attached to the peptide fragment of the peak (4).

Reactions and preparative RP-HPLC were carried out by the same procedures as above using the compounds (7), (8)

and (26). As a result, peaks having retention times corresponding to the peaks (1), (2) and (3) were detected, as in the case of using the compound (2). Also, a peak presumed to correspond to a compound having a PEG group attached to the peptide fragment of the peak (4) was detected, as in the peak (8).

The MS spectrum of the separated cleaved peptide was measured using a mass spectrometry apparatus (QSTAR Elite, AB Sciex Pte. Ltd). Human adrenomedullin has 4 lysine residues (residues 25, 36, 38 and 46 from the N terminus). Therefore, the cleaved peptide obtained by lysyl endopeptidase consists of 5 peptide fragments, specifically, peptide fragments of YRQSMNNFQGLRSFGCRFGTCTVQK (h.AM (1-25)), LAHQIYQFTAK (h.AM (26-36)), DK (h.AM (37-38)), DNVAPRSK (h.AM (39-46)), and ISPQGY (h.AM (47-52)) from the N terminus. From the obtained MS spectrum, the peaks (1) and (5) were confirmed to correspond to the peptide fragment of h.AM (39-46), the peaks (2) and (6) were confirmed to correspond to the peptide fragment of h.AM (47-52), the peaks (3) and (7) were confirmed to correspond to the peptide fragment of h.AM (26-36), and the peak (4) was confirmed to correspond to the peptide fragment of h.AM (1-25). As a result of measuring the MS spectrum of the peptide fragment of the peak (8) using a mass spectrometry apparatus (autoflex II, Bruker Daltonics K.K.), the compound of the peak (8) was confirmed to be a compound having a PEG group attached to the N-terminal peptide fragment of the h.AM (1-52) peptide. From these results, therefore, all the PEG groups in the compounds (7), (8) and (26) were confirmed to be attached to the N-terminal α-amino groups.

Experiment I-2-3: Identification of Binding Position to PEG Group by Amino Acid Sequence Analysis The compounds (3), (4), (5), (6), (7), (8), (9), (10), (11), (12) and (13) were subjected to amino acid sequence analysis using a protein sequencer (Procise 494 HT Protein Sequencing System, Applied Biosystems, Inc.). As a result, an amino acid corresponding to the N-terminal amino acid residue of human adrenomedullin was detected in none of the compounds. From these results, all the PEG groups in the compounds (3), (4), (5), (6), (7), (8), (9), (10), (11), (12) and (13) were confirmed to be attached to the N-terminal α-amino groups.

Experiment I-2-4: Identification of Binding Position to PEG Group by Ion-Exchange HPLC The peptide corresponding to amino acid residues 6 to 52 of human adrenomedullin was separated from the h.AM (1-52) peptide by ion-exchange HPLC using an ion-exchange column (CM-2SW, Tosoh Corp.). The elution in ion-exchange HPLC was carried out under a linear gradient program of changing from 80% solution A (100 mM sodium acetate, pH 5.0) and 20% solution B (100 mM sodium acetate containing 1 M sodium sulfate, pH 7.0) to 20% solution A and 80% solution B from 0 to 40 minutes.

The acetonitrile was distilled off under reduced pressure from the eluted fraction of the cleaved peptide of the compound (3) obtained from the Sep Pak column in experiment I-2-1. The residue was analyzed by ion-exchange HPLC under the conditions described above. As a result, a peak having the same elution time as that of the peptide corresponding to amino acid residues 6 to 52 of human adrenomedullin was confirmed as to the compound (3). The acetonitrile was distilled off under reduced pressure from the eluted fractions of the cleaved peptides of the compounds (4), (5), (6), (7), (8), (9), (10), (11), (12), (13), (25), (27), (28) and (35) obtained by the same procedures as in experiment I-2-1 from the Sep Pak column. As a result of analyzing the residues by ion-exchange HPLC under the conditions described above, their peaks were confirmed to agree with the peak of the compound (3). From these results, therefore, all the PEG groups in the compounds (3), (4), (5), (6), (7), (8), (9), (10), (11), (12), (13), (25), (27), (28) and (35) were confirmed to be attached to the N-terminal α-amino groups.

Experiment I-2-5: Molecular Weight Analysis by SDS-PAGE

Figure 2:
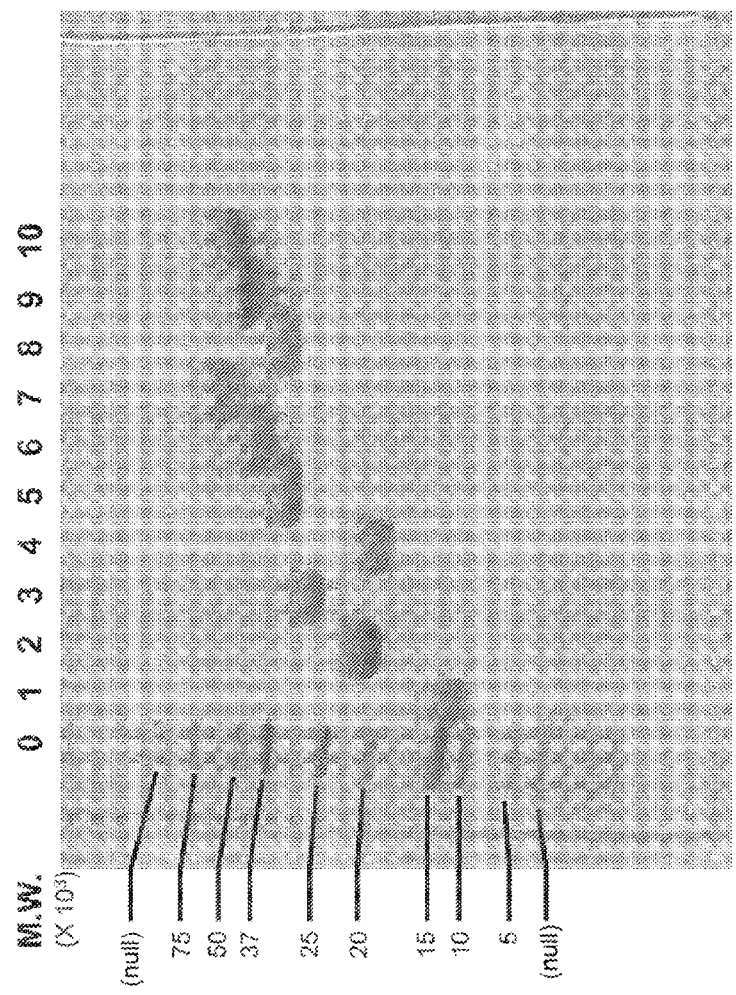
FIG. 2 shows results of separating compounds (3), (4), (5), (6), (7), (8), (9), (10), (11) and (12) by SDS-PAGE using a polyacrylamide gel with a concentration gradient from 10% to 20%. In the diagram, lane 0 depicts a molecular weight standard, lane 1 depicts the compound (3), lane 2 depicts the compound (4), lane 3 depicts the compound (5), lane 4 depicts the compound (6), lane 5 depicts the compound (7), lane 6 depicts the compound (8), lane 7 depicts the compound (9), lane 8 depicts the compound (10), lane 9 depicts the compound (11), and lane 10 depicts the compound (12).
Figure 3:
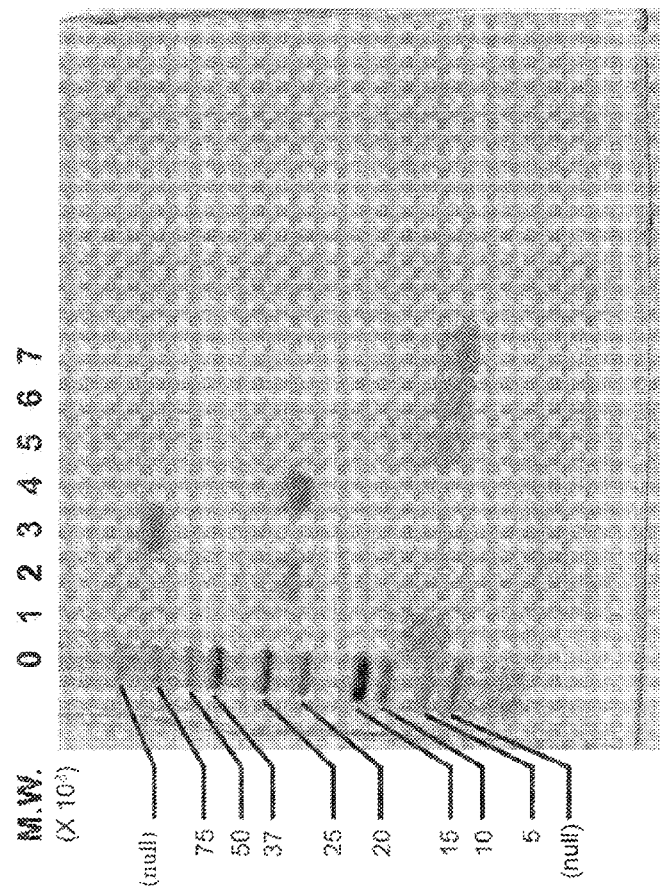
FIG. 3 shows results of separating compounds (1), (2), (13), (14), (15), (16) and (17) by SDS-PAGE using a polyacrylamide gel with a concentration gradient from 10% to 20%. In the diagram, lane 0 depicts a molecular weight standard, lane 1 depicts the compound (1), lane 2 depicts the compound (2), lane 3 depicts the compound (13), lane 4 depicts the compound (14), lane 5 depicts the compound (15), lane 6 depicts the compound (16), and lane 7 depicts the compound (17).

In accordance with the laboratory textbook (Experimental Medicine, Suppl., "Handbook for Protein Experiments", Yodosha Co., Ltd., edited by Tadaomi Takenawa and Toshiki Ito), the compounds (1), (2), (3), (4), (5), (6), (7), (8), (9), (10), (11), (12), (13), (14), (25), (26), (27), (28) and (35) (200 ng each) obtained in experiment I-1 were separated by SDS-PAGE using a polyacrylamide gel with a concentration gradient from 10% to 20%. The results are shown in FIGS. 2, 3 and 4. In FIG. 2, lane 0 depicts a molecular weight standard, lane 1 depicts the compound (3), lane 2 depicts the compound (4), lane 3 depicts the compound (5), lane 4 depicts the compound (6), lane 5 depicts the compound (7), lane 6 depicts the compound (8), lane 7 depicts the compound (9), lane 8 depicts the compound (10), lane 9 depicts the compound (11), and lane 10 depicts the compound (12). In FIG. 3, lane 0 depicts a molecular weight standard, lane 1 depicts the compound (1), lane 2 depicts the compound (2), lane 3 depicts the compound (13), lane 4 depicts the compound (14), lane 5 depicts compound (15) mentioned later, lane 6 depicts compound (16) mentioned later, and lane 7 depicts compound (17) mentioned later. In FIG. 4, lane 0 depicts a molecular weight standard, lane 1 depicts the compound (25), lane 2 depicts the compound (26), lane 3 depicts the compound (27), lane 4 depicts the compound (28), lane 5 depicts compound (29) mentioned later, lane 6 depicts compound (30) mentioned later, lane 7 depicts compound (31) mentioned later, lane 8 depicts compound (32) mentioned later, lane 9 depicts compound (33) mentioned later, lane 10 depicts compound (34) mentioned later, lane 11 depicts the compound (35), lane 12 depicts compound (36) mentioned later, and lane 13 depicts compound (37) mentioned later. All the molecular weight standards used were Precision Plus Protein™ Dual Xtra Standards (Bio-Rad Laboratories, Inc.). As shown in FIGS. 2, 3 and 4, each compound was confirmed to have the desired molecular weight.

Experiment I-2-6: Confirmation of Association by Gel Filtration HPLC

Association of adrenomedullin derivative molecules was confirmed by gel filtration HPLC using a gel filtration column (Superdex 200 Increase 10/300 GL, GE Healthcare Japan Corp.). The compounds (3), (4), (5), (6), (7), (8), (9), (10), (11), (12), (13), (25), (27), (28), and (35) (50 µg each) obtained in experiment I-1 were added to the column. An eluent (100 mM sodium acetate and 100 mM sodium sulfate, pH 6.0) was applied to the column at a flow rate of 0.75 ml/min. From the obtained gel filtration chromatogram, each compound exhibited a single peak having a retention time appropriate for the molecular weight. From these results, each adrenomedullin derivative molecule was confirmed to be present as a monomer without being associated. The retention time of each compound in the gel filtration chromatogram is shown in Table 1.

TABLE 1

| Adrenomedullin derivative | Retention time (min) |
| --- | --- |
| Compound (3) | 18.6 |
| Compound (4) | 16.2 |
| Compound (5) | 14.6 |
| Compound (6) | 16.4 |
| Compound (7) | 13.7 |
| Compound (8) | 12.9 |
| Compound (9) | 11.9 |
| Compound (10) | 13.8 |
| Compound (11) | 14.1 |
| Compound (12) | 14.4 |
| Compound (13) | 13.3 |
| Compound (25) | 13.9 |
| Compound (27) | 13.9 |
| Compound (28) | 14.5 |
| Compound (35) | 21.2 |

Experiment II: Preparation of N-Terminally Deleted Adrenomedullin Derivative

Experiment II-1: Synthesis of N-Terminally Deleted Adrenomedullin Derivative

Experiment II-1-1: Synthesis of $CH_3O$-PEG (5k)-$(CH_2)_5$—CO—$^\alpha$NH-(h.AM (6-52)) (Compound (15))

In accordance with the method described in the known literature (Kubo, K et al., "Biological properties of adrenomedullin conjugated with polyethylene glycol.", Peptides, 2014, vol. 57, p. 118-21), a polyethylene glycol group with a weight-average molecular weight of 5 kDa (PEG (5k)) was linked via an amide bond to the N-terminal amino group of a $Cys^{16}$-$Cys^{21}$ disulfide bridge form of a peptide having the amino acid sequence of H-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val- Ala-Pro-Arg-Ser-Lys-Ile-Ser-Pro-Gln-Gly-Tyr-$NH_2$ (hereinafter, also described as "h.AM (6-52)"), which was a peptide corresponding to amino acid residues 6 to 52 of human adrenomedullin, using a N-hydroxysuccinimide active ester-type $CH_3O$-PEGylation reagent (PEG-1) ($CH_3O$—$(CH_2CH_2O)_n$—$(CH_2)_5$—CO—O—NHS) of 5 kDa to synthesize an amide linkage-type PEG (5k) adrenomedullin derivative ($CH_3O$-PEG (5k)-$(CH_2)_5$—CO—$^\alpha$NH-(h.AM (6-52))) (15).

Experiment II-1-2: Synthesis of $CH_3O$-PEG (5k)-$(CH_2)_5$—CO—$^\alpha$NH-(h.AM (11-52)) (Compound (16))

In the same way as in experiment II-1-1, a polyethylene glycol group with a weight-average molecular weight of 5 kDa (PEG (5k)) was linked via an amide bond to the N-terminal amino group of a $Cys^{16}$-$Cys^{21}$ disulfide bridge form of a peptide having the amino acid sequence of H-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-$NH_2$ (hereinafter, also described as "h.AM (11-52)"), which was a peptide corresponding to amino acid residues 11 to 52 of human adrenomedullin, using a N-hydroxysuccinimide active ester-type $CH_3O$-PEGylation reagent (PEG-1) ($CH_3O$—$(CH_2CH_2O)_n$—$(CH_2)_5$—CO—O—NHS) of 5 kDa to synthesize an amide linkage-type PEG (5k) adrenomedullin derivative ($CH_3O$-PEG (5k)-$(CH_2)_5$—CO—$^\alpha$NH-(h.AM (11-52))) (16).

Experiment II-1-3: Synthesis of $CH_3O$-PEG (5k)-$(CH_2)_5$—CO—$^\alpha$NH-(h.AM (16-52)) (Compound (17))

In the same way as in experiment II-1-1, a polyethylene glycol group with a weight-average molecular weight of 5 kDa (PEG (5k)) was linked via an amide bond to the N-terminal amino group of a $Cys^{16}$-$Cys^{21}$ disulfide bridge form of a peptide having the amino acid sequence of H-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-$NH_2$ (hereinafter, also described as "h.AM (16-52)"), which was a peptide corresponding to amino acid residues 16 to 52 of human adrenomedullin, using a N-hydroxysuccinimide active ester-type $CH_3O$-PEGylation reagent (PEG-1) ($CH_3O$—$(CH_2CH_2O)_n$—$(CH_2)_5$—CO—O—NHS) of 5 kDa to synthesize an amide linkage-type PEG (5k) adrenomedullin derivative ($CH_3O$-PEG (5k)-$(CH_2)_5$—CO—$^\alpha$NH-(h.AM (16-52))) (17).

Experiment II-1-4: Synthesis of $CH_3O$-PEG (5k)-$(CH_2)_2$—$CH_2$—$^\alpha$NH-(h.AM (6-52)) (Compound (18))

0.4 mg of the h.AM (6-52) peptide was dissolved in a 100 mM sodium acetate buffer (pH 5.5) to obtain 0.5 mL of a peptide solution. To this peptide solution, 2 mg of an aldehyde-type $CH_3O$-PEGylation reagent (PEG-2) ($CH_3O$—$(CH_2CH_2O)_n$—$(CH_2)_2$—CHO) with a weight-average molecular weight of 5 kDa was added under ice cooling. To this peptide solution, $NaCNBH_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (5k) adrenomedullin derivative ($CH_3O$-PEG (5k)-$(CH_2)_2$—$CH_2$—$^\alpha$NH-(h.AM (6-52))) (18) and unreacted h.AM (6-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% $CH_3CN$ containing 80 mM $Na_2SO_4$, flow rate: 0.5 mL/min). The preparative HPLC yielded 0.12 mg (based on h.AM (6-52)) of the compound (18) of interest.

Experiment II-1-5: Synthesis of $CH_3O$-PEG (5k)-$(CH_2)_2$—$CH_2$—$^\alpha$NH-(h.AM (11-52)) (Compound (19))

0.44 mg of the h.AM (11-52) peptide was dissolved in a 100 mM sodium acetate buffer (pH 5.5) to obtain 0.5 mL of a peptide solution. To this peptide solution, 2.5 mg of an aldehyde-type CH$_3$O-PEGylation reagent (PEG-2) (CH$_3$O—(CH$_2$CH$_2$O)$_n$—(CH$_2$)$_2$—CHO) with a weight-average molecular weight of 5 kDa was added under ice cooling. To this peptide solution, NaCNBH$_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (5k) adrenomedullin derivative (CH$_3$O-PEG (5k)-(CH$_2$)$_2$—CH$_2$—$^\alpha$NH-(h.AM (11-52))) (19) and unreacted h.AM (11-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% CH$_3$CN containing 80 mM Na$_2$SO$_4$, flow rate: 0.5 mL/min). The preparative HPLC yielded 0.1 mg (based on h.AM (11-52)) of the compound (19) of interest.

Experiment II-1-6: Synthesis of CH$_3$O-PEG (5k)-(CH$_2$)$_2$—CH$_2$—$^\alpha$NH-(h.AM (16-52)) (Compound (20))

0.46 mg of the h.AM (16-52) peptide was dissolved in a 100 mM sodium acetate buffer (pH 5.5) to obtain 0.5 mL of a peptide solution. To this peptide solution, 3 mg of an aldehyde-type CH$_3$O-PEGylation reagent (PEG-2) (CH$_3$O—(CH$_2$CH$_2$O)$_n$—(CH$_2$)$_2$—CHO) with a weight-average molecular weight of 5 kDa was added under ice cooling. To this peptide solution, NaCNBH$_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (5k) adrenomedullin derivative (CH$_3$O-PEG (5k)-(CH$_2$)$_2$—CH$_2$—$^\alpha$NH-(h.AM (16-52))) (20) and unreacted h.AM (16-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% CH$_3$CN containing 80 mM Na$_2$SO$_4$, flow rate: 0.5 mL/min). The preparative HPLC yielded 0.15 mg (based on h.AM (16-52)) of the compound (20) of interest.

Experiment II-1-7: Synthesis of CH$_3$O-PEG (20k)-(CH$_2$)$_2$—CH$_2$—$^\alpha$NH-(h.AM (6-52)) (Compound (21))

0.22 mg of the h.AM (6-52) peptide was dissolved in a 100 mM sodium acetate buffer (pH 5.5) to obtain 0.2 mL of a peptide solution. To this peptide solution, 4.1 mg of an aldehyde-type CH$_3$O-PEGylation reagent (PEG-2) (CH$_3$O—(CH$_2$CH$_2$O)$_n$—(CH$_2$)$_2$—CHO) with a weight-average molecular weight of 20 kDa was added under ice cooling. To this peptide solution, NaCNBH$_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (20k) adrenomedullin derivative (CH$_3$O-PEG (20k)-(CH$_2$)$_2$—CH$_2$—$^\alpha$NH-(h.AM (6-52))) (21) and unreacted h.AM (6-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% CH$_3$CN containing 80 mM Na$_2$SO$_4$, flow rate: 0.5 mL/min). The preparative HPLC yielded 0.1 mg (based on h.AM (6-52)) of the compound (21) of interest.

Experiment II-1-8: Synthesis of CH$_3$O-PEG (20k)-(CH$_2$)$_2$—CH$_2$—$^\alpha$NH-(h.AM (11-52)) (Compound (22))

0.22 mg of the h.AM (11-52) peptide was dissolved in a 100 mM sodium acetate buffer (pH 5.5) to obtain 0.2 mL of a peptide solution. To this peptide solution, 4.6 mg of an aldehyde-type CH$_3$O-PEGylation reagent (PEG-2) (CH$_3$O—(CH$_2$CH$_2$O)$_n$—(CH$_2$)$_2$—CHO) with a weight-average molecular weight of 20 kDa was added under ice cooling. To this peptide solution, NaCNBH$_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (20k) adrenomedullin derivative (CH$_3$O-PEG (20k)-(CH$_2$)$_2$—CH$_2$—$^\alpha$NH-(h.AM (11-52))) (22) and unreacted h.AM (11-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% CH$_3$CN containing 80 mM Na$_2$SO$_4$, flow rate: 0.5 mL/min). The preparative HPLC yielded 0.1 mg (based on h.AM (11-52)) of the compound (22) of interest.

Experiment II-1-9: Synthesis of CH$_3$O-PEG (20k)-(CH$_2$)$_2$—CH$_2$—$^\alpha$NH-(h.AM (16-52)) (Compound (23))

0.22 mg of the h.AM (16-52) peptide was dissolved in a 100 mM sodium acetate buffer (pH 5.5) to obtain 0.2 mL of a peptide solution. To this peptide solution, 5.2 mg of an aldehyde-type CH$_3$O-PEGylation reagent (PEG-2) (CH$_3$O—(CH$_2$CH$_2$O)$_n$—(CH$_2$)$_2$—CHO) with a weight-average molecular weight of 20 kDa was added under ice cooling. To this peptide solution, NaCNBH$_3$ was further added so as to attain a final concentration of 20 mM. The reaction solution was left at 4° C. for 24 hours. The obtained reaction solution was diluted 5-fold with a 50 mM sodium acetate buffer (pH 4.0). The diluted reaction solution was applied at a flow rate of 2 mL/hr to SP-Sepharose HP (GE Healthcare Japan Corp.) column (2 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. An alkylamine linkage-type PEG (20k) adrenomedullin derivative (CH$_3$O-PEG (20k)-(CH$_2$)$_2$—CH$_2$—$^\alpha$NH-(h.AM (16-52))) (23) and unreacted h.AM (16-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% CH$_3$CN containing 80 mM Na$_2$SO$_4$, flow rate: 0.5 mL/min). The preparative HPLC yielded 0.1 mg (based on h.AM (16-52)) of the compound (23) of interest.

Experiment II-1-10: Synthesis of GL-2-branched CH$_3$O-PEG (40k)-CH$_2$—$^\alpha$NH-(h.AM (16-52)) (Compound (24))

The same procedures as in experiment II-1-6 were carried out except that 20 mg of an aldehyde-type CH$_3$O-PEGylation reagent (PEG-3) with a weight-average molecular weight of 40 kDa represented by formula (VII-1-1'):

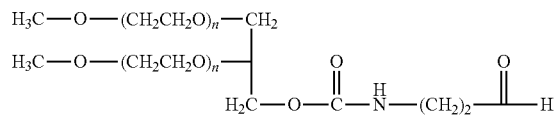
(VII-1-1')

was used instead of the CH$_3$O-PEGylation reagent (PEG-2), to obtain a glycerol skeleton-containing 2-branched alkylamine linkage-type PEG (40k) adrenomedullin derivative (GL-2-branched CH$_3$O-PEG (40k)-CH$_2$—$^\alpha$NH-(h.AM (16-52))) (24):

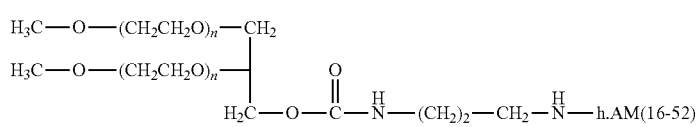
(24)

Preparative HPLC yielded 0.2 mg (based on h.AM (16-52)) of the compound (24) of interest.

Experiment II-1-11: Synthesis of GL-2-branched CH$_3$O-PEG (40k)-CH$_2$—$^\alpha$NH-(h.AM (6-52)) (Compound (29))

The same procedures as in experiment II-1-7 were carried out except that 20 mg of an aldehyde-type CH$_3$O-PEGylation reagent (PEG-3) with a weight-average molecular weight of 40 kDa represented by formula (VII-1-1'):

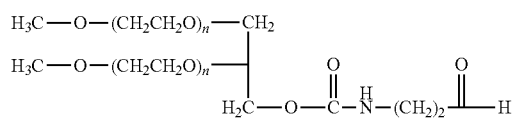
(VII-1-1')

was used instead of the CH$_3$O-PEGylation reagent (PEG-2), to obtain a glycerol skeleton-containing 2-branched alkylamine linkage-type PEG (40k) adrenomedullin derivative (GL-2-branched CH$_3$O-PEG (40k)-CH$_2$—$^\alpha$NH-(h.AM (6-52))) (29):

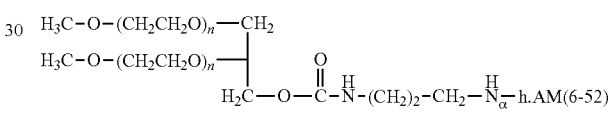
(29)

Preparative HPLC yielded 0.15 mg (based on h.AM (6-52)) of the compound (29) of interest.

Experiment II-1-12: Synthesis of GL-2-Branched CH$_3$O-PEG (20k)-CO—$^\alpha$NH-(h.AM (6-52)) (Compound (30))

A Cys$^{16}$-Cys$^{21}$ disulfide bridge form of a peptide having the amino acid sequence of Fmoc-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-NH$_2$ (hereinafter, also described as "Fmoc—$^\alpha$NH-(h.AM (6-52))") was synthesized by the Fmoc peptide synthesis method. 17 mg of the Fmoc—$^\alpha$NH-(h.AM (6-52)) peptide was dissolved in 1.8 mL of DMSO. To this solution, 9 mg of t-butyl succinimidyl carbonate and 6 μL of diisopropylethylamine were added. The reaction solution was stirred for 5 hours. To the obtained reaction solution, an aqueous acetic acid solution was added. Then, this solution was freeze-dried. The residue was dissolved in 2 mL of DMSO. To the obtained solution, 0.2 mL of diethylamine was added. The obtained solution was stirred for 70 minutes. The reaction solution was diluted by the addition of an aqueous acetic acid solution. The obtained solution was fractionated using reverse-phase HPLC to obtain a fraction containing the h.AM (6-52) peptide. This fraction was freeze-dried to obtain 9 mg of h.AM (6-52) peptide having 4 lysine residues protected with Boc groups as a white powder.

2 mg of the obtained peptide was dissolved in 2 mL of DMSO. To this peptide solution, 15 mg of a p-nitrophenyl ester-type GL2-branched $CH_3O$-PEGylation reagent (PEG-9) with a weight-average molecular weight of 20 kDa represented by formula (XII-1-1'):

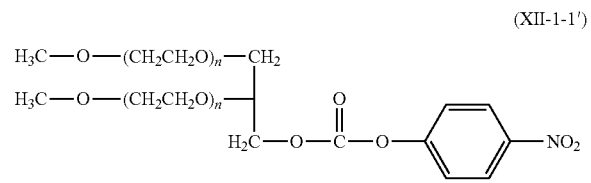

(XII-1-1')

was added under ice cooling. To this peptide solution, 6.5 μL of a 0.1 M solution of triethylamine in DMSO was further added. The reaction solution was left for 1 hour under ice cooling. Then, the reaction solution was brought back to room temperature and left for 24 hours. The temperature of the reaction solution was further raised to 30° C., and the reaction was continued for 2 days. The reaction solution was freeze-dried. To the obtained residue, 1 mL of trifluoroacetic acid was added under ice cooling. The mixture was brought back to room temperature and left for 2 hours. Subsequently, the trifluoroacetic acid was distilled away under reduced pressure from the mixture using an evaporator. The obtained residue was dissolved by the addition of 4 mL of a 50 mM sodium acetate buffer (pH 4.0). This solution was applied at a flow rate of 1 mL/hr to SP-Sepharose HP (GE Healthcare Japan Corp.) column (1 mL) equilibrated with a 50 mM sodium acetate buffer (pH 4.0). The column was washed with 2 mL of a 50 mM sodium acetate buffer (pH 4.0). Subsequently, 5 mL of a 50 mM sodium acetate buffer (pH 5.0) containing 1 M NaCl was applied to the column to obtain an eluted fraction. A glycerol skeleton-containing 2-branched urethane linkage-type PEG (20k) adrenomedullin derivative (GL-2-branched $CH_3O$-PEG (20k)-CO—$^\alpha$NH-(h.AM (6-52))) (30):

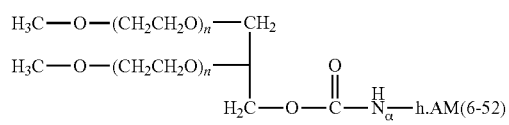

(30)

and unreacted h.AM (6-52) peptide were recovered in the eluted fraction. This eluted fraction was concentrated into 0.2 mL using an ultrafiltration membrane (Amicon Ultra 4, Merck Millipore). The obtained concentrate was purified and fractionated using a HPLC system (L-2000; manufactured by Hitachi High-Tech Science Corp.) connected with Tsk gel G2000SWxL (60 cm, Tosoh Corp.) column (eluent: 80 mM sodium acetate buffer, pH 6+20% $CH_3CN$ containing 80 mM $Na_2SO_4$, flow rate: 0.5 mL/min). The preparative HPLC yielded 0.2 mg (based on h.AM (6-52)) of the compound (30) of interest.

Experiment II-1-13: Synthesis of GL-2-Branched $CH_3O$-PEG (20k)-CO—$^\alpha$NH-(h.AM (11-52)) (Compound (31))

A $Cys^{16}$-$Cys^{21}$ disulfide bridge form of a peptide having the amino acid sequence of Fmoc-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-$NH_2$ (hereinafter, also described as "Fmoc—$^\alpha$NH-(h.AM (11-52))") was synthesized by the Fmoc peptide synthesis method. 6 mg of h.AM (11-52) peptide having 4 lysine residues protected with Boc groups was obtained as a white powder by the same procedures as in experiment II-1-12 using Fmoc—$^\alpha$NH-(h.AM (11-52)).

The same procedures as in experiment II-1-12 were carried out except that the h.AM (6-52) peptide was changed to the h.AM (11-52) peptide obtained as described above, and 20 mg of a p-nitrophenyl ester-type $CH_3O$-PEGylation reagent (PEG-9) with a weight-average molecular weight of 20 kDa represented by formula (XII-1-1'):

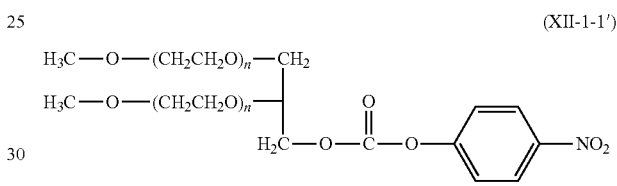

(XII-1-1')

was used, to obtain a glycerol skeleton-containing 2-branched urethane linkage-type PEG (20k) adrenomedullin derivative (GL-2-branched $CH_3O$-PEG (20k)-CO—$^\alpha$NH-(h.AM (11-52))) (31):

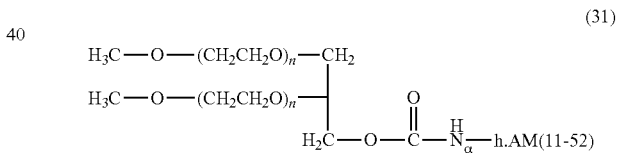

(31)

Preparative HPLC yielded 0.2 mg (based on h.AM (11-52)) of the compound (31) of interest.

Experiment II-1-14: Synthesis of GL-2-Branched $CH_3O$-PEG (20k)-CO—$^\alpha$NH-(h.AM (16-52)) (Compound (32))

A $Cys^{16}$-$Cys^{21}$ disulfide bridge form of a peptide having the amino acid sequence of Fmoc-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-$NH_2$ (hereinafter, also described as "Fmoc—$^\alpha$NH-(h.AM (16-52))") was synthesized by the Fmoc peptide synthesis method. 6 mg of h.AM (16-52) peptide having 4 lysine residues protected with Boc groups was obtained as a white powder by the same procedures as in experiment II-1-12 using Fmoc—$^\alpha$NH-(h.AM (16-52)).

The same procedures as in experiment II-1-12 were carried out except that the h.AM (6-52) peptide was changed to the h.AM (16-52) peptide obtained as described above, and 15 mg of a p-nitrophenyl ester-type $CH_3O$-PEGylation reagent (PEG-9) with a weight-average molecular weight of 20 kDa represented by formula (XII-1-1'):

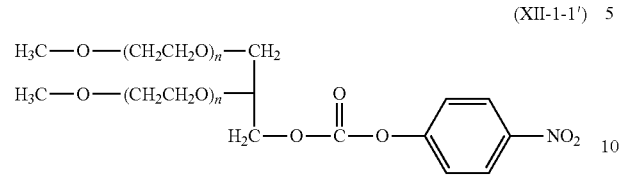

(XII-1-1')

was used, to obtain a glycerol skeleton-containing 2-branched urethane linkage-type PEG (20k) adrenomedullin derivative (GL-2-branched CH$_3$O-PEG (20k)-CO—$^\alpha$NH-(h.AM (16-52))) (32):

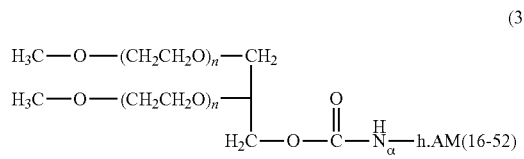

(32)

Preparative HPLC yielded 0.2 mg (based on h.AM (16-52)) of the compound (32) of interest.

Experiment II-1-15: Synthesis of GL-2-Branched CH$_3$O-PEG (40k)-CO—$^\alpha$NH-(h.AM (16-52)) (Compound (33))

The same procedures as in experiment II-1-14 were carried out except that 32 mg of a p-nitrophenyl ester-type CH$_3$O-PEGylation reagent (PEG-9) with a weight-average molecular weight of 40 kDa represented by formula (XII-1-1'):

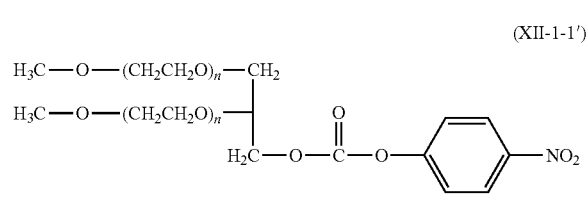

(XII-1-1')

was used instead of the p-nitrophenyl ester-type CH$_3$O-PEGylation reagent (PEG-9) with a weight-average molecular weight of 20 kDa, to obtain a glycerol skeleton-containing 2-branched urethane linkage-type PEG (40k) adrenomedullin derivative (GL-2-branched CH$_3$O-PEG (40k)-CO—$^\alpha$NH-(h.AM (16-52)) (33). Preparative HPLC yielded 0.15 mg (based on h.AM (16-52)) of the compound (33) of interest.

Experiment II-1-16: Synthesis of GL-4-Branched CH$_3$O-PEG (40k)-CO—$^\alpha$NH-(h.AM (6-52)) (Compound (34))

The same procedures as in experiment II-1-12 were carried out except that 20 mg of a p-nitrophenyl ester-type CH$_3$O-PEGylation reagent (PEG-10) with a weight-average molecular weight of 40 kDa represented by formula (XII-2-1'):

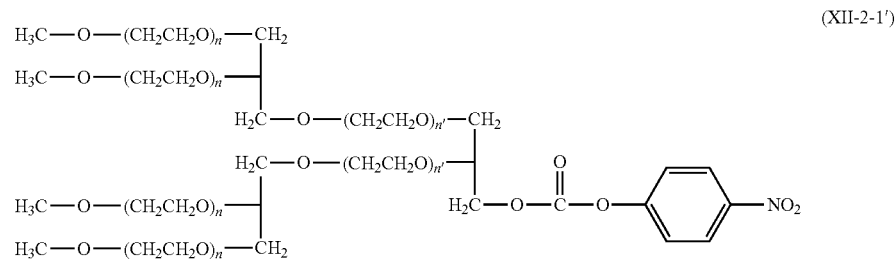

(XII-2-1')

was used instead of the p-nitrophenyl ester-type CH$_3$O-PEGylation reagent (PEG-9) with a weight-average molecular weight of 20 kDa, to obtain a glycerol skeleton-containing 4-branched urethane linkage-type PEG (40k) adrenomedullin derivative (GL-4-branched CH$_3$O-PEG (40k)-CO—$^\alpha$NH-(h.AM (6-52)) (34):

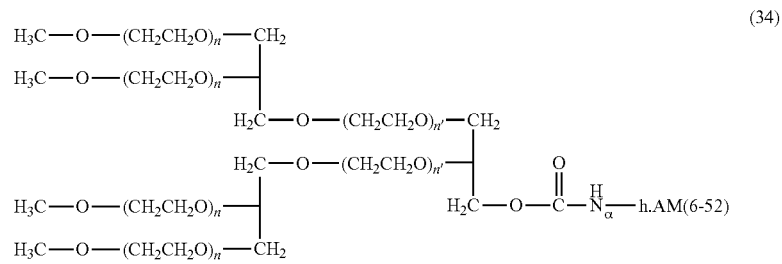

(34)

Preparative HPLC yielded 0.15 mg (based on h.AM (6-52)) of the compound (34) of interest.

Experiment II-2: Structural Analysis of N-Terminally Deleted Adrenomedullin Derivative Experiment II-2-1: Identification of Binding Position to PEG Group by Mass Spectrometry of Cleaved Peptide A cleaved peptide was obtained from the compounds (18), (19), (20), (21), (22), (23), (24), (29), (30), (31), (32), (33) and (34) by the same procedures as in experiment I-2-2 using lysyl endopeptidase. The obtained cleaved peptide was purified and fractionated by RP-HPLC by the same procedures as in experiment I-2-2. As a result, peaks corresponding to the peaks (5), (6), (7) and (8) shown in FIG. 1 were detected in all the RP-HPLC chromatograms of the cleaved peptides derived from the compounds. From the results of experiment I-2-2, the peaks (1) and (5) were confirmed to correspond to the peptide fragment of h.AM (39-46), the peaks (2) and (6) were confirmed to correspond to the peptide fragment of h.AM (47-52), the peaks (3) and (7) were confirmed to correspond to the peptide fragment of h.AM (26-36), the peak (4) was confirmed to correspond to the peptide fragment of h.AM (1-25), and the peak (8) was confirmed to correspond to a compound having a PEG group attached to the N-terminal peptide fragment of the h.AM (1-52) peptide. From these results, therefore, all the PEG groups in the compounds (18), (19), (20), (21), (22), (23), (24), (29), (30), (31), (32), (33) and (34) were confirmed to be attached to the N-terminal α-amino groups.

Experiment II-2-2: Identification of Binding Position to PEG Group by Amino Acid Sequence Analysis The compounds (18), (21), (22), (23), (24), (31), (33) and (34) were subjected to amino acid sequence analysis using a protein sequencer (Procise 494 HT Protein Sequencing System, Applied Biosystems, Inc.). As a result, an amino acid corresponding to the N-terminal amino acid residue of human adrenomedullin was detected in none of the compounds. From these results, all the PEG groups in the compounds (18), (21), (22), (23), (24), (31), (33) and (34) were confirmed to be attached to the N-terminal α-amino groups.

Experiment II-2-3: Molecular Weight Analysis by SDS-PAGE

Figure 5:
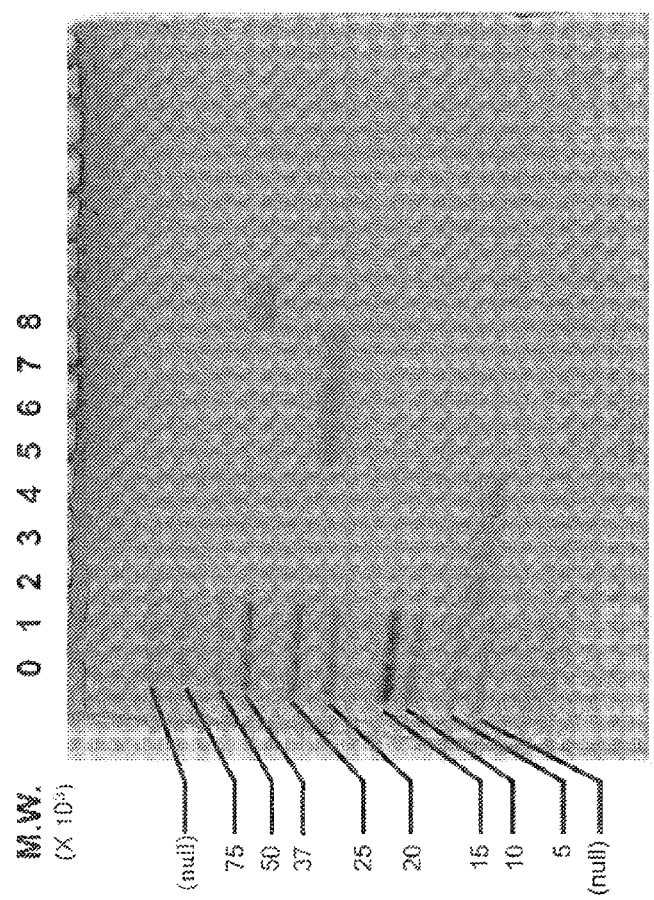
FIG. 5 shows results of separating compounds (18), (19), (20), (21), (22), (23) and (24) by SDS-PAGE using a polyacrylamide gel with a concentration gradient from 10% to 20%. In the diagram, lanes 0 and 1 depict a molecular weight standard, lane 2 depicts the compound (18), lane 3 depicts the compound (19), lane 4 depicts the compound (20), lane 5 depicts the compound (21), lane 6 depicts the compound (22), lane 7 depicts the compound (23), and lane 8 depicts the compound (24).

In accordance with the laboratory textbook (Experimental Medicine, Suppl., "Handbook for Protein Experiments", Yodosha Co., Ltd., edited by Tadaomi Takenawa and Toshiki Ito), the compounds (15), (16), (17), (18), (19), (20), (21), (22), (23), (24), (29), (30), (31), (32), (33) and (34) (200 ng each) obtained in experiment II-1 were separated by SDS-PAGE using a polyacrylamide gel with a concentration gradient from 10% to 20%. The results are shown in FIGS. 3, 4 and 5. In FIG. 3, lane 0 depicts a molecular weight standard, lane 1 depicts the aforementioned compound (1), lane 2 depicts the aforementioned compound (2), lane 3 depicts the aforementioned compound (13), lane 4 depicts the aforementioned compound (14), lane 5 depicts the compound (15), lane 6 depicts the compound (16), and lane 7 depicts the compound (17). In FIG. 4, lane 0 depicts a molecular weight standard, lane 1 depicts the aforementioned compound (25), lane 2 depicts the aforementioned compound (26), lane 3 depicts the aforementioned compound (27), lane 4 depicts the aforementioned compound (28), lane 5 depicts the compound (29), lane 6 depicts the compound (30), lane 7 depicts the compound (31), lane 8 depicts the compound (32), lane 9 depicts the compound (33), lane 10 depicts the compound (34), lane 11 depicts the aforementioned compound (35), lane 12 depicts compound (36) mentioned later, and lane 13 depicts compound (37) mentioned later. In FIG. 5, lane 0 and 1 depict a molecular weight standard, lane 2 depicts the compound (18), lane 3 depicts the compound (19), lane 4 depicts the compound (20), lane 5 depicts the compound (21), lane 6 depicts the compound (22), lane 7 depicts the compound (23), and lane 8 depicts the compound (24). All the molecular weight standards used were Precision Plus Protein™ Dual Xtra Standards (Bio-Rad Laboratories, Inc.). As shown in FIGS. 3, 4 and 5, each compound was confirmed to have the desired molecular weight.

Experiment II-2-4: Confirmation of Association by Gel Filtration HPLC

Association of adrenomedullin derivative molecules was confirmed by gel filtration HPLC using a gel filtration column (Superdex 200 Increase 10/300 GL, GE Healthcare Japan Corp.). The compounds (18), (21), (22), (23), (24), (29) and (34) (50 µg each) obtained in experiment II-1 were added to the column. An eluent (100 mM sodium acetate and 100 mM sodium sulfate, pH 6.0) was applied to the column at a flow rate of 0.75 mL/min. From the obtained gel filtration chromatogram, each compound exhibited a single peak having a retention time appropriate for the molecular weight. From these results, each adrenomedullin derivative molecule was confirmed to be present as a monomer without being associated. The retention time of each compound in the gel filtration chromatogram is shown in Table 2.

TABLE 2

| Adrenomedullin derivative | Retention time (min) |
| --- | --- |
| Compound (18) | 21.4 |
| Compound (21) | 16.2 |
| Compound (22) | 16.2 |
| Compound (23) | 16.2 |
| Compound (24) | 13.9 |
| Compound (29) | 13.9 |
| Compound (34) | 14.5 |

Experiment III: Preparation of C-Terminally Glycine-Extended Adrenomedullin Derivative Experiment III-1: Synthesis of C-Terminally Glycine-Extended Adrenomedullin Derivative Experiment III-1-1: Synthesis of GL-2-Branched $CH_3O$-PEG (40k)-$CH_2$—$^\alpha$NH-(h.AM (1-52))-Gly (Compound (36))

The same procedures as in experiment I-1-5 were carried out except that the h.AM (1-52) peptide was changed to h.AM (1-52)-Gly peptide, and 80 mg of an aldehyde-type $CH_3O$-PEGylation reagent (PEG-3) with a weight-average molecular weight of 40 kDa represented by formula (VII-1-1'):

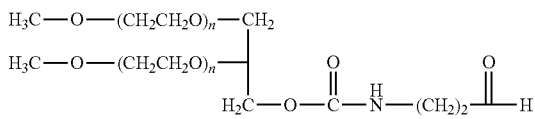
(VII-1-1')

was used instead of the CH₃O-PEGylation reagent (PEG-2), to obtain a glycerol skeleton-containing 2-branched alkylamine linkage-type PEG (40k) adrenomedullin derivative (GL-2-branched CH₃O-PEG (40k)-CH₂—$^\alpha$NH-(h.AM (1-52)-Gly)) (36):

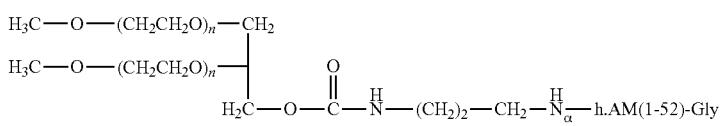
(36)

Preparative HPLC yielded 0.8 mg (based on h.AM (1-52)-Gly) of the compound (36) of interest.

Experiment III-1-2: Synthesis of GL-2-Branched CH₃O-PEG (60k)-CH₂—$^\alpha$NH-(h.AM (1-52))-Gly (Compound (37))

The same procedures as in experiment I-1-5 were carried out except that the h.AM (1-52) peptide was changed to h.AM (1-52)-Gly peptide, and 80 mg of an aldehyde-type CH₃O-PEGylation reagent (PEG-3) with a weight-average molecular weight of 60 kDa represented by formula (VII-1-1'):

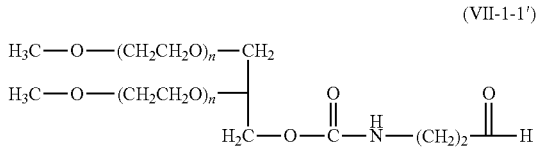
(VII-1-1')

was used instead of the CH₃O-PEGylation reagent (PEG-2), to obtain a glycerol skeleton-containing 2-branched alkylamine linkage-type PEG (60k) adrenomedullin derivative (GL-2-branched CH₃O-PEG (60k)-CH₂—$^\alpha$NH-(h.AM (1-52)-Gly)) (37):

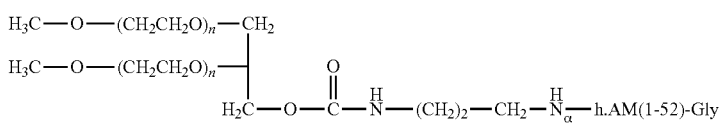
(37)

Preparative HPLC yielded 0.7 mg (based on h.AM (1-52)-Gly) of the compound (37) of interest.

Experiment III-2: Structural Analysis of C-Terminally Glycine-Extended Adrenomedullin Derivative

Experiment III-2-1: Identification of Binding Position to PEG Group by Amino Acid Sequence Analysis The compounds (36) and (37) were subjected to amino acid sequence analysis using a protein sequencer (Procise 494 HT Protein Sequencing System, Applied Biosystems, Inc.). As a result, an amino acid corresponding to the N-terminal amino acid residue of human adrenomedullin was detected in neither of the compounds. From these results, all the PEG groups in the compounds (36) and (37) were confirmed to be attached to the N-terminal α-amino groups.

Experiment IV: Use Examples of Adrenomedullin Derivative

Experiment IV-1: Intracellular cAMP Concentration-Increasing Effect of Adrenomedullin Derivative The physiological effect of adrenomedullin (AM) is known to be exerted via increase in the concentration of intracellular cAMP (see Non Patent Literature 1). Accordingly, each compound prepared in experiments I-1, II-1 and III-1, full-length AM, N-terminally deleted AM, or C-terminally glycine-extended AM was added to a cultured cell line (HEK293 cell line) caused to express an AM receptor, and the amount of intracellular cAMP produced was measured. $10^{-8}$ mol/L of each compound, h.AM (1-52), h.AM (6-52), h.AM (11-52), h.AM (16-52), or h.AM (1-52)-Gly was added to confluent HEK293 cells (cell count: $5 \times 10^4$) in the presence of 0.5 mM IBMX and incubated for 15 minutes. Then, the intracellular cAMP concentration in the HEK293 cells of each test zone was measured using an ELISA kit for cAMP measurement (GE Healthcare Japan Corp., #RPN2251). The intracellular cAMP concentration-increasing effects of the adrenomedullin derivatives on the AM receptor-expressing cultured cells are shown in Table 3.

TABLE 3

| Compound | Intracellular cAMP concentration-increasing effect (%)[1] |
|---|---|
| (1) | 81 |
| (2) | 67 |
| (3) | 101 |
| (4) | 100 |
| (5) | 100 |
| (6) | 91 |
| (7) | 96 |
| (8) | 99 |
| (9) | 94 |
| (10) | 102 |
| (11) | 95 |
| (12) | 81 |
| (13) | 80 |
| (14) | 100 |
| (15) | 101[*] |
| (16) | 16[**] |
| (17) | 9[***] |
| (18) | 90 |
| (19) | 80 |
| (20) | 39 |
| (21) | 98[*] |
| (22) | 97 |
| (23) | 97 |
| (24) | 93[***] |
| (25) | 101 |
| (26) | 99 |
| (27) | 87 |
| (28) | 85 |
| (29) | 77 |
| (30) | 99 |
| (31) | 104 |
| (32) | 96 |
| (33) | 61 |
| (34) | 83 |
| (35) | 91 |
| (36) | 96[****] |
| (37) | 91[****] |

[1] Percentage (%) of the intracellular cAMP concentration obtained by the addition of each compound with respect to the intracellular cAMP concentration obtained by the addition of h.AM (1-52)
[*] Percentage (%) of the intracellular cAMP concentration obtained by the addition of each compound with respect to the intracellular cAMP concentration obtained by the addition of h.AM (6-52)
[**] Percentage (%) of the intracellular cAMP concentration obtained by the addition of each compound with respect to the intracellular cAMP concentration obtained by the addition of h.AM (11-52)
[***] Percentage (%) of the intracellular cAMP concentration obtained by the addition of each compound with respect to the intracellular cAMP concentration obtained by the addition of h.AM (16-52)
[****] Percentage (%) of the intracellular cAMP concentration obtained by the addition of each compound with respect to the intracellular cAMP concentration obtained by the addition of h.AM (1-52)-Gly As shown in Table 3, all the adrenomedullin derivatives tested exhibited an intracellular cAMP concentration-increasing effect at the same level as in the corresponding full-length AM, N-terminally deleted AM, or C-terminally glycine-extended AM without a linked PEG group. Therefore, the adrenomedullin derivatives having the linked PEG group are presumed to maintain bioactivity at the same level as in the parent compound full-length AM, N-terminally deleted AM or C-terminally glycine-extended AM.

In comparison among the adrenomedullin derivative compound (2), compound (4), compound (6) and compound (14) which had the PEG group with the same weight-average molecular weight (20 kDa) and the peptide moiety having the same amino acid sequence (h.AM (1-52)) and differed only in the manner of linking between the PEG group and the peptide moiety, the compound (4) and the compound (6), alkylamine linkage-type PEG (20k) adrenomedullin derivatives, exhibited a higher intracellular cAMP concentration-increasing effect than that of the compound (2), an amide linkage-type PEG (20k) adrenomedullin derivative. Likewise, the compound (14), a urethane linkage-type PEG (20k) adrenomedullin derivative, exhibited a higher intracellular cAMP concentration-increasing effect than that of the compound (2), an amide linkage-type PEG (20k) adrenomedullin derivative.

In comparison among the adrenomedullin derivative compound (15), compound (16) and compound (17), or compound (18), compound (19) and compound (20) which had the PEG group with the same weight-average molecular weight (5 kDa) and the peptide moiety having the same amino acid sequence (h.AM (6-52), h.AM (11-52) or h.AM (16-52)) and differed only in the manner of linking between the PEG group and the peptide moiety, the compound (15), the compound (16) and the compound (17), amide linkage-type PEG (5k) adrenomedullin derivatives, exhibited a significantly decreased intracellular cAMP concentration-increasing effect with increase in the extent of the N-terminal deletion of the peptide moiety. On the other hand, the compound (18), the compound (19) and the compound (20), alkylamine linkage-type PEG (5k) adrenomedullin derivatives, suppressed the influence of N-terminal deletion of the peptide moiety on the intracellular cAMP concentration-increasing effect.

In comparison among the adrenomedullin derivative compound (4), compound (21), compound (22) and compound (23) which had the PEG group with the same weight-average molecular weight (20 kDa) and the same manner of linking between the PEG group and the peptide moiety and differed only in the amino acid sequence of the peptide moiety, the compound (21), the compound (22) and the compound (23), alkylamine linkage-type PEG (20k) adrenomedullin derivatives, exhibited a high intracellular cAMP concentration-increasing effect without the influence of the N-terminal deletion of the peptide moiety on the intracellular cAMP concentration-increasing effect.

Experiment IV-2: Blood Pressure-Lowering Effect of Adrenomedullin Derivative

Figure 6:
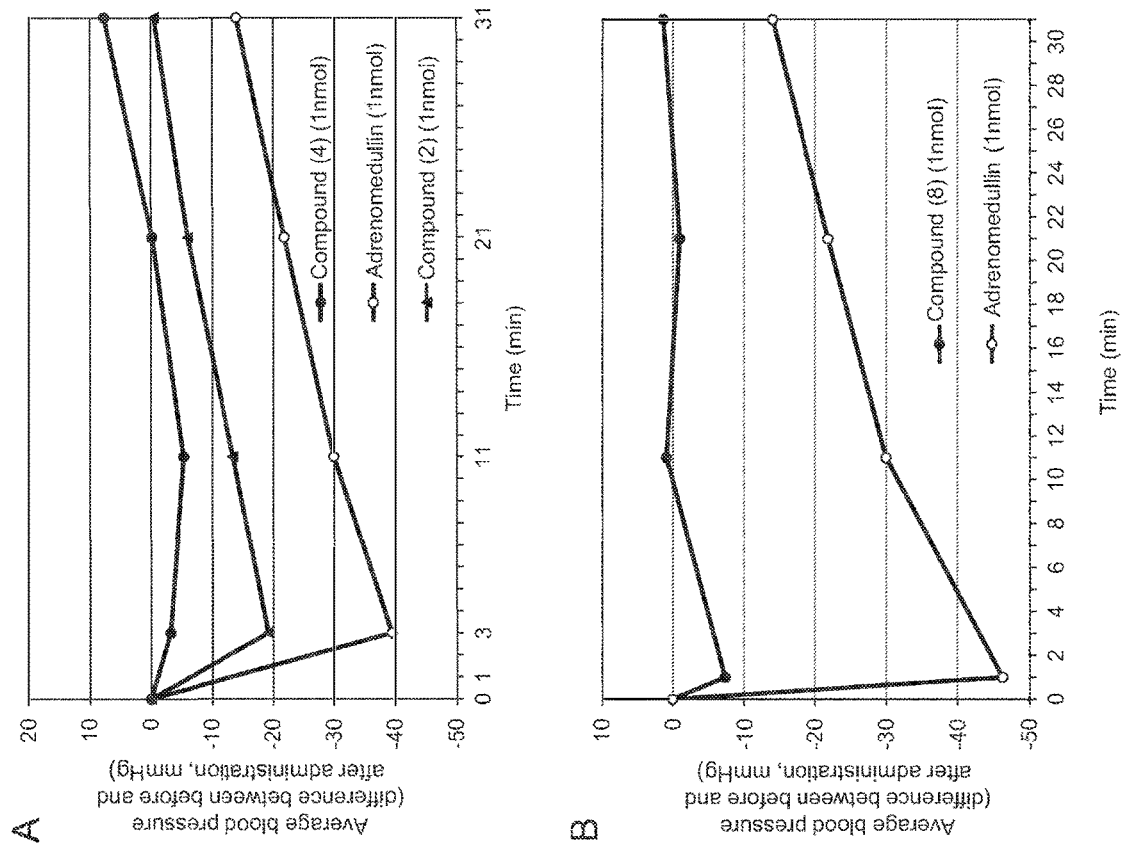
FIG. 6 shows the relationship between the time elapsed from the start of administration of compound (2), compound (4), compound (8) or h.AM (1-52) and the average blood pressure. A: results about the compound (2), the compound (4) and h.AM (1-52); and B: results about the compound (8) and h.AM (1-52).

Each compound prepared in experiments I-1 and II-1 or full-length AM was administered in a single dose of 1 nmol/kg into the vein of each rat under anesthesia, and change in the blood pressure of the rat was observed. Each 11 to 14-week-old male Wistar rat was anesthetized by the inhalation of isoflurane. After tracheotomy, inhalational anesthesia was controlled at an isoflurane concentration of 1.5 to 2.5% and a flow rate of 0.6 to 0.8 L/min. The right jugular vein was isolated from the rat, and a catheter tube corresponding to 26 G was inserted thereto. Next, the left carotid artery was isolated from the rat thus treated, and a catheter tube corresponding to 23 G was inserted thereto. From the catheter tube of the right jugular vein, a physiological saline-heparin solution (physiological saline: 100 mL; heparin: 1000 units) was infused at 2.4 mL/hr. From this catheter tube, 1 nmol/kg of the compound (2), the compound (4), the compound (8) or h.AM (1-52) was administered in a form dissolved in physiological saline. The catheter inserted in the carotid artery was connected to a pressure transducer. The blood pressure before the administration of the compound (2), the compound (4) or h.AM (1-52) and the blood pressure after the administration thereof were measured over time. The relationship between the time elapsed from the start of the administration of the compound (2), the compound (4), the compound (8) or h.AM (1-52) and the average blood pressure is shown in FIG. 6. FIG. 6A shows the results about the compound (2), the compound (4) and h.AM (1-52), and FIG. 6B shows the results about the compound (8) and h.AM (1-52). In the diagram, the ordinate depicts a difference obtained by subtracting the average blood pressure before the administration of each drug from the average blood pressure at the time of the administration of each drug.

As shown in FIG. 6, rapidly decreased blood pressure was observed in full-length AM (h.AM (1-52)) without a linked PEG group immediately after the administration. By contrast, the rapidly decreased blood pressure observed in h.AM (1-52) immediately after the administration was not observed in the adrenomedullin derivatives (compound (2), compound (4) and compound (8)) having the linked PEG group. Therefore, the adrenomedullin derivatives having the linked PEG group are presumed to be able to suppress unwanted side effects such as rapidly decreased blood pressure that may occur in the parent compound full-length AM.

In comparison among the adrenomedullin derivative compound (2), compound (4) and compound (8) which had the PEG group with the same weight-average molecular weight (20 kDa) and the peptide moiety having the same amino acid sequence (h.AM (1-52)) and differed only in the manner of linking between the PEG group and the peptide moiety, the compound (4) and the compound (8), alkylamine linkage-type PEG (20k) adrenomedullin derivatives, further suppressed decrease in the blood pressure immediately after the administration, as compared to the compound (2), an amide linkage-type PEG (20k) adrenomedullin derivative.

Experiment IV-3: Measurement Over Time of Concentration in Blood of Subcutaneously Administered Adrenomedullin Derivative-(1)

The compound (8) prepared in experiment I-1 or full-length AM was subcutaneously administered in a single dose of 10 nmol/kg to each rat, and time-dependent change in the concentration in blood of the adrenomedullin derivative was observed. The compound (8) or h.AM (1-52) dissolved in physiological saline was subcutaneously administered to each 7- to 8-week-old male Wistar rat (approximately 250 g). 1 day, 7 days and 10 days after the start of the administration, 50 mg of pentobarbital was intraperitoneally administered, and 300 μL of blood was collected each time from the tail vain under anesthesia. Immediately, 300 μg of EDTA-2Na and 21 μg of aprotinin were added to the obtained blood sample, and the mixture was centrifuged under conditions involving 10 minutes and 3000 rpm to obtain plasma. The AM concentration in the plasma of each sample was measured by radioimmunoassay (RIA) (Kitamura K, Ichiki Y, Tanaka M et al., Immunoreactive adrenomedullin in human plasma. FEBS Lett., vol. 341, p. 288-90, 1994). The relationship between the time elapsed from the start of the administration of compound (8) and the AM concentration in the plasma is shown in FIG. 7.

Figure 7:
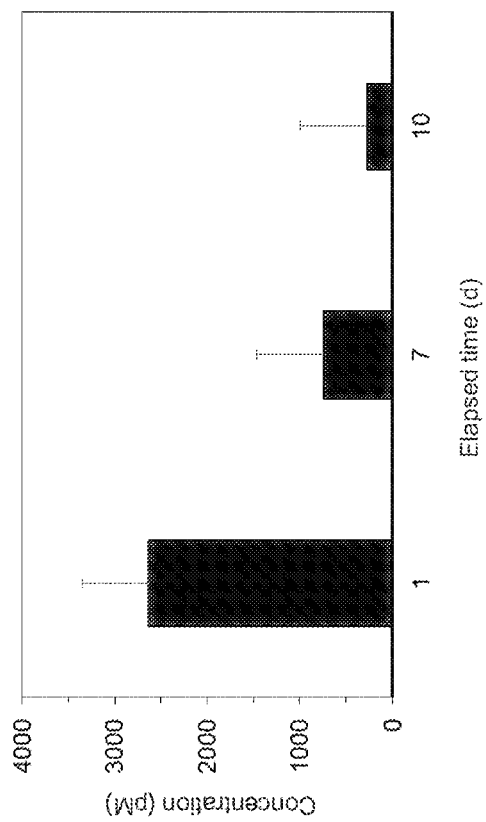
FIG. 7 shows the relationship between the time elapsed from the start of administration of compound (8) and AM concentration in blood plasma.

As shown in FIG. 7, when the compound (8) was administered, the AM concentration in the plasma was confirmed to be 2600 pM or higher 1 day later, 740 pM or higher 7 days later, and 280 pM or higher even 10 days later. On the other hand, when h.AM (1-52) was administered, the AM concentration in the plasma was 6.7 pM 1 day later (by the administration of the compound (8)) and 0 pM (equal to or lower than detection sensitivity) in both the measurements performed 7 days and 10 days later. The AM concentration in rat plasma is known to be typically on the order of 1 pM (Mori, Y. et al., Long-Term Adrenomedullin Infusion Improves Survival in Malignant Hypertensive Rats. Hypertension, 2002, vol. 40, p. 107-113.). These results demonstrated that the alkylamine linkage-type adrenomedullin derivative of the invention is present at a high concentration in blood over a significantly longer period as compared to the parent molecule adrenomedullin.

Experiment IV-4: Measurement Over Time of Concentration in Blood of Adrenomedullin Derivative Administered in Single Dose to Jugular Vein The compound (6) prepared in experiment I-1 or full-length AM was administered in a single dose of 3 nmol/kg into the vein of each rat under anesthesia, and time-dependent change in the concentration in blood of the adrenomedullin derivative was observed. Each 8 to 9-week-old male Wistar rat (approximately 300 g) was anesthetized by the inhalation of isoflurane. After tracheotomy, inhalational anesthesia was controlled at an isoflurane concentration of 1.5 to 2.5% and a flow rate of 0.6 to 0.8 L/min. The right jugular vein was isolated from the rat, and a catheter tube corresponding to 26 G was inserted thereto. Next, the left carotid artery was isolated from the rat thus treated, and a catheter tube corresponding to 23 G was inserted thereto. From the catheter tube of the right jugular vein, a physiological saline-heparin solution (physiological saline: 100 ml; heparin: 1000 units) was infused at 2.4 ml/hr. From this catheter tube, 3 nmol/kg of the compound (6) or h.AM(1-52) was administered in a form dissolved in physiological saline. From the catheter inserted in the carotid artery, 300 μl of blood was collected over time (1 hour, 2 hours and 4 hours after the start of the administration). Immediately, 300 μg of EDTA-2Na and 21 μg of aprotinin were added to the obtained blood sample, and the mixture was centrifuged under conditions involving 10 minutes and 3000 rpm to obtain plasma. The AM concentration in the plasma of each sample was measured by radioimmunoassay (Kitamura K, Ichiki Y, Tanaka M et al., Immunoreactive adrenomedullin in human plasma. FEBS Lett., vol. 341, p. 288-90, 1994). The relationship between the time elapsed from the start of the administration of the compound (6) or h.AM (1-52) and the AM concentration in the plasma is shown in FIG. 8.

Figure 8:
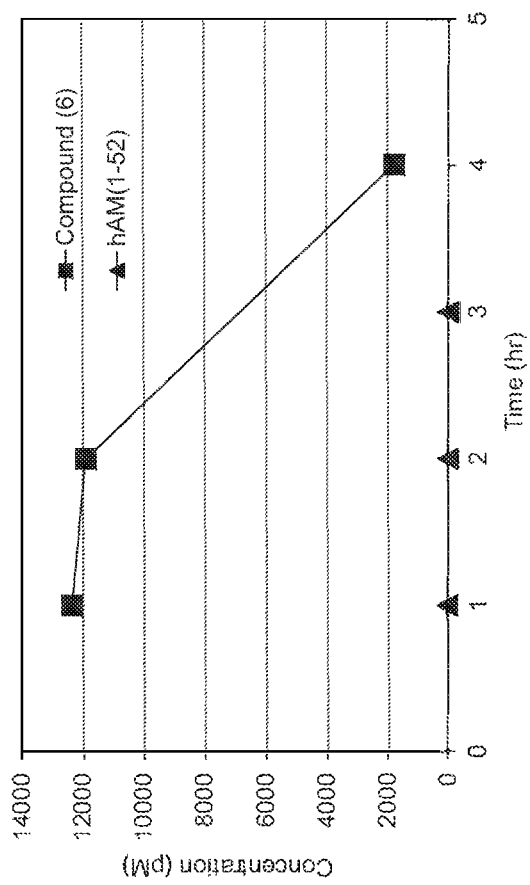
FIG. 8 shows the relationship between the time elapsed from the start of administration of compound (6) or h.AM (1-52) and AM concentration in blood plasma.

As shown in FIG. 8, the compound (6) significantly prolonged blood half-life as compared to h.AM (1-52). These results demonstrated that the alkylamine linkage-type adrenomedullin derivative of the invention significantly prolongs blood half-life as compared to the parent molecule adrenomedullin.

Experiment IV-5: Effect of Suppressing Increase in Blood Pressure in Spontaneously Hypertensive Rat (SHR Rat)-(1)

The compound (8) prepared in experiment I-1 was subcutaneously administered in a single dose of 336 μg/100 μL to each spontaneously hypertensive rat (SHR), and the blood pressure increase-suppressing effect of the adrenomedullin derivative was observed. Each 8-week-old male SHR (approximately 200 g) was fed with a high-salt diet (8% NaCl). The compound (8) was administered in a form dissolved in physiological saline at the time of feeding with the high-salt diet. 100 μL of physiological saline was subcutaneously administered in a single dose to each male SHR (approximately 200 g) in the same condition as above in a control group. The blood pressure and the pulse were measured over time (2 days before and 9 days after the administration of the compound (8) or physiological saline). The blood pressure values obtained 2 days before and 9 days after the administration of the compound (8) or physiological saline are shown in FIG. 9.

Figure 9:
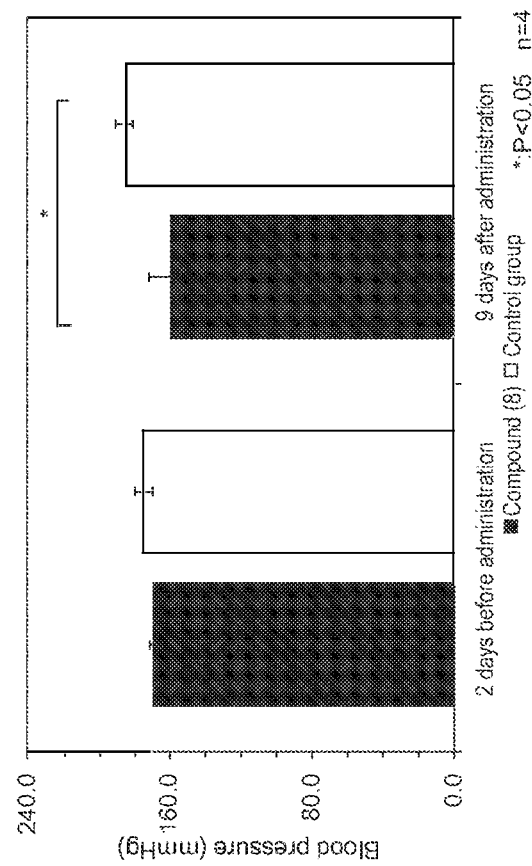
FIG. 9 shows the blood pressure values of spontaneously hypertensive rats 2 days before and 9 days after administration of compound (8) or physiological saline.

As shown in FIG. 9, increase in the blood pressure was suppressed in the compound (8) administration group compared to the control group (physiological saline administration group). These results demonstrated that the alkylamine linkage-type adrenomedullin derivative of the invention has a pharmacological effect of suppressing increase in the blood pressure.

Experiment IV-6: Measurement Over Time of Concentration in Blood of Subcutaneously Administered Adrenomedullin Derivative-(2)

The compound (27) prepared in experiment I-1 was subcutaneously administered in a single dose of 10 nmol/kg to each rat by the same procedures as in experiment IV-3, and time-dependent change in the concentration in blood of the adrenomedullin derivative was observed.

When the compound (27) was administered, the AM concentration in the plasma was confirmed to be 3600 pM or higher 1 day later and 120 pM or higher 7 days later. These results demonstrated that the urethane linkage-type adrenomedullin derivative of the invention is present at high concentration in blood over a significantly longer period as compared to the parent molecule adrenomedullin.

Experiment IV-7: Measurement Over Time of Concentration in Blood of Subcutaneously Administered Adrenomedullin Derivative-(3)

The compound (37) prepared in experiment III-1 was subcutaneously administered in a single dose of 30 nmol/kg to each rat, and time-dependent change in the concentration in blood of the adrenomedullin derivative was observed. The compound (37) dissolved in physiological saline was subcutaneously administered to each 7- to 8-week-old male Wistar rat (approximately 250 g). 1 day, 2 days, 4 days, 7 days and 9 days after the start of the administration, 50 mg of pentobarbital was intraperitoneally administered, and 300 μL of blood was collected each time from the tail vain under anesthesia. Immediately, 300 μg of EDTA-2Na and 21 μg of aprotinin were added to the obtained blood sample, and the mixture was centrifuged under conditions involving 10 minutes and 3000 rpm to obtain plasma. The AM concentration in the plasma of each sample was measured by RIA.

When the compound (37) was administered, the AM concentration in the plasma was confirmed to be 34000 pM or higher 1 day later, 1600 pM or higher 7 days later, and 110 pM or higher even 9 days later. These results demonstrated that the alkylamine linkage-type glycine-extended adrenomedullin derivative of the invention is present at high concentration in blood over a significantly longer period as compared to the parent molecule adrenomedullin.

Experiment IV-8: Effect of Suppressing Increase in Blood Pressure in Spontaneously Hypertensive Rat (SHR)-(2)

The compound (37) prepared in experiment III-1 was subcutaneously administered in a single dose of 30 nmol/kg to each SHR, and the blood pressure increase-suppressing effect of the adrenomedullin derivative was observed. The compound (37) was administered in a form dissolved in physiological saline to each 8-week-old male SHR (approximately 200 g). 100 L of physiological saline was subcutaneously administered in a single dose to each male SHR (approximately 200 g) in the same condition as above in a control group. The blood pressure was measured over time (1 day before and 4 days and 9 days after the administration of the compound (37) or physiological saline). The values of change in the blood pressure obtained 4 days and 9 days after the administration of the compound (37) or physiological saline with respect to the average systolic blood pressure on the day before the administration are shown in FIG. 10.

Figure 10:
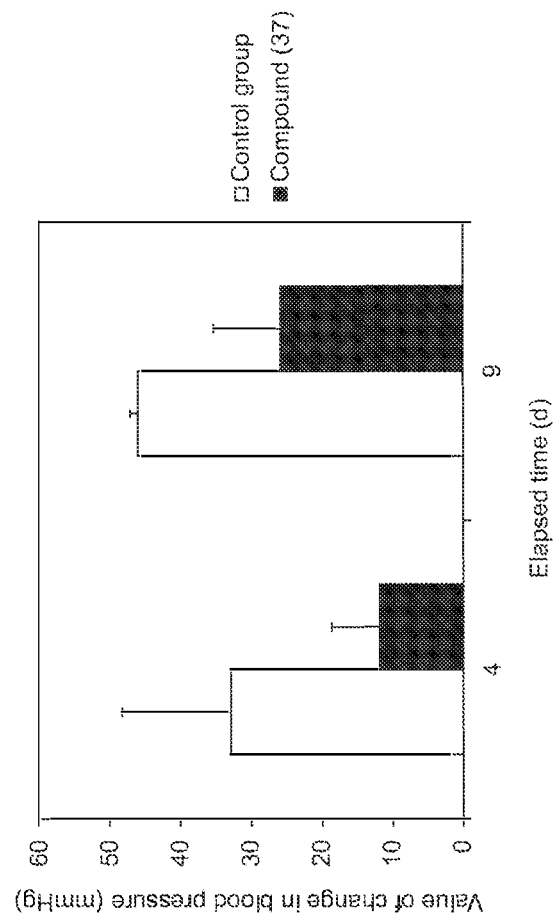
FIG. 10 shows the values of change in the blood pressure obtained 4 days and 9 days after administration of compound (37) or physiological saline with respect to the average systolic blood pressure on the day before administration.

As shown in FIG. 10, increase in the blood pressure was suppressed in the compound (37) administration group compared to the control group. These results demonstrated that the alkylamine linkage-type glycine-extended adrenomedullin derivative of the invention has a pharmacological effect of suppressing increase in the blood pressure.

Experiment IV-9: Pharmacological Effect on Dextran Sodium Sulfate (DSS)-Induced Colitis Model The compound (8) was studied for its improving effect on DSS-induced colitis models by subcutaneous administration. The compound (8) was subcutaneously administered to the back of each mouse. On the day following the administration (day 0), colitis model preparation was started by administration of 3% DSS as drinking water for 7 days. The dose of the compound (8) was set to 3 types of doses of 1, 5 and 25 nmol/kg. Physiological saline was administered as a vehicle to a control group. The body weight and the form of stool were evaluated on days 3, 5 and 7 counted from the start date of the DSS administration (day 0) on the basis of the scores shown in Table 4. The relationship between the time elapsed from the DSS-induced colitis model preparation and the total score in the compound (8) administration groups and the control group is shown in FIG. 11.

TABLE 4

| Score | Criteria |
|---|---|
| Weight loss | |
| 0 | Absent |
| 1 | 1~5% |
| 2 | 5~10% |
| 3 | 10~20% |
| Stool consistency | |
| 0 | Normal |
| 2 | Loose stool |
| 4 | Diarrhea |
| Bleeding/mucous and bloody stool | |
| 0 | Normal |
| 2 | Bleeding |
| 4 | Mucous and bloody stool |

Figure 11:
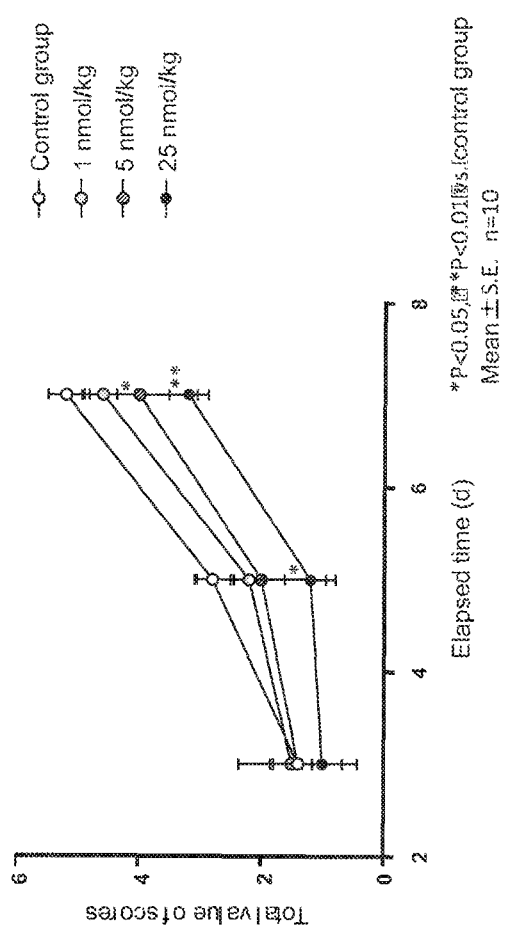
FIG. 11 shows the relationship between the time elapsed from dextran sodium sulfate (DSS)-induced colitis model preparation and the total values of scores in the compound (8) administration group and the control group.

As shown in FIG. 11, the 5 and 25 nmol/kg groups of the compound (8) administration groups was confirmed to exhibit significant decrease in the scores. The decrease in the scores suggests a colitis-alleviating effect. A tendency to decrease the wet weight of the intestinal tract was confirmed in the 5 nmol/kg administration group, and a tendency to increase the length of the intestinal tract was confirmed in the 25 nmol/kg administration group, as compared to the vehicle control group. These results suggested that the compound (8) has an alleviating effect on the pathological condition of the DSS colitis models under this test condition by subcutaneous administration.

Figure 12:
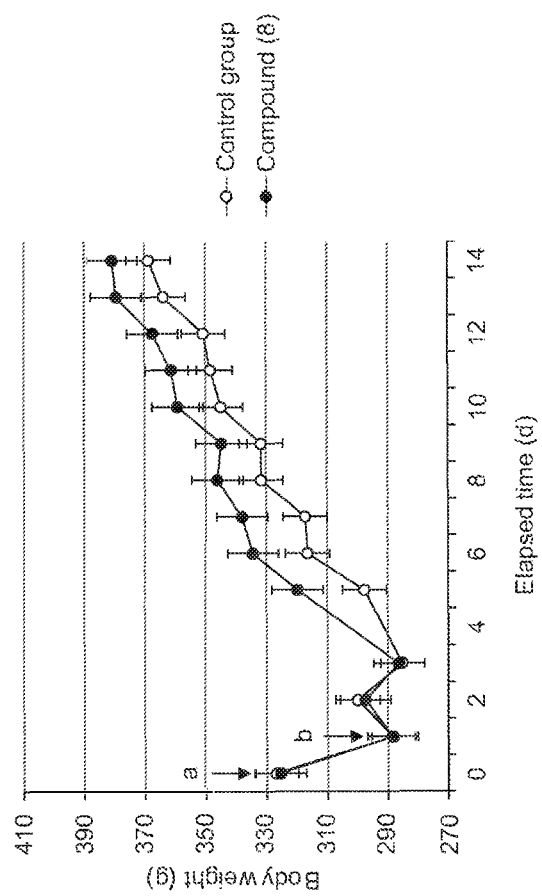
FIG. 12 shows the relationship between the time elapsed from 2,4,6-trinitrobenzenesulfonic acid (TNBS)-induced colitis model preparation and body weights in the compound (8) administration group and the control group. a: day on which compound (8) or physiological saline was subcutaneously administered and fasting was started; and b: day on which TNBS was administered.
Figure 13:
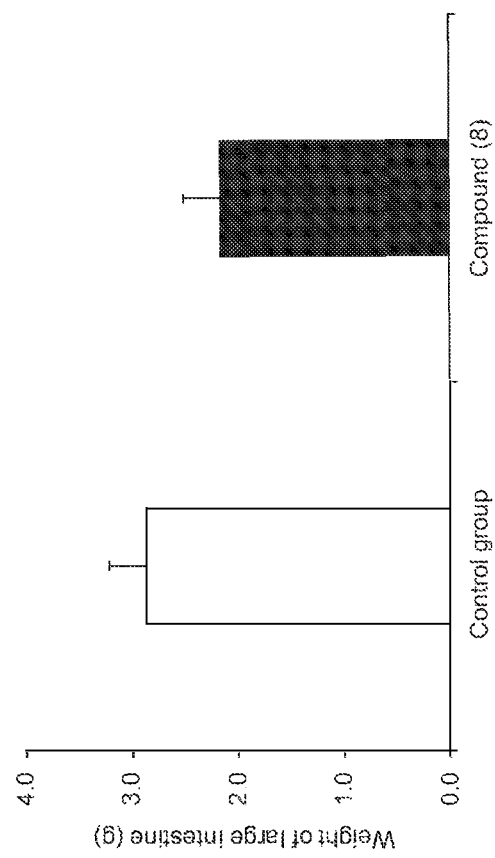
FIG. 13 shows the weights of the large intestines in the compound (8) administration group and the control group.
Figure 14:
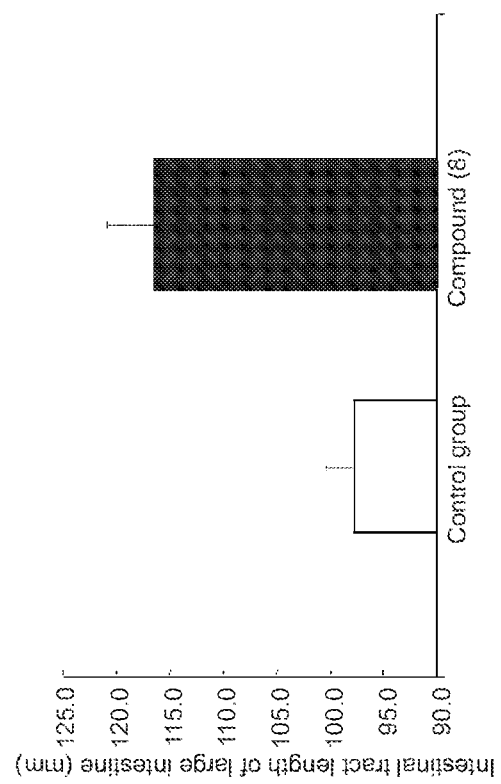
FIG. 14 shows the intestinal tract lengths of the large intestines in the compound (8) administration group and the control group.

Experiment IV-10: Pharmacological Effect on 2,4,6-Trinitrobenzenesulfonic Acid (TNBS)-Induced Colitis Model The compound (8) was studied for its improving effect on TNBS-induced colitis models by subcutaneous administration. 7-week-old male Wistar rats were acclimatized for 1 week. Then, the compound (8) (1 nmol/kg) or physiological saline was subcutaneously administered to each rat (day 0). Fasting was carried out for 24 hours concurrently with the subcutaneous administration to remove stool from the body. Colitis models were prepared by procedures described below. The concentration of TNBS (Nacalai Tesque, Inc.) was adjusted to 30 mg/500 µL (in a 50% aqueous ethanol solution). 50 mg of pentobarbital was intraperitoneally administered, and a polyethylene catheter was inserted by 8 cm from the anus under anesthesia while slowly rotated, followed by injection of 500 µL of the drug solution (day 1). Then, the inverted state was maintained for 2 minutes. The body weight and the form of diarrhea were evaluated every day. 14 days later, 50 mg of pentobarbital was intraperitoneally administered, and blood collection from the heart and excision of the large intestine were carried out under anesthesia. The length and weight of the excised intestinal tract were measured and compared between the groups. The relationship between the time elapsed from the TNBS-induced colitis model preparation and the body weights in the compound (8) administration group and the control group is shown in FIG. 12. In the diagram, (a) depicts the day on which the compound (8) or physiological saline was subcutaneously administered and fasting was started, and (b) depicts the day on which TNBS was administered. The weights of the large intestines in the compound (8) administration group and the control group are shown in FIG. 13. The intestinal tract lengths of the large intestines in the compound (8) administration group and the control group are shown in FIG. 14.

As shown in FIG. 12, weight loss due to the development of colitis was confirmed in the vehicle control group, whereas the weight loss due to the development of colitis was improved in the compound (8) administration group. As colitis is developed, the weight of the large intestine is typically increased due to swelling at the inflammatory site. As shown in FIG. 13, increase in the weight of the large intestine was evidently suppressed in the compound (8) administration group compared to the vehicle control group. As inflammation due to colitis progresses, the intestinal tract length of the large intestine is typically decreased. As shown in FIG. 14, decrease in the intestinal tract length of the large intestine was evidently suppressed in the compound (8) administration group compared to the vehicle control group. From autopsy report on the large intestine, evidently fewer pathological changes were also confirmed in the compound (8) administration group than the vehicle control group. These results suggested that the compound (8) has an alleviating effect on the pathological condition of the TNBS-induced colitis models under this test condition by subcutaneous administration. Therefore, the adrenomedullin derivative of the invention was found to have a therapeutic effect on colitis.

Experiment IV-11: Pharmacological Effect on Pulmonary Hypertension Model

The compound (8) was studied for its improving effect on pulmonary hypertension models by subcutaneous administration. 3-week-old male Wistar rats (Charles River Laboratories Japan, Inc.) were purchased and acclimatized for 1 week. Then, a monocrotaline solution was subcutaneously administered at a concentration of 60 mg/kg to each rat. At the same time therewith, the compound (8) (1 nmol/kg) or physiological saline was subcutaneously administered in a single dose to another position of the back. The general weight ratio between the right ventricle and the left ventricle of the heart was measured as an index for determining the effect on the pulmonary hypertension models. These models are known to exhibit increase in the weight ratio caused by hypertrophy of the right ventricle as the pathological condition progresses (Miyauchi T., Yorikane R., Sakai S., Sakurai T., Okada m., Nishikibe M., Yano M., Yamaguchi I., Sugishita Y. and Goto k.: Contribution of endogenous endothelin-1 to the progression of cardiopulmonary alterations in rats with monocrotaline-induced pulmonary hypertension. Circ. Res., vol. 73, pp. 887-897, 1993.). 14 days after the administration, 50 mg of pentobarbital was intraperitoneally administered, and blood was collected from the inferior vena cava under anesthesia. Then, the heart was excised, and its weight was measured. The excised heart was divided into the right ventricle and the left ventricle, and their respective weights were measured. The right ventricle weight/left ventricle weight ratio was calculated. The right ventricle weight/left ventricle weight ratios in the compound (8) administration group and the control group are shown in FIG. 15.

Figure 15:
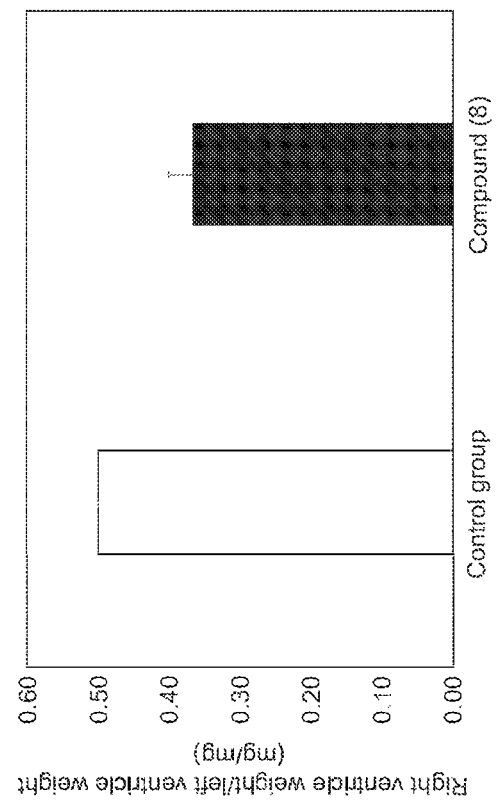
FIG. 15 shows right ventricle weight/left ventricle weight ratios in the compound (8) administration group and the control group.

As shown in FIG. 15, the compound (8) administration group had a significantly lower right ventricle/left ventricle weight ratio as compared to the vehicle control group. These results suggested that the compound (8) has an alleviating effect on the pathological condition of the pulmonary hypertension models under this test condition by subcutaneous administration.

Experiment IV-12: Pharmacological Effect on Wound Model

The compound (8) was studied for its pharmacological effect on wound models by subcutaneous administration. 5-week-old male BALB/c-nu/nu mice (Charles River Laboratories Japan, Inc.) were purchased and acclimatized for 1 week. Then, 5 mg of pentobarbital was intraperitoneally administered to each mouse for anesthesia. The skin was disinfected using ethanol for disinfection. The skin of the back was pulled with fingers with the mouse in the lateral position, and pressed and cut with a round knife for skin biopsy (disposable biopsy punch with plunger system) from one side toward the other side on a disinfected mat for drafting to prepare two defective injuries each having a diameter of 6 mm. At the same time therewith, the compound (8) (1 nmol/kg) was subcutaneously administered in a single dose to another position of the back. Physiological saline was administered as a vehicle to a control group. A dressing was applied to cover the back including the wound sites. Change in the wound areas were observed over time. The relationship between the time elapsed from the wound model preparation and the wound areas in the compound (8) administration group and the control group is shown in FIG. 16.

Figure 16:
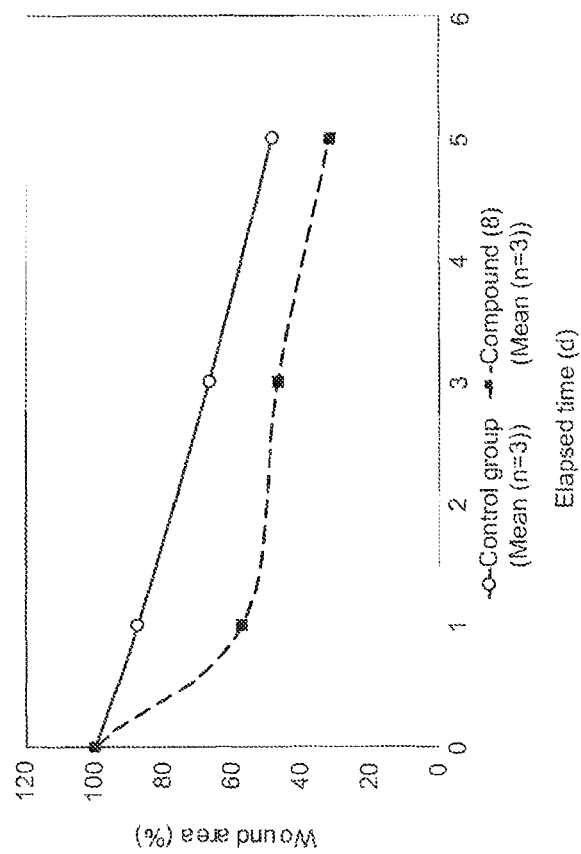
FIG. 16 shows the relationship between the time elapsed from wound model preparation and wound areas in the compound (8) administration group and the control group.

As shown in FIG. 16, reduction in the wound areas proceeded faster in the compound (8) administration group than the vehicle control group. These results demonstrated that the compound (8) has a wound healing-promoting effect under this test condition by subcutaneous administration.

Experiment IV-13: Pharmacological Effect on Vascular Occlusion Model

In accordance with the Morris water maze test, the compound (8) was studied for its pharmacological effect on learning and memory disorders in vascular occlusion model rats by subcutaneous administration. The compound (8) was subcutaneously administered to each rat before operation for vertebral artery occlusion. The dose of the compound (8) was set to two types of doses of 1 and 10 nmol/kg. Physiological saline was administered as a vehicle to a control group. Then, the bilateral vertebral arteries were permanently occluded under anesthesia. On the next day, the bilateral common carotid arteries were occluded for 30 minutes under anesthesia using a suture thread. Then, the suture thread was removed, and blood flow was restarted. The date of the bilateral common carotid artery occlusion was defined as the date of the vascular occlusion model preparation, i.e., day 0.9 days after the model preparation, the rat was caused to swim in the Morris water maze in one trial (training). The hidden platform test was conducted at intervals of 4 trials/day for 5 days from 10 days after the model preparation. On the fifth day of the hidden platform test (14 days after the model preparation), the probe test was conducted 1 hour after the final trial.

The Morris water maze test was conducted using an experimental apparatus described below. A round pool having a diameter of 150 cm, a height of 45 cm, and a water depth of 30 cm was provided. A clear colorless platform having a dimeter of 12 cm was positioned approximately 1 cm below the water surface in the round pool. The water temperature of the round pool was set to 23±1° C. Indirect lighting was disposed within the room having the experimental apparatus placed therein, and visual cues (calendar, ball, cube and striped sheet) for the animals were arranged therein. In the test period, this arrangement was always constant. A video tracking system (Smart, Panlab, S.L.U.) was used in measurement.

The hidden platform test was conducted by procedures described below. 9 days after the operation, the rat was caused to swim for 90 seconds without placing the platform and accustomed to water (training). Measurement was started from 10 days after the operation. The measurement was carried out at intervals of 4 trials/day. The swimming time to arrive at the platform from the start (escape latency) was measured. The start position was changed among the trials. The position of the platform was fixed to the same position for all the trials. The longest swimming time was set to 90 seconds per trial. A stay time of 30 seconds on the platform after the swimming was established for a rat that was unable to arrive at the platform within the longest swimming time.

The probe test was conducted by procedures described below. The pool was divided into 4 parts without placing the platform in the experimental apparatus. During the hidden platform test, the swimming time in a zone having the platform placed therein was measured. The stay rate (%) was calculated according to an expression given below using the measured swimming time. The swimming time of the probe test was set to 60 seconds. Only one trial was performed 1 hour after the termination of the final trial of the hidden platform test conducted 14 days after the model preparation.

$$\text{Stay rate (\%)} = \frac{\text{Swimming time (sec) in the zone having the platform placed therein}}{60 \ sec} \times 100$$

Figure 17:
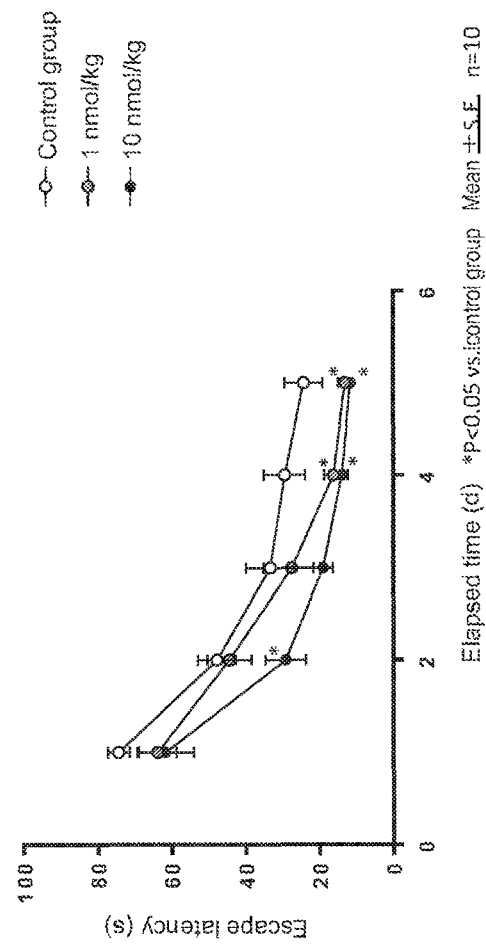
FIG. 17 shows the relationship between the time elapsed from vascular occlusion model preparation and escape latency in the hidden platform test in the compound (8) administration group and the control group.
Figure 18:
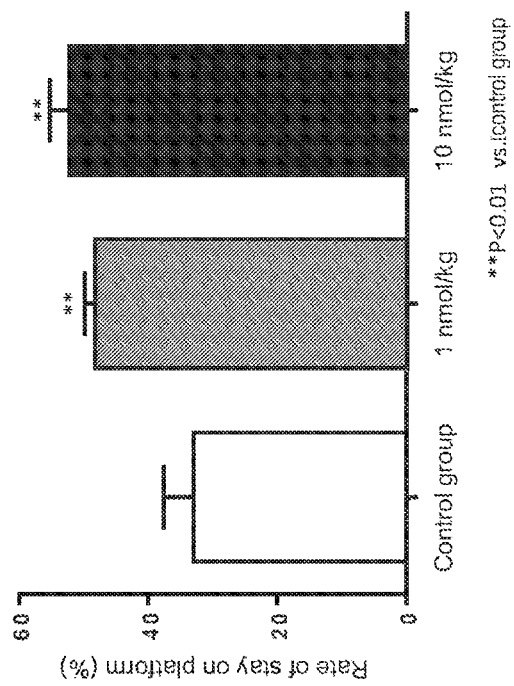
FIG. 18 shows stay rates in the probe test in the compound (8) administration group and the control group of vascular occlusion model rats.

The relationship between the time elapsed from the vascular occlusion model preparation and the escape latency in the hidden platform test in the compound (8) administration groups and the control group is shown in FIG. 17. The stay rates in the probe test in the compound (8) administration groups and the control group of the vascular occlusion model rats are shown in FIG. 18. As shown in FIG. 17, the 1 and 10 nmol/kg administration groups of the compound (8) administration groups shortened the time to arrive at the platform, i.e., the escape latency, in the hidden platform test as compared to the vehicle control group. As shown in FIG. 18, the 1 and 10 nmol/kg administration groups of the compound (8) administration groups also significantly increased the stay rate in the probe test as compared to the vehicle control group. In this test, no significant difference in the death rate associated with the operation for the bilateral common carotid artery occlusion was confirmed. These results demonstrated that the compound (8) has an alleviating effect on learning and memory disorders in the 4-vessel occlusion model rats under this test condition by subcutaneous administration.

Experiment IV-14: Pharmacological Effect on Adjuvant-Induced Arthritis Model

Figure 19:
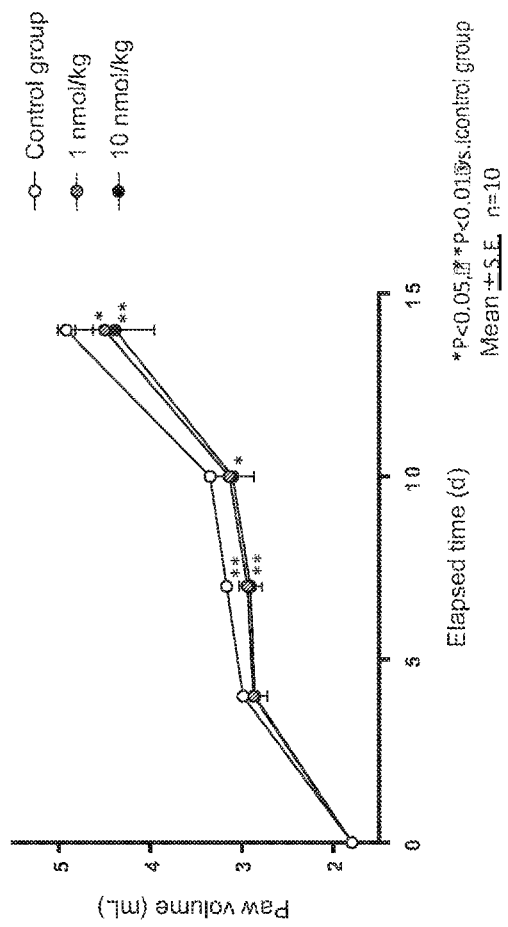
FIG. 19 shows the relationship between the time elapsed from administration of compound (8) or a vehicle and paw volumes exhibited after adjuvant administration in the compound (8) administration group and the control group.
Figure 20:
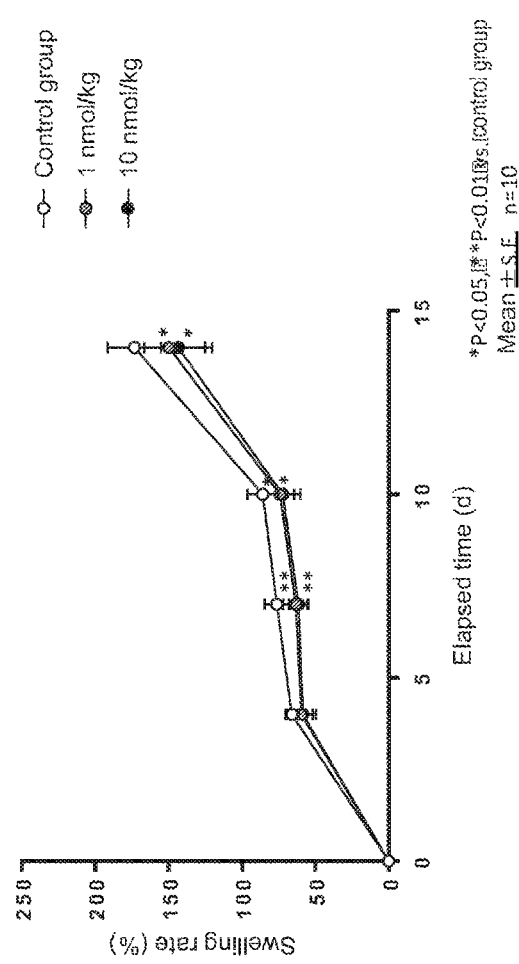
FIG. 20 shows the relationship between the time elapsed from administration of compound (8) or a vehicle and swelling rates exhibited after adjuvant administration in the compound (8) administration group and the control group.
Figure 21:
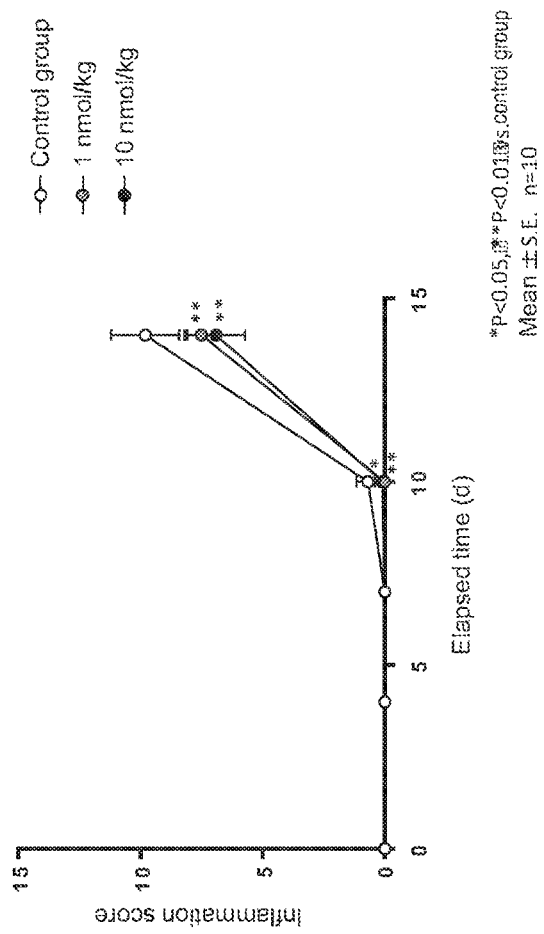
FIG. 21 shows the relationship between the time elapsed from administration of compound (8) or a vehicle and inflammation scores exhibited after adjuvant administration in the compound (8) administration group and the control group.

The compound (8) was studied for its pharmacological effect on adjuvant-induced arthritis models by subcutaneous administration. The compound (8) was subcutaneously administered to each rat. On the day following the administration of the compound (8) (day 1), an adjuvant (prophlogistic agent) was subcutaneously administered in a dose of 0.1 mL/animal to the right hind limb of the animal to induce arthritis. The dose of the compound (8) was set to two types of doses of 1 and 10 nmol/kg. Physiological saline was administered as a vehicle to a control group. The paw volumes and swelling rates of the right and left legs were measured on days 0 (day before the adjuvant administration), 4, 7, 10 and 14 using a paw volume measurement apparatus (MK-550, Muromachi Kikai Co., Ltd.). Inflammation scores on days 0 (day before the adjuvant administration), 4, 7, 10 and 14 were evaluated on the basis of the scores shown in Table 5. The relationship between the time elapsed from the administration of the compound (8) or the vehicle and the paw volumes exhibited after the adjuvant administration in the compound (8) administration groups and the control group is shown in FIG. 19. The relationship between the time elapsed from the administration of the compound (8) or the vehicle and the swelling rates exhibited after the adjuvant administration in the compound (8) administration groups and the control group is shown in FIG. 20. The relationship between the time elapsed from the administration of the compound (8) or the vehicle and the inflammation scores exhibited after the adjuvant administration in the compound (8) administration groups and the control group is shown in FIG. 21.

TABLE 5

| Score | Site | Criteria |
| --- | --- | --- |
| 0 | Right front limb | Normal |
| 1 | Left front limb<br>Left hind limb | Flare/swelling in only one small joint of the finger |
| 2 | | Flare/swelling in two or more small joints or relatively large joint of the ankle |
| 3 | | Flare/swelling in one whole limb |

TABLE 5-continued

| Score | Site | Criteria |
|---|---|---|
| 4 | 5 | When it was confirmed that overall swelling in one more limb reached the maximum level |

As shown in FIGS. 19 and 20, the 1 and 10 nmol/kg administration groups of the compound (8) administration groups significantly decreased the paw volume and the swelling rate as compared to the vehicle control group. As shown in FIG. 21, the 1 and 10 nmol/kg administration groups of the compound (8) administration groups significantly decreased the arthritis score as compared to the vehicle control group. These results demonstrated that the compound (8) has an alleviating effect on arthritis in the adjuvant-induced arthritis model rats under this test condition by subcutaneous administration.

All publications, patent and patent applications cited herein are incorporated herein by reference in their entirety.

The invention claimed is:

1. A compound represented by formula (X):

A'-CO—B  (X)

wherein

B is a peptide moiety derived from adrenomedullin or a modified form thereof with adrenomedullin activity, wherein the peptide moiety B is linked to A' through a covalent bond of the nitrogen atom of the N-terminal α-amino group of the peptide moiety B to the carbon atom of the carbonyl group, A' is a modifying group that is linked to the peptide moiety B through a covalent bond of the oxygen atom of the modifying group A' to the carbon atom of the carbonyl group, A' is represented by the following formula (XI):

$R^1$-O-$M^1$-*  (XI)

wherein $M^1$ is a polyethylene glycol group represented by formula (III):

—$(CH_2CH_2O)_n$—**  (III)

wherein n is an integer of 1 or larger,

* is a binding position to *, and # is a binding position to O, and with $R^1$ is substituted or unsubstituted C1-C20 alkyl.

2. The compound according to claim 1, wherein $R^1$ is a substituted or unsubstituted $C_1$-$C_{20}$ alkyl.

3. The compound according to claim 1, wherein $R^1$ is an unsubstituted $C_1$-$C_{20}$ alkyl.

4. The compound according to claim 1, wherein $R^1$ is a substituted or unsubstituted $C_1$ alkyl.

5. The compound according to claim 1, wherein A' is represented by formula (XI-1-1):

$CH_3O$—$(CH_2CH_2O)_n$—*  (XI-1-1).

6. The compound according to claim 5, wherein the polyethylene glycol group has a weight-average molecular weight of 5 kDa, 10 kDa, 20 kDa, 30 kDa, 40 kDa, 60 kDa or 80 kDa in total.

7. The compound according to claim 6, wherein the polyethylene glycol group has a weight-average molecular weight of 5 kDa in total.

8. The compound according to claim 6, wherein the polyethylene glycol group has a weight-average molecular weight of 10 kDa in total.

9. The compound according to claim 6, wherein the polyethylene glycol group has a weight-average molecular weight of 20 kDa in total.

10. The compound according to claim 6, wherein the polyethylene glycol group has a weight-average molecular weight of 30 kDa in total.

11. The compound according to claim 6, wherein the polyethylene glycol group has a weight-average molecular weight of 40 kDa in total.

12. The compound according to claim 6, wherein the polyethylene glycol group has a weight-average molecular weight of 60 kDa in total.

13. The compound according to claim 6, wherein the polyethylene glycol group has a weight-average molecular weight of 80 kDa in total.

14. The compound according to claim 1, wherein the peptide moiety B consists of an amino acid sequence of adrenomedullin and has a disulfide bond between two cysteine residues in the amino acid sequence.

15. The compound according to claim 14, wherein the adrenomedullin is human adrenomedullin.

16. The compound according to claim 15, wherein the amino acid sequence of adrenomedullin is SEQ ID NO: 1.

* * * * *